:

US011098362B2

(12) United States Patent
Umansky et al.

(10) Patent No.: US 11,098,362 B2
(45) Date of Patent: Aug. 24, 2021

(54) METHODS OF USING MIRNAS FROM BODILY FLUIDS FOR DETECTION AND MONITORING OF PARKINSON'S DISEASE (PD)

(71) Applicant: DIAMIR, LLC, Princeton, NJ (US)

(72) Inventors: Samuil R. Umansky, Princeton, NJ (US); Kira S. Sheinerman, New York, NY (US); Vladimir G. Tsivinsky, Sharon, MA (US)

(73) Assignee: DIAMIR, LLC, Princeton, NJ (US)

( * ) Notice: Subject to any disclaimer, the term of this patent is extended or adjusted under 35 U.S.C. 154(b) by 0 days.

(21) Appl. No.: 15/037,559

(22) PCT Filed: Nov. 17, 2014

(86) PCT No.: PCT/US2014/065959
§ 371 (c)(1),
(2) Date: May 18, 2016

(87) PCT Pub. No.: WO2015/073972
PCT Pub. Date: May 21, 2015

(65) Prior Publication Data
US 2016/0273043 A1    Sep. 22, 2016

Related U.S. Application Data

(60) Provisional application No. 61/935,806, filed on Feb. 4, 2014, provisional application No. 61/905,703, filed on Nov. 18, 2013.

(51) Int. Cl.
*C12Q 1/68* (2018.01)
*C12Q 1/6883* (2018.01)

(52) U.S. Cl.
CPC ..... *C12Q 1/6883* (2013.01); *C12Q 2600/106* (2013.01); *C12Q 2600/118* (2013.01); *C12Q 2600/136* (2013.01); *C12Q 2600/158* (2013.01); *C12Q 2600/178* (2013.01)

(58) Field of Classification Search
CPC ............ C12Q 1/6883; C12Q 2600/106; C12Q 2600/118; C12Q 2600/136; C12Q 2600/158; C12Q 2600/178
See application file for complete search history.

(56) References Cited

U.S. PATENT DOCUMENTS

| | | | |
|---|---|---|---|
| 4,785,507 A | 11/1988 | Miyazaki et al. |
| 4,829,304 A | 5/1989 | Baird |
| 4,939,663 A | 7/1990 | Baird |
| 7,653,509 B2 | 1/2010 | Bagwell |
| 7,897,356 B2 | 3/2011 | Klass et al. |
| 7,993,831 B2 | 8/2011 | Latham et al. |
| 8,486,626 B2 | 7/2013 | Umansky et al. |
| 8,632,967 B2 | 1/2014 | Kuroda et al. |
| 8,648,017 B2 | 2/2014 | Umansky et al. |
| 9,447,471 B2 | 9/2016 | Qu et al. |
| 9,540,692 B2 | 1/2017 | Xu |
| 9,605,315 B2 | 3/2017 | Patel et al. |
| 9,611,511 B2 | 4/2017 | Keller et al. |
| 9,708,667 B2 | 7/2017 | Yanai et al. |
| 9,726,676 B2 | 8/2017 | Grabe et al. |
| 9,790,554 B2 | 10/2017 | Keller et al. |
| 9,803,242 B2 | 10/2017 | Umensky et al. |
| 9,809,857 B2 | 11/2017 | Wang |
| 9,933,440 B2 | 4/2018 | Goetzel |
| 2007/0161004 A1 | 7/2007 | Brown et al. |
| 2008/0020390 A1 | 1/2008 | Mitchell et al. |
| 2008/0139801 A1 | 6/2008 | Umansky et al. |
| 2008/0171667 A1 | 7/2008 | Brown et al. |
| 2009/0004668 A1 | 1/2009 | Chen et al. |
| 2009/0075258 A1 | 3/2009 | Latham et al. |
| 2009/0081640 A1 | 3/2009 | Umansky et al. |
| 2009/0176723 A1 | 7/2009 | Brown et al. |
| 2010/0151480 A1 | 6/2010 | Taylor et al. |
| 2010/0167937 A1 | 7/2010 | Goldknopf et al. |
| 2010/0167948 A1 | 7/2010 | Krichevsky et al. |
| 2010/0184046 A1 | 7/2010 | Klass et al. |
| 2010/0196426 A1 | 8/2010 | Skog et al. |
| 2010/0216139 A1 | 8/2010 | Galas et al. |
| 2010/0227908 A1 | 9/2010 | Cairns et al. |
| 2010/0267804 A1 | 10/2010 | Port et al. |
| 2010/0279292 A1 | 11/2010 | Marsh et al. |
| 2010/0286044 A1 | 11/2010 | Litman et al. |
| 2010/0323357 A1 | 12/2010 | Nana-Sinkam et al. |
| 2011/0003704 A1 | 1/2011 | Skog et al. |

(Continued)

FOREIGN PATENT DOCUMENTS

| | | |
|---|---|---|
| CN | 101962685 B | 9/2012 |
| CN | 101942502 B | 9/2014 |
| EP | 0136944 A2 | 4/1985 |
| EP | 0381178 A1 | 8/1990 |
| EP | 2496714 A2 | 9/2012 |
| EP | 2699666 A1 | 2/2014 |
| EP | 2699697 A1 | 2/2014 |
| EP | 3071712 A1 | 9/2016 |
| EP | 3118334 A1 | 1/2017 |
| EP | 3133147 A1 | 2/2017 |
| JP | 2010-536372 A | 12/2010 |
| JP | 2010538653 A | 12/2010 |

(Continued)

OTHER PUBLICATIONS

Goetz. The History of Parkinson's Disease: Early Clinical Descriptions and Neurological Therapies. Cold Spring Harb Perspect Med 2011;1:a008862.*

(Continued)

*Primary Examiner* — Robert C Hayes
(74) *Attorney, Agent, or Firm* — Troutman Pepper Hamilton Sanders LLP

(57) ABSTRACT

The invention is directed to methods for early diagnosis, progression and treatment monitoring of Parkinson's disease (PD) and its differentiation from other neurodegenerative diseases by quantifying brain-enriched miRNA in bodily fluids.

15 Claims, 11 Drawing Sheets

(56) References Cited

U.S. PATENT DOCUMENTS

| | | |
|---|---|---|
| 2011/0053157 A1 | 3/2011 | Skog et al. |
| 2011/0053158 A1 | 3/2011 | Mambo et al. |
| 2011/0086348 A1 | 4/2011 | Prasad et al. |
| 2011/0111976 A1 | 5/2011 | Fare et al. |
| 2011/0117111 A1 | 5/2011 | Kwon et al. |
| 2011/0117560 A1 | 5/2011 | Spinale et al. |
| 2011/0143360 A1 | 6/2011 | Kuroda et al. |
| 2011/0160285 A1 | 6/2011 | Anderson et al. |
| 2011/0160290 A1 | 6/2011 | Tewari et al. |
| 2012/0034608 A1 | 2/2012 | Zhou et al. |
| 2012/0093936 A1 | 4/2012 | Lindenberg et al. |
| 2012/0184599 A1 | 7/2012 | Marcet et al. |
| 2012/0252693 A1 | 10/2012 | Umansky et al. |
| 2012/0270746 A1 | 10/2012 | Kuroda et al. |
| 2013/0012403 A1 | 1/2013 | Hu |
| 2013/0131194 A1 | 5/2013 | Skog et al. |
| 2014/0120545 A1 | 5/2014 | Umansky et al. |
| 2014/0170648 A1 | 6/2014 | Kuroda et al. |
| 2014/0194319 A1 | 7/2014 | Skog et al. |
| 2014/0194613 A1 | 7/2014 | Skog et al. |
| 2014/0256562 A1 | 9/2014 | Umansky et al. |
| 2014/0259192 A1 | 9/2014 | Saarma et al. |
| 2014/0357507 A1 | 12/2014 | Umansky et al. |
| 2015/0005365 A1 | 1/2015 | Zakharenko et al. |
| 2017/0107575 A1 | 4/2017 | Umansky et al. |
| 2017/0362656 A1 | 12/2017 | Umansky et al. |

FOREIGN PATENT DOCUMENTS

| | | |
|---|---|---|
| JP | 5624470 B2 | 11/2014 |
| RU | 2367959 C1 | 9/2009 |
| WO | 2005118806 A2 | 12/2005 |
| WO | 2007073737 A2 | 7/2007 |
| WO | 2008045505 A2 | 4/2008 |
| WO | 2008153692 A2 | 12/2008 |
| WO | 2009009457 A1 | 1/2009 |
| WO | 2009012468 A2 | 1/2009 |
| WO | 2009015357 A1 | 1/2009 |
| WO | 2009025852 A2 | 2/2009 |
| WO | 2009036236 A1 | 3/2009 |
| WO | 2009070653 A1 | 6/2009 |
| WO | 2009100029 A1 | 8/2009 |
| WO | 2009114681 A2 | 9/2009 |
| WO | 2009120877 A2 | 10/2009 |
| WO | 2009132273 A2 | 10/2009 |
| WO | 2009133915 A1 | 11/2009 |
| WO | 2009143379 A2 | 11/2009 |
| WO | 2009147519 A1 | 12/2009 |
| WO | 2010054386 A2 | 5/2010 |
| WO | 2010117829 A2 | 10/2010 |
| WO | 2011015720 A1 | 2/2011 |
| WO | 2011057003 A2 | 5/2011 |
| WO | 2012145363 A1 | 10/2012 |
| WO | 2012145409 A1 | 10/2012 |
| WO | 2013036936 A1 | 3/2013 |
| WO | 2015073972 A1 | 5/2015 |
| WO | 2015164431 A2 | 10/2015 |
| WO | 2017120285 A1 | 7/2017 |
| WO | 2017161256 A1 | 9/2017 |
| WO | 2017165458 A1 | 9/2017 |

OTHER PUBLICATIONS

Gene Cards entry for MIR146A, retrived from https://www.genecards.org/cgi-bin/carddisp.pl?gene=MIR146A&keywords=mir146 on Apr. 14, 2018.*

Japanese Office Action issued in Japanese Patent Application No. 2014-506516 dated Mar. 1, 2017.

Weber, J.A. et al., "The microRNA spectrum in 12 body fluids," Clin. Chem., 2010, vol. 56, pp. 1733-1741.

Chinese Office Action dated Nov. 24, 2015, which issued during prosecution of Chinese Application No. 201280030033.x.

Henriksen et al., "The future of blood-based biomarkers for Alzheimer's disease," Alzheimer's & Dementia 10 (2014) pp. 115-131.

Lin et al., "Multimodal MRI Neuroimaging Biomarkers for Cognitive Normal Adults, Amnestic Mild Cognitive Impairment, and Alzheimer's Disease," Neurology Research International vol. 2012, Article ID 907409, 17 pages.

Mapstone et al., "Plasma phospholipids identify antecedent memory impairment in older adults," Nature Medicine 20 (4): pp. 415-418 (2014).

European Search Report Issued in European Application No. EP16192259.6; dated Jan. 16, 2017, 2 pages.

Japanese Office Action Issued in Japanese Patent Application No. 2014-506516 dated Apr. 4, 2016 (and English-language translation thereof), 20 pages.

Miyachi, M. et al. "Circulating muscle-specifica microRNA, miR-206, as a potential diagnostic marker for rhabdomyosarcoma", Biochem. Biophys. Res. Commun. (2010), vol. 400, p. 89-93.

International Preliminary Report on Patentability issued in PCT/US2012/034098 dated Oct. 22, 2013; 15 pages.

Japanese Office Action Issued in Japanese Patent Application No. 2014-506501 dated Mar. 16, 2016 (and English-language translation thereof), 15 pages.

Australia Patent Examination Report No. 1 issued in Patent Application No. 2012245628 dated Jun. 8, 2016, 6 pages.

Landgraf, Pablo, A Mammalian microRNA Expression Atlas Based on Small RNA Library Sequencing, Cell, vol. 129 (7), pp. 1401-1414, 2007.

Laterza, Omar F., et al., "Plasma MicroRNAs as Diagnostically Sensitive and Specific Biomarkers of Tissue Injury", Clinical Chemistry, vol. 55:11, pp. 1-7, 2009.

Lee EJ, et al., Systematic evaluation of microRNA processing patterns in tissues, cell lines, and tumors, RNA, vol. 14, pp. 35-42, 2008.

Liang Y, et al., Characterization of microRNA expression profiles in normal human tissues, BMC Genomics, vol. 8, pp. 166-185, 2007.

Liu, Da-Zhi, et al., Brain and blood microRNA expression profiling of ischemic stroke, intracerebral hemorrhage, and kainate seizures, J Cereb Blood Flow Metab., advance online publication, 2009, doi:10.1038/jcbfm.2009.186, pp. 1-12.

Lodes, Michael J., et al., Detection of Cancer with Serum miRNAs on an Oligonucleotide Microarray. PLoS One, vol. 4(7): e6229, 2009.

Londin et al. "Analysis of 13 cell types reveals evidence for the expression of numerous novel primate- and tissue-specific microRNAs," Proc. Natl. Acad. Sci. USA, 2015, EII06-EII15.

Low LK, et al., Axon pruning: an essential step underlying the developmental plasticity of neuronal connections, Phil Trans R Soc B., vol. 361, pp. 1531-1544, 2006.

Lugli, Giovanni, et al., "Expression of microRNAs and their precursors in synaptic fractions of adult mouse forebrain", Journal of Neurochemistry, vol. 106, pp. 650-661, 2008.

Lugli, Giovanni, et al., "File S2. Entire list of measured human, rat and mouse microRNAs by microarray after filtering and normalization," Journal of Neurochemistry, vol. 106, 2008.

Maes, Olivier C., et al. "Methodology for Discovery of Alzheimer 's Disease Blood-Based Biomarkers", J Gerontol A Biol Sci Med Sci, vol. 64A, pp. 636-645, 2009.

Maes, Olivier C., et al. MicroRNA: Implications for Alzheimer Disease and other Human CNS Disorders, Current Genomics, vol. 10, pp. 154-168, 2009.

McDonald, et al., Analysis of circulating microRNA: pre analytical and analytical challenges, Clin Chem., vol. 57, pp. 833-840, 2011.

McKhann GM, et al., The diagnosis of dementia due to Alzheimer's disease: Recommendations from National Institute on Aging-Alzheimer's Association workgroups on diagnostic guidelines for Alzheimer's disease, Alzheimers Dement., vol. 7, pp. 263-269, 2011.

Miller G, Alzheimer's biomarker initiative hits its stride, Science, vol. 326, pp. 386-389, 2009.

Mitchell PS, et al., Circulating microRNAs as stable blood-based markers for cancer detection, Proc Natl Acad Sci USA, vol. 105, pp. 10513-10518, 2008.

(56) References Cited

OTHER PUBLICATIONS

Natera-Naranjo, Orlangie, et al., Identification and quantitative analyses of microRNAs located in the distal axons of sympathetic neurons, RNA, vol. 16, pp. 1516-1529, 2010.

Office Action issued in corresponding European Patent Application No. 10779376.2, dated Nov. 6, 2015.

Office Action Issued in Japanese Patent Application No. 2014-506501 dated Mar. 16, 2016 (and English-language translation thereof), 15 pages.

Olsen, Line, et al., MicroRNAs Show Mutually Exclusive Expression Patterns in the Brain of Adult Male Rats. PLoS One, vol. 4(10): e7225, 2009.

Peltier HJ, et al.. Normalization of microRNA expression levels in quantitative RT-PCR assays: identification of suitable reference RNA targets in normal and cancerous human solid tissues, RNA, vol. 14, pp. 844-852, 2008.

Ray S, et al., Classification and prediction of clinical Alzheimer's diagnosis based on plasma signaling proteins, Nat Med., vol. 13, pp. 1359-1362, 2007.

Satoh J-i, MicroRNAs and Their Therapeutic Potential for Human Diseases: Aberrant MicroRNA Expression in Alzheimer's Disease Brain, J Pharmacol Sci., vol. 114, pp. 269-275, 2010.

Satoh, "Molecular network of microRNA targets in Alzheimer's disease brains", Exp Neural., vol. 235, pp. 436-446, 2012, ePub Sep. 16, 2011.

Schipper, et al., MicroRNA expression in Alzheimer blood mononuclear cells, Gene Regul. Syst. Bio., Vo., 1, pp. 263-274, 2007.

Schmand B, et al., "Value of Neurophysiological Tests, Neuroimaging, and Biomarkers for Diagnosing Alzheimer's Disease in Younger and Older Age Cohorts", J Am Geriatr Soc., vol. 59, pp. 1705-1710, 2001.

Schratt, Gerhard M., et al., "A brain-specific microRNA regulates dendritic spine development", Nature, vol. 439, pp. 283-289, 2006.

Schratt, Gerhard, microRNAs at the synapse, Nature Reviews Neuroscience, vol. 10, pp. 842-849, 2009.

Sempere, Lorenzo F, et al., "Expression profiling of mammalian microRNAs uncovers a subset of brain-expressed microRNAs with possible roles in murine and human neuronal differentiation", Genome Biology, vol. 5:R13, pp. R13.1-R13.11, 2004.

Sheinerman et al. "Plasma microRNA biomarkers for detection of mild cognitive impairment," Aging, 2012, vol. 4 No. 9, pp. 590-605.

Sheinerman et al. "Analysis of organ-enriched micro-RNAs in plasma as an approach to development of Universal Screening Test: feasibility study," Journal of Translational Medicine, 2013, 11:304.

Sheinerman et al. "Circulating cell-free microRNA as biomarkers for screening, diagnosis, and monitoring of neurode-generative diseases and other neurologic pathologies," Front.Cell.Neurosci., 2013, vol. 7, Art. 150, pp. 1-10.

Sheinerman et al. "Early detection of neurodegenerative diseases," Cell Cycle, 2013, 12:1.

Sheinerman et al. "Plasma microRNA biomarkers for detection of mild cognitive impairment: biomarker validation study," Aging, 2013, vol. 5 No. 12, pp. 925-938.

Sheinerman et al. "Universal screening test based on analysis of circulating organ-enriched microRNAs: a noval approach to diagnostic screening," Expert Rev. Mol. Diagn., 2015, 15(3):329-338.

Shigeru Murayama et al., "The Pathology of Alzheimer's Disease", Clinician (2006), No. 553, p. 15-19.

Shingara, J. et al. "An optimized isolation and labeling platform for accurate microRNA expression profiling", RNA (2005), vol. 11, p. 1461-1470.

Skog J, et al., Glioblastoma microvesicles transport RNA and proteins that promote tumour growth and provide diagnostic biomarkers, Nat Cell Biol., vol. 10(12), pp. 1470-1476, 2008.

Sperling RA, et al., The diagnosis of dementia due to Alzheimer's disease: Recommendations from National Institute on Aging-Alzheimer's Association workgroups on diagnostic guidelines for Alzheimer's disease, Alzheimers Dement., vol. 7, pp. 280-292, 2011.

Supplementary Figures and Tables from Peltier et al. (RNA (2008), 14-844-852) (the balance of the article is of record as citation C47 in the IDS of Oct. 18, 2013).

Veerla, S. et al. "MiRNA expression in urothelial carcinomas: important roles of miR-10a, miR-222, miR-125b, miR-7 and miR452 for lung stage and metastasis, and frequent homozygous losses of miR-31", International Journal of Cancer (2009), vol. 124, p. 2236-2242.

Wang, Guo-Kun, et al., Circulating microRNA: a novel potential biomarker for early diagnosis of acute myocardial infarction in humans, European Heart Journal, vol. 31, Issue 6, pp. 659-666, 2010.

Wang, Kai, et al., Circulating microRNAs, potential biomarkers for drug-induced liver injury, Proc Natl Acad Sci USA, vol. 106(11), pp. 4402-4407, 2009.

Wang, Wang-Xia, et al., "The Expression of MicroRNA miR-107 Decreases Early in Alzheimer's Disease and May Accelerate Disease Progression through Regulation of β-Site Amyloid Precursor Protein-Cleaving Enzyme 1", The Journal of Neuroscience, vol. 28, pp. 1213-1223, 2008.

Xu, S. et al. "MicroRNA (miRNA) transcriptome of mouse retina and identification of a sensory organ-specific miRNA cluster", Journal of Biological Chemistry (2007), vol. 282, p. 25053-25066.

Yoo et al., Oxidative Stress Regulated Genes in Nigral Dopaminergic Neuronal Cells: Correlation with the Known Pathology in Parkinson's Disease, Molecular Brain Research, 2003, 110, 76-84.

Yoshiyama Y, et al., Synapse Loss and Microglial Activation Precede Tangles in P3015 Tauopathy Mouse Model, Neuron., vol. 53, pp. 337-351, 2007.

Lindner, Kirsten et al. "Circulating microRNAs: emerging biomarkers for diagnosis and prognosis in patients with gastrointestinal cancers", Clinical Science (2015), 128, pp. 1-15.

European Communication pursuant to Article 94(3) EPC dated Nov. 6, 2015, which issued during prosecution of European Application No. 10779376.2.

Sheinerman et al. "Plasma microRNA biomarkers for detection of mild cognitive impairment: biomarker validation study," Aging, 2012, vol. 4 No. 9, pp. 17-18, 560-605.

Adachi, Taichi, et al., Plasma MicroRNA 499 as a Biomarker of Acute Myocardial Infarction, Clinical Chemistry, vol. 56, No. 7, pp. 1183-1185, 2010.

Albert MS, et al., The diagnosis of mild cognitive impairment due to Alzheimer's disease: Recommendations from National Institute on Aging-Alzheimer's Association workgroups on diagnostic guidelines for Alzheimer's disease, Alzheimers Dement, vol. 7, pp. 270-279, 2011.

Australian Office Action Issued in Australian Patent Application No. 2012245628 dated Jun. 8, 2016, 6 pages.

Backes, Christina, et al., A dictionary on microRNAs and their putative target pathways, Nucleic Acids Res, vol. 38, pp. 4476-4486, 2010.

Bak, Mads, et al., MicroRNA expression in the adult mouse central nervous system, RNA., vol. 14(3), pp. 432-444, 2008.

Bartel DP, MicroRNAs: target recognition and regulatory functions, Cell, vol. 136, pp. 215-233, 2009.

Bishop DL, et al., Axon branch removal at developing synapses by axosome shedding, Neuron, vol. 44, pp. 651-661, 2004.

Braak, et al., Neuropathological staging of Alzheimer's related changes, Acta Neuropathol., vol. 82, pp. 239-259, 1991.

Brase, Jan C., et al., Circulating miRNAs are correlated with tumor progression in prostate cancer, International Journal of Cancer, vol. 128(3), pp. 608-616, 2011.

Brase, Jan C., et al., Serum microRNAs as non-invasive biomarkers for cancer, Molecular Cancer, vol. 9, pp. 306-315, 2010.

Bredesen "mCiRNA-Synaptic Crystal Ball?," Aging, 2012, vol. 4 No. II, pp. 732-733.

Sharras, Guillaume T., et al., Life and times of a cellular bleb, Biophys J., vol. 94(5), pp. 1836-1853, 2008.

Chen, Xi, Characterization of microRNAs in serum: a novel class of biomarkers for diagnosis of cancer and other diseases, Cell Research, vol. 18, pp. 997-1006, 2008.

(56) References Cited

OTHER PUBLICATIONS

Chim, Stephen S.C., et al., Detection and Characterization of Placental MicroRNAs in Maternal Plasma, Clinical Chemistry, vol. 54(3), pp. 482-490, 2008.
Chinese Office Action dated Jul. 23, 2014, which issued during prosecution of Chinese Application No. 201280030033.
Chinese Office Action dated Jun. 2, 2015, which issued during prosecution of Chinese Application No. 201280030O33.x.
Chinese Office Action dated Mar. 26, 2015, which issued during prosecution of Chinese Application No. 201280030048.6.
Shinese Office Action and English Translation thereof dated Aug. 5, 2015, which issued during prosecution of Chinese Application No. 201280030048.6.
Cogswell, John P., et al., "Identification of miRNA Changes in Alzheimer's Disease Brain and CSF Yields Putative Biomarkers and Insights into Disease Pathways", Journal of Alzheimer's Disease , vol. 14, pp. 27-41, 2008.
Eaton BA, et al., Synapse disassembly, Genes Dev., vol. 17, pp. 2075-2082, 2003.
Edbauer, D. et al., Regulation of synaptic structure and function by FMRP-associated microRNAs miR-125b and . miR-132, Neuron, vol. 65(3), pp. 373-384, 2010.
Emery, V., Alzheimer disease: are we intervening too late? J Neural Transm., vol. 118(9), pp. 1361-1378, 2011.
European Communication pursuant to Article 94(3) EPC dated Aug. 21, 2014, which issued during prosecution of European Application No. 10779376.2.
European Communication pursuant to Article 94(3) EPC dated Jan. 5, 2016, which issued during prosecution of European Application No. 12773705.4.
European Communication pursuant to Article 94(3) EPC dated Jun. 25, 2015, which issued during prosecution of European Application No. 12774179.1.
European Communication pursuant to Article 94(3) EPC dated May 24, 2013, which issued during prosecution of European Application No. 10779376.2.
European Search Report dated Jan. 26, 2015, which issued during prosecution of European Application No. 12773705.4.
European Search Report dated Oct. 30, 2014, which issued during prosecution of European Application No. 12774179.1.
Fackler OT, Grosse R., Cell motility through plasma membrane blebbing, J Cell Biol., vol. 181(6), pp. 879-884, 2008.
Geekiyanage, et al., Blood serum miRNA: Non-invasive biomarkers for Alzheimer's disease, Exp Neural., vol. 235, pp. 491-496, 2012, ePub Dec. 1, 2011.
Gillardon, et al. "MicroRNA and proteome expression profiling in early-symptomatic α-synuclein(A30P)-transgenic mice" Proteomics Clinical Application 2008, 2(5):697-705.
Griffiths-Jones S., et al., miRBase: microRNA sequences, targets and gene nomenclature, Nucleic Acids Res., vol. 34, Database issue: D140-D144, 2006.
Hebert, et al. "Alterations of the microRNA network cause neurodegenerative disease" 2009, Trends in Neurosciences, 32(4):199-206.
Hebert, et al., Loss of microRNA cluster miR-29a/b-1 in sporadic Alzheimer's disease correlates with increased BACEI/beta-secretase expression, Proc Natl Acad Sci USA, vol. 105, pp. 6415-6420, 2008.
Hua et al. "A Catalogue of Glioblastoma and Brain MicroRNAs Identified by Deep Sequencing," OMICS A Journal of Integrative Biology, 2012, vol. 16, No. 12, pp. 690-699.
Hua Y-J., et al., Identification and target prediction of miRNAs specifically expressed in rat neural tissue, BMC Genomics, vol. 10, pp. 214-225, 2009.
Hunter, Melissa Piper, et al., Detection of microRNA Expression in Human Peripheral Blood Microvesicles, PLoS One, 3(11): e3694, 2008.
International Preliminary Report on Patentability for International Appl. No. PCT/US2010/055495, dated May 8, 2012.
International Search Report and Written Opinion of the International Searching Authority dated Apr. 28, 2015 issued during prosecution of International Application No. PCT/US2014/065959.
International Search Report and Written Opinion of the International Searching Authority for International Application No. PCT/US2012/034098, dated Jul. 17, 2012.
International Search Report and Written Opinion of the International Searching Authority for International Application No. PCT/US2012/034025, dated Sep. 28, 2012.
International Search Report for International Appl. No. PCT/US2010/055495, dated Jun. 6, 2011.
Ji, Xi, et al., Plasma miR-208 as a Biomarker of Myocardial Injury, Clinical Chemistry, vol. 55(11), pp. 1944-1949, 2009.
Kemppainen, et al., MicroRNAs as biomarkers in blood and other biofluids, poster 2010? [Retrieved from the Internet Sep. 8, 2012: <http://www.asuragen.comipdfs/postersibiomarkers.pdf>].
Koirala S, et al., Pruning an Axon Piece by Piece, Neuron, vol. 44, pp. 578-580, 2004.
Kosaka, Nobuyoshi, et al., "Circulating microRNA in body fluid: a new potential biomarker for cancer diagnosis and prognosis", Cancer Sci., vol. 101, pp. 2087-2092, 2010.
Kosaka, Nobuyoshi, et al., Secretory Mechanisms and Intercellular Transfer of MicroRNAs in Living Cells, J Biol. Chem., vol. 285(23), pp. 17442-17452, 2010.
Kye MJ, et al., Somatodendritic microRNAs identified by laser capture and multiplex RT-PCR, RNA, vol. 13, pp. 1224-1234, 2007.
Liang, Y. "An expression meta-analysis of predicated microRNA targets identifies a diagnostic signature for lung cancer", BMC Med. Genomics (2008), vol. 1:61, p. 1-16.
Chinese Office Action dated Aug. 15, 2016, which issued during prosecution of Chinese Application No. 201280030033.X.
Chinese Office Action dated Aug. 5, 2015, which issued during prosecution of Chinese Application No. 201280030048.6.
European Communication dated Nov. 15, 2016, which issued during prosecution of European Application No. 16 185 046.6.
European Communication pursuant to Article 94(3) EPC dated Dec. 8, 2016, which issued during prosecution of European Application No. 12 773 705.4.
European Communication pursuant to Rules 161(2) and 162 EPC dated Nov. 26, 2013, which issued during prosecution of European Application No. 12 774 179.1.
European Communication pursuant to Rules 70(2) and 70a(2) EPC dated Nov. 18, 2014, which issued during prosecution of European Application No. 12 774 179.1.
European Extended Search Report Issued in European Application No. EP14 862 355.6; dated May 31, 2017, 9 pages.
European Extended Search Report Issued in European Application No. EP16 192 259.6; dated Jan. 24, 2017, 8 pages.
International Search Report and Written Opinion of the International Searching Authority dated May 8, 2017 issued during prosecution of International Application No. PCT/US2017/012258.
International Search Report for International Application No. PCT/US2017/23470, dated Jul. 31, 2017.
Issler, O., et al., "Determining the Role of microRNAs in Psychiatric Disorders," Nature Reviews Neuroscience, 2015, vol. 16, pp. 201-212.
Office Action issued in Japanese Patent Application No. 2014-506501 dated Apr. 4, 2016 (and English-language translation thereof) 20 pages.
Sperling, R.A., et al., "Toward defining the preclinical stages of Alzheimer's disease: Recommendations from the National Institute on Aging and the Alzheimer's Association workgroup", Alzheimer's & Dementia (2011), pp. 1-13.
Extended European Search Report received for European Patent Application No. 14862355.6, dated Jun. 9, 2017, 8 pages.
Final Office Action received for U.S. Appl. No. 13/508,262, dated Jul. 30, 2013, 19 pages.
Final Office Action received or U.S. Appl. No. 14/112,684, dated Apr. 28, 2016, 19 pages.
Final Office Action received for U.S. Appl. No. 14/112,765, dated Oct. 9, 2015, 18 pages.

(56) References Cited

OTHER PUBLICATIONS

International Preliminary Report on Patentability received for PCT Patent Application No. PCT/US2012/034025, dated Oct. 31, 2013, 9 pages.
International Preliminary Report on Patentability received for PCT Patent Application No. PCT/US2014/065959, dated Jun. 2, 2016, 15 pages.
"Mature Sequence hsa-rniR-127-3p", Available online at: <http://www.mirbase.org/cgi-bin/mature.pl? mature_acc=MIMAT0000446>, 1 page.
Non-Final Office Action received for U.S. Appl. No. 13/508,262, dated Mar. 7, 2013, 12 pages.
Non-Final Office Action received for U.S. Appl. No. 14/112,664, dated Jul. 9, 2015, 23 pages.
Non-Final Office Action received for U.S. Appl. No. 14/112,765, dated Apr. 28, 2015, 15 pages.
Non-Final Office Action received for U.S. Appl. No. 15/390,110, dated Jan. 31, 2018, 19 pages.
Office Action received for Canadian Patent Application No. 2,780,222, dated Jan. 18, 2018, 5 pages.
Office Action received for Canadian Patent Application No. 2,833,375, dated Nov. 24, 2017, 7 pages.
Office Action received for Canadian Patent Application No. 2,833,389, dated Nov. 21, 2017, 4 pages.
Office Action received for Chinese Patent Application No. 201280030048.6, dated Aug. 5, 2014.
Office Action received for European Patent Application No. 12773705.4, dated Sep. 16, 2014, 6 pages.
Office Action received for European Patent Application No. 14862355.6, dated Mar. 20, 2018, 5 pages.
Delrieu et al., "Managing Cognitive Dysfunction through the Continuum of Alzheimer's Disease", CNS Drugs, vol. 25, No. 3, 2011, pp. 213-226.
Liu et al., "A Five-microRNA Signature Identified from Genome-wide Serum microRNA Expression Profiling Serves as a Fingerprint for Gastric Cancer Diagnosis", European Journal of Cancer, vol. 47, 2011, pp. 784-791.
Mestdagh et al., "High-throughput Stem-loop RT-qPCR miRNA Expression Profiling Using Minute Amounts of Input RNA", Nucleic Acids Research, vol. 36, No. 21, 2008, 8 pages.
Petersen et al., "Prevalence of Mild Cognitive impairment is Higher in Men", The Mayo Clinic Study of Aging, Neurology, vol. 75, Sep. 7, 2010, pp. 889-897.
Vlaminck et al.: "Circulating Cell-Free DNA Enables Noninvasive Diagnosis of Heart Transplant Resection", Science Translational Medicine, vol. 6, No. 241, Jun. 18, 2014, pp. 1-19.
Wang, Xiaowei, "A PCR-based Platform for microRNA Expression Profiling Studies", RNA, vol. 15, 2009, pp. 716-723.
Wu et al., "Next-Generation Sequencing of MicroRNAs for Breast Cancer Detection", Journal of Biomedicine and Biotechnology, vol. 2011, Article ID 597145, 2011, 7 pages.
Zampetaki et al., "Plasma microRNA Profiling Reveals Loss of Endothelial MiR-126 and Other microRNAs in Type 2 Diabetes", Circulation Research, vol. 107, 2010, pp. 810-817.
Zhao et al., "A Pilot Study of Circulating miRNAs as Potential Biomarkers of Early Stage Breast Cancer", PLoS One vol. 5, No. 10, Oct. 2010, 12 pages.
Japanese Communication (First Office Action) received for Japanese Patent Application No. 2017-174778, dated Nov. 16, 2018, 21 pages total.
Canadian Communication received for Canadian Patent Application No. 2,780,222 dated Jan. 28, 2019, 5 pages total.
European Communication (Article 94(3) EPC) received for European Application No. 14862355.6, dated Jan. 22, 2019, 8 pages total.
Sheinerman, K.S. et al., "Circulating Brain-Enriched MicroRNAs as Novel Biomarkers for Detection and Differentiation of Neurodegenerative Diseases" Alzheimer's Research & Therapy (2017) vol. 9, No. 89, 13 pages total.
Japanese Patent Office Communication received for Japanese Patent Application No. 2016-532043, dated Oct. 2, 2018, 17 pages total.
Chinese Office Action dated Mar. 26, 2019, which issued during prosecution of Chinese Application No. 201480073413.0, 8 pages total.
Chinese Office Action dated Mar. 25, 2019, which issued during prosecution of Chinese Application No. 201610344816.5, 13 pages total.
Final Office Action received for U.S. Appl. No. 15/606,747, dated Dec. 26, 2018, 40 pages.
Non-Final Office Action received for U.S. Appl. No. 15/390,110, dated Sep. 25, 2018, 30 pages.
Canadian Communication received for Canadian Patent Application No. 2,833,375, dated Oct. 12, 2018, 7 pages total.
Canadian Communication received for Canadian Patent Application No. 2,833,389, dated Oct. 18, 2018, 3 pages total.
Australia Patent Examination Report No. 1 issued in Australian Patent Application No. 2012245580 dated Aug. 30, 2016, 3 pages.
Australia Patent Examination Report No. 2 issued in Australian Patent Application No. 2012245580 dated Jun. 2, 2017, 4 pages.
Boeri, M. et al., "MicroRNA Signatures in Tissues and Plasma Predict Development and Prognosis of Computed Tomography Detected Lung Cancer" PNAS (2011) vol. 108, No. 9, pp. 3713-3718.
Canadian Communication received for Canadian Patent Application No. 2,780,222, dated Nov. 18, 2016, 4 pages.
European Communication (extended European search report) dated Feb. 27, 2018, which issued during prosecution of European Application No. 17207859.4, 9 pages total.
International Preliminary Report on Patentability received for PCT Patent Application No. PCT/US2017/012258, dated Jul. 10, 2018, 12 pages.
Kroh, E.M. et al., "Analysis of Circulating MircoRNA Biomarkers in Plasma and Serum Using Quantitative Reverse Transcription-PCR (qRT-PCR)" Methods (2010) vol. 50, pp. 298-301.
Meyer, S.U. et al., "Normalization Strategies for MircoRNA Profiling Experiments: A 'Normal' Way to a Hidden Layer of Complexity?" Biotechnol. Lett. (2010) vol. 32, pp. 1777-1788.
MirVana PARIS Kit Instructions Ambion, Life Technologies (2011) 36 pages total.
Non-Final Office Action received for U.S. Appl. No. 15/606,747, dated Jun. 1, 2018, 60 pages.
Pogue, A.I. et al., "Micro RNA-125b (miRNA-125b) Function in Astrogliosis and Glial Cell Proliferation" Neuroscience Letters (2010) vol. 476, pp. 18-22.
Communication (International Preliminary Report on Patentability) issued by the International Searching Authority in International Patent Application No. PCT/US2017/023470 dated Jul. 31, 2017, 20 pages total.
Communication (Written Opinion) issued by the International Searching Authority in International Patent Application. No. PCT/US2017/023470 dated Jul. 31, 2017, 19 pages total.
Restriction Requirement received for U.S. Appl. No. 16/044,279, dated Oct. 8, 2019, 12 pages total.
Chinese Office Action dated Sep. 20, 2019, which issued during prosecution of Chinese Application No. 201480073413.0, 15 pages total.
Japanese Office Action dated Aug. 13, 2019, which issued during prosecution of Japanese Application No. 2016-532043, 10 pages total.
Canadian Communication received for Canadian Patent Application No. 2,833,389, dated Nov. 22, 2019, 4 pages total.
European Communication (Extended European Search Report) received for European Application No. 17771018.3, dated Sep. 20, 2019, 9 pages total.
Cloutier, F. et al., "MicroRNAs as Potential Circulating Biomarkers for Amyotrophic Lateral Sclerosis" Journal of Molecular Neuroscience (2014) vol. 56, No. 1, pp. 102-112.
Kansara, S. et al., "Early Diagnosis and Therapy of Parkinson's Disease: Can Disease Progression be Curbed?" J. Neural Transm. (2013) vol. 120, pp. 197-210.

(56) References Cited

OTHER PUBLICATIONS

Abdel-Salam, O.M.E. et al., "Drugs Used to Treat Parkinson's Disease, Present Status and Future Directions" CNS & Neurological Disorders—Drug Targets (2008) vol. 7, pp. 321-342.
Gazewood, J.D. et al., "Parkinson Disease: An Update" American Family Physician (2013) vol. 87, No. 4, pp. 267-273.
Restriction Requirement received for U.S. Appl. No. 16/028,206, dated Dec. 13, 2019, 11 pages total.
Canadian Communication received for Canadian Patent Application No. 2,833,375, dated Dec. 9, 2019, 5 pages.
Coleman, R.A., "Of Mouse and Man—What is the Value of the Mouse in Predicting Gene Expression in Humans?" Drug Discovery Today (2003) vol. 8, No. 6, pp. 233-235.
Heegaard, N.H.H. et al., "Circulating Micro-RNA Expression Profiles in Early Stage Nonsmall Cell Lung Cancer" International Journal of Cancer (2012) vol. 130, pp. 1378-1386.
Liu, Z. et al., "Comparison of Differentially Expressed Genes in T Lymphocytes Between Human Autoimmune Disease and Murine Models of Autoimmune Disease" Clinical Immunology (2004) vol. 112, pp. 225-230.
Non-Final Office Action received for U.S. Appl. No. 16/086,881, dated Jun. 9, 2020, 34 pages total.
Urdinguio, R.G. et al., "Disrupted microRNA Expression Caused by Mecp2 Loss in a Mouse Model of Rett Syndrome" Epigenetics (2010) vol. 5, Issue 7, pp. 656-663.
Non-Final Office Action received for U.S. Appl. No. 16/028,206, dated May 21, 2020, 22 pages total.
Ashrafi, A. et al., "Leukocyte Telomere Length is Unrelated to Cognitive Performance Among Non-Demented and Demented Persons: An Examination of Long Life Family Study Participants" Journal of International Neuropsychological Society (2020) 12 pages total.
Restriction Requirement received for U.S. Appl. No. 16/086,881, dated Jan. 15, 2020, 8 pages total.
Alzforum: Networking for a Cure, "Genetics Tie ALS into the Frontotemporal Dementia Spectrum" (2018) Available online at: <https://www.alzforum.org/news/research-news/genetics-tie-als-frontotemporal-dementia-spectrum>, 5 pages total.
Schymick, J. C. et al., "Expanding the Genetics of Amyotrophic Lateral Sclerosis and Frontotemporal Dementia" Alzheimer's Research & Therapy (2012) vol. 4, No. 30, 6 pages total.
Stem-loop Sequence has-mir-491 Accession No. MI0003126, Available online at: <http://www.mirbase.org/cgi-bin/mirna_entry.pl?acc=MI0003126>, 3 pages total.
Stem-loop Sequence has-mir-335 Accession No. MI0000816, Available online at: <http://www.mirbase.org/cgi-bin/mirna_entry.pl?acc=MI0000291>, 4 pages total.
Harman, D., "Alzheimer's Disease: Role of Aging in Pathogenesis" Annals New York Academy of Sciences (2002) vol. 959, pp. 384-395.
Osmanovic-Barilar, J. et al., "Evaluating the Role of Hormone Therapy in Postmenopausal Women with Alzheimer's Disease" Drugs Aging (2016) vol. 33, pp. 878-808.
Non-Final Office Action received for U.S. Appl. No. 16/044,279, dated Feb. 14, 2020, 61 pages total.
Canadian Communication received for Canadian Patent Application No. 2,780,222, dated May 21, 2020, 6 pages total.
Japanese Communication received for Japanese Patent Application No. 2016-532043, dated May 28, 2020, 15 pages total.
Hustad, E. et al., "Clinical and Imaging Markers of Prodromal Parkinson's Disease" Frontiers in Neurology (2020) vol. 11, Article 395, 11 pages total.
Schapira, A.H.V. et al., "Timing of Treatment Initiation in Parkinson's Disease: A Need for Reappraisal?" American Neurological Association (2006) vol. 59, No. 3, pp. 559-561.
Pagan, F.L., "Improving Outcomes Through Early Diagnosis of Parkinson's Disease" The American Journal of Managed Care (2012) vol. 18, No. 7, pp. S176-S182.
Canadian Communication received for Canadian Patent Application No. 2,833,375, dated Dec. 15, 2020, 5 pages.
Canadian Communication received for Canadian Patent Application No. 2,833,389, dated Oct. 5, 2020, 3 pages total.
Chinese Office Action dated Jul. 3, 2020, which issued during prosecution of Chinese Application No. 201610344816.5, 10 pages total.
European Communication (Communication pursuant to Article 94(3) EPC) received for European Application No. 17771018.3, dated Oct. 9, 2020, 6 pages total.
Final Office Action received for U.S. Appl. No. 16/086,881, dated Dec. 14, 2020, 29 pages total.
Japanese Communication received for Japanese Patent Application No. 2016-532043, dated Nov. 20, 2020, 13 pages total.
Non-Final Office Action received for U.S. Appl. No. 15/037,559, dated Sep. 30, 2020, 23 pages.
Canadian Communication received for Canadian Patent Application No. 2,931,082, dated Jan. 29, 2021, 4 pages.

* cited by examiner

| Name | miR-107 / miR-132 | miR-107 / miR-146b | miR-107 / miR-335 |
|---|---|---|---|
| AUC | 0.97 | 0.98 | 1.00 |
| Sensitivity | 0.80 | 0.90 | 1.00 |
| Specificity | 1.00 | 0.95 | 1.00 |
| Accuracy | 0.90 | 0.93 | 1.00 |

METHODS OF USING MIRNAS FROM BODILY FLUIDS FOR DETECTION AND MONITORING OF PARKINSON'S DISEASE (PD)

CROSS-REFERENCE TO RELATED APPLICATIONS

This application is the U.S. National Phase application under 35 U.S.C. § 371 of International Patent Application No. PCT/US2014/065959, filed on Nov. 17, 2014, and claims priority to U.S. Provisional Patent Application No. 61/905,703, filed on Nov. 18, 2013 and U.S. Provisional Patent Application No. 61/935,806, filed on Feb. 4, 2014, the disclosures of which are herein incorporated by reference in their entirety.

TECHNICAL FIELD OF THE INVENTION

The present invention is directed to methods for early diagnosis, progression and treatment monitoring of Parkinson's disease (PD) and its differentiation from other neurodegenerative diseases by quantifying brain-enriched miRNAs in bodily fluids.

BACKGROUND OF THE INVENTION

Parkinson's disease (PD) is the second most common neurodegenerative disease. Approximately 60,000 Americans are diagnosed with Parkinson's disease each year, and an estimated 0.5 and 7-10 million people in USA and worldwide, respectively, are living with Parkinson's disease (http://www.parkinson.org/parkinson-s-disease.aspx; http://www.pdf.org/en/parkinson_statistics).

The annual economic impact of Parkinson's disease in the United States is estimated to be around $10.8 billion and growing (http://www.parkinsoninfo.org/about-parkinsons-disease/economic-impact/).

The combined direct and indirect cost of Parkinson's, including treatment, social security payments and lost income from inability to work, is estimated to be nearly $25 billion per year in the United States alone (http://www.pdf.org/en/parkinson_statistics).

Mechanisms of PD development are not well understood although many underlying processes have been described (Walter and Schulz-Schaeffer. Acta Neuropathol. 2010; 120: 131-143; David Sulzer. Trends in Neurosciences. 2007; 30: 244-250). PD is initiated by metabolic disorders, including abnormal processing of alpha-synuclein, which aggregates form so called Levy bodies, followed by synapse dysfunction, destruction and finally by neuronal death (Kazantsev A G, Kolchinsky A M. Arch Neurol. 2008; 65:1577-1581). Neurons of the substantia nigra in midbrain are maximally suffering in PD (Walter and Schulz-Schaeffer. Acta Neuropathol. 2010; 120: 131-143) but other brain areas, such as frontal cortex (Braak et al. Neurobiology of Aging. 2003; 24: 197-211; Hou et al. J. Clin. Neuroscience. 2010; 17: 628-633), are also involved in the pathology at different stages of PD development. The substantia nigra in midbrain produces dopamine, which transmits signals to the corpus striatum involved in movement regulation and significant decrease in dopamine production causes numerous movement disorders characteristic of PD. The latter (tremor, postural instability and parkinsonian gait, rigidity, masked face, and bradykinesia) are currently the major symptoms used for PD diagnosis (Parkinson's Disease: Diagnosis and Clinical Management. Editors: Factor and Weiner, $2^{nd}$ edition. 2008, Demos Medical Publishing, LLC, New York, N.Y.). There are other symptoms, which are developed by some PD patients, such as cognitive problems, which can lead to PD dementia, depression, skin problems, olfactory dysfunction and others (Aarsland et al. Mov. Disord. 2005; 20: 1255-1263; Song et al. Eur. Neurol. 2008; 59: 49-55; Mollenhauer et al. Neurology. 2013; 81:1226-1234). Some data indicate involvement of inflammatory processes in PD development (Tansey and Goldberg. Neurobiol. Dis. 2010; 37:510-518; Amor et al. Immunology. 2013 Dec. 16. [Epub ahead of print]).

Currently, there is no effective cure for PD, although medication and surgery can improve some symptoms of PD (Gazewood et al. Am. Fam. Physician. 2013; 87: 267-273). For example, dopamine replacement drugs such as L-DOPA and its combination with dopa decarboxylase inhibitors are widely used. Dopamine receptor agonists, monoamine oxidase and catechol o-methyltransferase inhibitors are other classes of drugs used to treat PD (Kansara et al. J. Neural Transm. 2013; 120: 197-210). Changes in lifestyle and physical therapy help to slow down PD progression.

As for other neurodegenerative diseases a long asymptomatic period is characteristic of PD and by the time of PD clinical manifestation 60-80% of dopamine-producing neurons are dead. Thus, biomarkers for early PD detection are highly needed for anti-PD drug development, clinical trials, timely diseases treatment, and disease and treatment monitoring (Lang. Neurology. 2009; 72 (Suppl. 7): S39-43; Jann M W. Am. J. Manag. Care. 2011; 17 Suppl 12:S315-21; Sharma et al. Neurochem Int. 2013; 63:201-229). As with AD, imaging technologies (de la Fuente-Fernandez et al. Expert Opin. Med. Diagn. 2011; 5:109-120; Huddleston et al. Clin. Med. Res. 2013; 11:141) and analysis of proteins in cerebrospinal fluid (Parnetti et al. Nat. Rev. Neurol. 2013; 9:131-140) demonstrated promising results but due to invasiveness and high cost these techniques cannot be used for primary screening. Data on analysis of α-synuclein in blood plasma (Foulds et al. Sci. Rep. 2013; 3:2540) and other approaches (Sharma et al. Neurochem Int. 2013; 63:201-229) appear promising but need additional validation studies. Another issue with significant clinical implications is differentiation of PD from other neurodegenerative diseases and syndromes, such as, e.g., Alzheimer's disease (AD) and Mild Cognitive Impairment (MCI) (Pahwa and Lyons. Am. J. Manag. Care. 2010; 16 Suppl. Implications: S94-99).

Recently, the present inventors have proposed a new approach for early detection of neurodegenerative diseases based on analysis of circulating cell-free miRNA in bodily fluids (Sheinerman et al. Aging (Albany N.Y.). 2012; 4: 590-605; Sheinerman and Umansky. Cell Cycle. 2013; 12: 1-2; Sheinerman and Umansky. Front Cell Neurosci. 2013; 7: 150; Sheinerman et al. Aging (Albany N.Y.). 2012; 5: 925-938; International Pat. Publ. Nos. WO2012/145363 and WO2011/057003).

MicroRNAs (miRNAs) are a class of non-coding RNAs whose final product is an approximately 22 nt functional RNA molecule. They play important roles in the regulation of target genes by binding to complementary regions of messenger transcripts to repress their translation or regulate degradation (Griffiths-Jones Nucleic Acids Research. 2006; 34, Database issue: D140-D144). Frequently, one miRNA can target multiple mRNAs and one mRNA can be regulated by multiple miRNAs targeting different regions of the 3' UTR. Once bound to an mRNA, miRNA can modulate gene expression and protein production by affecting, e.g., mRNA translation and stability (Baek et al. Nature. 2008; 455:64; Selbach et al. Nature. 2008; 455:58; Ambros. Nature. 2004;

431: 350-355; Bartel. Cell. 2004; 116: 281-297; Cullen. Virus Research. 2004; 102: 3-9; He et al. Nat. Rev. Genet. 2004; 5: 522-531; and Ying et al. Gene. 2004; 342: 25-28). There are other classes of less characterized small RNAs (reviewed in Kim. Mol. Cells. 2005; 19: 1-15).

Many of miRNAs are specific to or over-expressed in certain organs/tissues/cells (see, e.g., Hua et al. BMC Genomics. 2009; 10:214; Liang et al. BMC Genomics. 2007; 8:166; Landgraf et al. Cell. 2007; 129:1401-1414; Lee et al. RNA. 2008; 14:35-42) and in different brain areas, such as hippocampus, midbrain, frontal cortex, pituitary gland, and in different cell types, such as neurons and glial cells (Sempere et al. Genome Biol. 2004; 5: R13; Deo et al. Dev. Din. 2006; 235:2538-2548; Bak et al. RNA. 2008; 14: 432-444; Trivedi and Ramakrishna Int. J. Neurosci. 2009; 119: 1995-2016; Weng et al. Biomed. Res. 2011; 32: 135-141; He et al. Neuron. 2012; 73: 35-48).

Some miRNAs, including those that are cell-specific, are enriched in certain cellular compartments, particularly in axons, dendrites and synapses (see, e.g., Schratt et al. Nature. 2006; 439:283-289; Lugli et al. J. Neurochem. 2008; 106:650-661; Bicker and Schratt. J. Cell. Mol. Med. 2008; 12:1466-1476; Smalheiser and Lugli. Neuromolecular Med. 2009; 11:133-140; Rajasethupathy. Neuron. 2009; 63:714-716; Kye. RNA. 2007; 13:1224-1234; Yu et al. Exp Cell Res. 2008; 314:2618-2633; Cougot et al. J. Neurosci. 2008; 28:13793-13804; Kawahara. Brain Nerve. 2008. 60:1437-1444; Schratt G. Rev Neurosci. 2009; 10:842-849; Pichardo-Casas et al. Brain Research. 2012; 1436:20-33).

Expression and concentrations of miRNAs are regulated by various physiological and pathological signals. Changes in expression of some miRNAs were found in neurons of Parkinson's, Alzheimer's and other neurodegenerative disease patients (Hébert and De Strooper. Trends Neurosci. 2009; 32:199-206; Saba et al. PLoS One. 2008; 3:e3652; Kocerha et al. Neuromolecular Med. 2009; 11:162-172; Sethi and Lukiw. Neurosci Lett. 2009; 459:100-104; Zeng; Mol Pharmacol. 2009; 75:259-264; Cogswell et al. Journal of Alzheimer's disease. 2008; 14: 27-41; Schaefer et al. J. Exp. Med. 2007; 204:1553-1558; Hebert. Proc. Natl. Acad. Sci. USA. 2008; 105:6415-6420; Wang et al. J. Neurosci. 2008; 28:1213-1223; Nelson et al. Brain Pathol. 2008; 18:130-138; Lukiw. Neuroreport. 2007; 18:297-300).

Investigations of the miRNA involvement in Parkinson's disease (PD) have focused on analysis of miRNA expression in the midbrain and of miRNA role in functioning of dopaminergic neurons and the α-synuclein synthesis. Downregulation of miR-133b in midbrain of PD patients (Kim et al. Science. 2007; 317: 1220-1224) as well as in mouse models of PD has been reported in several studies (reviews: Filatova et al. Biochemistry (Mosc). 2012; 77: 813-819; Harraz et al. J. Chem. Neuroanat. 2011; 42: 127-130; Mouradian. Neurobiol Dis. 2012; 46: 279-284). miR-7 and miR-153 have been found to down-regulate synthesis of α-synuclein (Doxakis. J. Biol. Chem. 2010; 285:12726-12734; Junn et al. Proc. Natl. Acad. Sci. USA. 2009; 106: 13052-13057). Due to their small size, miRNAs can cross the blood-brain, placental and kidney barriers. Analysis of cell/tissue-specific miRNAs in bodily fluids was proposed for detection of in vivo cell death (U.S. Patent Pub. No 20090081640; Laterza et al. Clin. Chem. 2009; 55:1977-1983).

For the use of miRNA in diagnostics, it is also important that miRNA secretion varies depending on cellular physiology (Palma et al. Nucleic Acids Res. 2012; 40:9125-9138; Pigati et al. PLoS One. 2010; 5: e13515). In addition to miRNA release into extracellular space and subsequent appearance in the bodily fluids due to cell death, miRNA appear in circulation due to blebbing of apoptotic bodies, budding and shedding of microvesicles, active secretion in the form of exosomes and of miRNA complexes with proteins (AGO2, NPM1 and others) and high density lipoproteins (HDL) (reviews: Sun et al. Clin. Chem. Lab. Med. 2012; 50: 2121-2126; Zandberga et al. Genes Chromosomes Cancer. 2013; 52: 356-369). All these forms of cell-free miRNA are highly stable in the bloodstream and other bodily fluids. The secretion of miRNA is selective and can be significantly changed by various pathological processes. For example, changes in the spectrum of miRNA secreted in exosomes from prion-infected neuronal cells, as compared to uninfected cells, have been demonstrated (Belingham et al. Nucleic Acids Res. 2012; 40: 10937-10949).

Two approaches are widely used for searching miRNA biomarkers of various diseases in bodily fluids:

1. Measurement of hundreds of different miRNA in a bodily fluid from patients with a pathology of interest and from control subjects using miRNA array or next generation sequencing (NGS) (Qin et al. Cancer Inform. 2013; 12: 83-101). While this approach allows to analyze a huge numbers of various miRNA, currently the miRNA array-based and sequencing techniques are not sufficiently sensitive to detect many miRNA whose concentration in bodily fluids is relatively low. As a consequence, most of the miRNA detectable in bodily fluids by arrays and NGS are ubiquitous miRNA expressed in all or many tissues, and many of them derive from blood cells (Pritchard et al. Cancer Prev. Res. (Phila). 2012; 5:492-497; Leidner and Thompson. PLoS One. 2013; 8: 57841). The detection of changes in the concentrations of such ubiquitous miRNA in patients with one pathology does not mean that the same miRNA cannot be involved in other diseases of different organs. Many miRNA are associated with a particular pathology type, such as cancer, inflammation, hypoxia, etc., and changes in their concentration in bodily fluids can be associated with diseases of different organs. For example, changes of miR-155 concentrations were found in the bloodstream of patients with breast, esophageal, lung, pancreatic cancers and lymphomas (Blair and Yan. DNA Cell Biol. 2012; 31 Suppl. 1: S49-61; Xie et al. Bioinformatics. 2013; 29: 638-644). Level of miR-21 increases in plasma/serum of patients with osteosarcoma, bladder, esophageal, gastric, lung, breast, colorectal cancers, neck squamous cell carcinoma and other tumors (Blair and Yan. DNA Cell Biol. 2012; 31 Suppl. 1: S49-61; Farazi et al. J. Pathol. 2011; 223: 102-115; Xie et al, Bioinformatics. 2013; 29: 638-644). It follows that the potential biomarkers found by miRNA arrays should be also tested in other pathologies, not only in healthy control subjects.

2. The second approach is based on analysis of disease-specific miRNAs identified by comparison of miRNAs isolated from pathologic and normal tissue, organ or cell type. Here, subsequent to identification of disease-specific miRNAs (e.g., by an array followed by RT-PCR), their presence in bodily fluids is analyzed. In this strategy, since a limited number of circulating miRNAs is tested, the use of individual RT-PCR is possible which allows to increase sensitivity and reproducibility of the analysis. However, in many cases when this method was applied, no correlation was detected between miRNA concentration and pathology-induced changes in the tissue and in bodily fluids (Boeri et al., Proc. Natl. Acad. Sci. USA. 2011; 108: 3713-3718; Cuk et al. Int. J. Cancer. 2013; 132: 1602-1612).

SUMMARY OF THE INVENTION

As outlined in the Background section, above, despite recent advances, there is a great need in the art in sensitive methods of early detection of neurodegenerative diseases such as Parkinson's disease (PD). The present invention addresses this and other needs by providing methods for early diagnosis, progression and treatment monitoring of PD and its differentiation from other neurodegenerative diseases by quantifying brain-enriched miRNAs in bodily fluids.

In one aspect, the invention provides a method for detecting a first neurodegenerative disease in a subject, which method comprises:
a) measuring the level of a first brain-enriched miRNA in a bodily fluid sample collected from the subject, wherein said first brain-enriched miRNA is enriched in a brain area(s) affected by the first neurodegenerative disease;
b) measuring the level of a second brain-enriched miRNA in the same bodily fluid sample collected from the subject, wherein said second brain-enriched miRNA (i) is enriched in a brain area(s) which is not affected by the first neurodegenerative disease, or (ii) is enriched in a brain cell type which is not affected by the first neurodegenerative disease, or (iii) is enriched in the same brain area as the first miRNA, but its expression and/or secretion change differently than expression and/or secretion of the first miRNA during development of the first neurodegenerative disease;
c) calculating the ratio of the levels of the miRNAs measured in steps (a) and (b);
d) comparing the ratio of the levels of the miRNAs calculated in step (c) with a corresponding control ratio, and
e) (i) identifying the subject as being afflicted with the first neurodegenerative disease when the ratio of the levels of the miRNAs calculated in step (c) is higher than the corresponding control ratio or (ii) identifying the subject as not being afflicted with the first neurodegenerative disease when the ratio of the levels of the miRNA calculated in step (c) is not higher than the corresponding control ratio.

In a related aspect, the invention provides a method for detecting a first neurodegenerative disease in a subject, which method comprises:
a) measuring the level of a first miRNA in a bodily fluid sample collected from the subject, wherein said first miRNA (i) is enriched in a brain area(s) affected by the first neurodegenerative disease or (ii) is an inflammation-associated miRNA;
b) measuring the level of a second miRNA in the same bodily fluid sample collected from the subject, wherein said second miRNA (i) is an inflammation-associated miRNA if the first miRNA is a brain-enriched miRNA or (ii) is a brain-enriched miRNA if the first miRNA is an inflammation-associated miRNA;
c) calculating the ratio of the levels of the miRNAs measured in steps (a) and (b);
d) comparing the ratio of the levels of the miRNAs calculated in step (c) with a corresponding control ratio, and
e) (i) identifying the subject as being afflicted with the first neurodegenerative disease when the ratio of the levels of the miRNAs calculated in step (c) is higher than the corresponding control ratio or (ii) identifying the subject as not being afflicted with the first neurodegenerative disease when the ratio of the levels of the miRNA calculated in step (c) is not higher than the corresponding control ratio.

In one embodiment of the above two methods, the method further comprises refining the diagnosis by the following steps, which steps can be performed simultaneously or sequentially with each other and/or with the steps (d)-(e) of the above two methods:

f) comparing the ratio of the levels of the miRNAs calculated in step (c) with the standard range of ratios of said miRNAs characteristic of a second neurodegenerative disease, and
g) (i) excluding the diagnosis of the second neurodegenerative disease in the subject if the ratio of the levels of the miRNAs calculated in step (c) does not fall within the standard range of ratios of said miRNAs characteristic of the second neurodegenerative disease, or (ii) not excluding the diagnosis of the second neurodegenerative disease in the subject if the ratio of the levels of the miRNAs calculated in step (c) falls within the standard range of ratios of said miRNAs characteristic of the second neurodegenerative disease.

In one embodiment of the above two methods, the method further comprises refining the diagnosis by the following steps, which steps can be performed simultaneously or sequentially with each other and/or with the steps (a)-(e) of the above two methods:
f) measuring the level of a third brain-enriched miRNA in the same bodily fluid sample collected from the subject, wherein said third brain-enriched miRNA is enriched in a brain area(s) affected by a second neurodegenerative disease;
g) measuring the level of a fourth brain-enriched miRNA in the same bodily fluid sample collected from the subject, wherein said fourth brain-enriched miRNA is (i) enriched in a brain area(s) which is not affected by the second neurodegenerative disease, or (ii) is enriched in a brain cell type which is not affected by the second neurodegenerative disease, or (iii) is enriched in the same brain area as the third miRNA, but its expression and/or secretion change differently than expression and/or secretion of the third miRNA during development of the second neurodegenerative disease;
h) calculating the ratio of the levels of the miRNAs measured in steps (f) and (g);
i) comparing the ratio of the levels of the miRNAs calculated in step (h) with the standard range of ratios of said miRNAs characteristic of the second neurodegenerative disease;
j) (i) identifying the subject as being afflicted with the second neurodegenerative disease in addition to the first neurodegenerative disease if the ratio of the levels of the miRNAs calculated in step (h) falls within the standard range of ratios of said miRNAs characteristic of the second neurodegenerative disease, or (ii) excluding the diagnosis of the second neurodegenerative disease in the subject if the ratio of the levels of the miRNAs calculated in step (h) does not fall within the standard range of ratios of said miRNAs characteristic of the second neurodegenerative disease.

In one embodiment of any of the above methods, said first neurodegenerative disease is Parkinson's disease (PD).

In one embodiment of the above disease differentiation methods, said first neurodegenerative disease is Parkinson's disease (PD) and said second neurodegenerative disease is selected from the group consisting of Alzheimer's disease (AD), Mild Cognitive Impairment (MCI), Huntington's disease (HD), prion-caused diseases, frontotemporal dementia (FTD), Lewy body dementia, vascular dementias, Amyotrophic Later Sclerosis (ALS), chronic traumatic encephalopathy (CTE), progressive supranuclear palsy (PSP), multiple system atrophy (MSA), corticobasal degeneration (CBGD), Pick's disease, and olivopontocerebellar atrophy (OPCA).

In one aspect, the invention provides a method for detecting Parkinson's disease (PD) in a subject, which method comprises:

a) measuring the level of a first brain-enriched miRNA in a bodily fluid sample collected from the subject, wherein said first brain-enriched miRNA is neuronal miRNA enriched in midbrain and/or frontal cortex;

b) measuring the level of a second brain-enriched miRNA in the same bodily fluid sample collected from the subject, wherein said second brain-enriched miRNA is (i) enriched in a brain area(s) which is not affected by PD, or (ii) is enriched in a brain cell type which is not affected by PD, or (iii) is enriched in the same brain area as the first miRNA, but its expression and/or secretion change differently than expression and/or secretion of the first miRNA during PD development;

c) calculating the ratio of the levels of the miRNA measured in steps (a) and (b);

d) comparing the ratio of the levels of the miRNA calculated in step (c) with a corresponding control ratio, and e) (i) identifying the subject as being afflicted with PD when the ratio of the levels of the miRNA calculated in step (c) is higher than the corresponding control ratio or (ii) identifying the subject as not being afflicted with PD when the ratio of the levels of the miRNA calculated in step (c) is not higher than the corresponding control ratio.

In a related aspect, the invention provides a method for detecting Parkinson's disease (PD) in a subject, which method comprises:

a) measuring the level of a first miRNA in a bodily fluid sample collected from the subject, wherein said first miRNA is (i) a brain-enriched neuronal miRNA enriched in midbrain and/or frontal cortex or is (ii) an inflammation-associated miRNA;

b) measuring the level of a second miRNA in the same bodily fluid sample collected from the subject, wherein said second miRNA is (i) an inflammation-associated miRNA if the first miRNA is a brain-enriched miRNA or is (ii) a brain-enriched miRNA if the first miRNA is an inflammation-associated miRNA;

c) calculating the ratio of the levels of the miRNA measured in steps (a) and (b);

d) comparing the ratio of the levels of the miRNA calculated in step (c) with a corresponding control ratio, and e) (i) identifying the subject as being afflicted with PD when the ratio of the levels of the miRNA calculated in step (c) is higher than the corresponding control ratio or (ii) identifying the subject as not being afflicted with PD when the ratio of the levels of the miRNA calculated in step (c) is not higher than the corresponding control ratio.

In one embodiment of the above two methods for detecting PD, the method further comprises refining the diagnosis by the following steps, which steps can be performed simultaneously or sequentially with each other and with the steps (d)-(e) of the above two methods for detecting PD:

f) comparing the ratio of the levels of the miRNAs calculated in step (c) with the standard range of ratios of said miRNAs characteristic of a second neurodegenerative disease different from PD;

g) (i) excluding the diagnosis of the second neurodegenerative disease in the subject if the ratio of the levels of the miRNAs calculated in step (c) does not fall within the standard range of ratios of said miRNAs characteristic of the second neurodegenerative disease, or (ii) not excluding the diagnosis of the second neurodegenerative disease if the ratio of the levels of the miRNAs calculated in step (c) falls within the standard range of ratios of said miRNAs characteristic of the second neurodegenerative disease.

In one embodiment of the above two methods for detecting PD, the method further comprises refining the diagnosis by the following steps, which steps can be performed simultaneously or sequentially with each other and with the steps (a)-(e) of the above two methods for detecting PD:

f) measuring the level of a third brain-enriched miRNA in the same bodily fluid sample collected from the subject, wherein said third brain-enriched miRNA is enriched in a brain area(s) affected by a second neurodegenerative disease and is a pre-identified numerator in biomarker miRNA pair for said second neurodegenerative disease;

g) measuring the level of a fourth brain-enriched miRNA in the same bodily fluid sample collected from the subject, wherein said fourth brain-enriched miRNA is and is a pre-identified denominator in biomarker miRNA pair for said second neurodegenerative disease and is (i) enriched in a brain area(s) which is not affected by the second neurodegenerative disease, or (ii) is enriched in a brain cell type which is not affected by the second neurodegenerative disease and is different from the cell type where the third miRNA is enriched, or (iii) is enriched in the same brain area as the third miRNA, but its expression and/or secretion change differently than expression and/or secretion of the third miRNA during development of the second neurodegenerative disease;

h) calculating the ratio of the levels of the miRNAs measured in steps (f) and (g);

i) comparing the ratio of the levels of the miRNAs calculated in step (h) with the standard range of ratios of said miRNAs characteristic of the second neurodegenerative disease;

j) (i) identifying the subject as being afflicted with the second neurodegenerative disease in addition to PD if the ratio of the levels of the miRNAs calculated in step (h) falls within the standard range of ratios of said miRNAs characteristic of the second neurodegenerative disease, or (ii) excluding the diagnosis of the second neurodegenerative disease in the subject if the ratio of the levels of the miRNAs calculated in step (h) does not fall within the standard range of ratios of said miRNAs characteristic of the second neurodegenerative disease.

In one embodiment of any of the above methods of disease detection, the control ratio is a predetermined value which represents a statistically validated threshold ratio of the levels of said first and second miRNAs (a single "cut-off" value) equal to the highest possible value within the range of corresponding values in age-matched healthy subjects. In another embodiment of any of the above methods of disease detection, the control ratio is the ratio of the levels of said first and second miRNAs in a similarly processed bodily fluid sample from the same subject collected in the past.

In one embodiment of any of the above methods of disease differentiation, the standard range of ratios of miRNAs characteristic of the second neurodegenerative disease is a statistically validated predetermined range of values established by determining the ratios of the same miRNAs in a large cohort of subjects diagnosed with the second neurodegenerative disease. In one specific embodiment, the cohort of subjects diagnosed with the second neurodegenerative disease represents a full range of development stages of said second neurodegenerative disease. In another specific embodiment, the cohort of subjects diagnosed with the second neurodegenerative disease represents one or more development stages of said second neurodegenerative disease.

In one embodiment of any of the above methods of disease differentiation, said second neurodegenerative disease is selected from the group consisting of Alzheimer's disease (AD), Mild Cognitive Impairment (MCI), Huntington's disease (HD), prion-caused diseases, frontotemporal dementia (FTD), Lewy body dementia, vascular dementias, Amyotrophic Later Sclerosis (ALS), chronic traumatic encephalopathy (CTE), progressive supranuclear palsy (PSP), multiple system atrophy (MSA), corticobasal degeneration (CBGD), Pick's disease, and olivopontocerebellar atrophy (OPCA).

In another aspect, the invention provides a method for monitoring changes in development of a neurodegenerative disease in a subject (e.g., a subject who had been previously diagnosed with said neurodegenerative disease), which method comprises:
a) measuring the level of a first brain-enriched miRNA in two or more bodily fluid samples collected from the subject, wherein said first brain-enriched miRNA is enriched in a brain area(s) affected by the neurodegenerative disease;
b) measuring the level of a second brain-enriched miRNA in the same bodily fluids samples as in step (a), wherein said second brain-enriched miRNA (i) is enriched in a brain area(s) which is not affected by the neurodegenerative disease, or (ii) is enriched in a brain cell type which is not affected by the neurodegenerative disease, or (iii) is enriched in the same brain area as the first miRNA, but its expression and/or secretion change differently than expression and/or secretion of the first miRNA during development of the neurodegenerative disease;
c) calculating the ratio of the levels of the miRNA measured in steps (a) and (b) for each bodily fluid sample;
d) comparing the ratios of the levels of the miRNA calculated in step (c) between the earlier collected and later collected bodily fluid sample(s), and
e) (i) determining that the neurodegenerative disease in the subject has progressed if the ratio of the levels of the miRNA calculated in step (c) is increased in the later collected bodily fluid sample(s) as compared to the earlier collected sample(s), or (ii) determining that the neurodegenerative disease in the subject has not progressed if the ratio of the levels of the miRNA calculated in step (c) is not changed in the later collected bodily fluid sample(s) as compared to the earlier collected sample(s).

In a related aspect, the invention provides a method for monitoring changes in development of a neurodegenerative disease in a subject (e.g., a subject who had been previously diagnosed with said neurodegenerative disease), which method comprises:
a) measuring the level of a first miRNA in two or more bodily fluid samples collected from the subject, wherein said first miRNA (i) is enriched in a brain area(s) affected by the first neurodegenerative disease or (ii) is an inflammation-associated miRNA;
b) measuring the level of a second miRNA in the same bodily fluids samples as in step (a), wherein said second miRNA (i) is an inflammation-associated miRNA if the first miRNA is a brain-enriched miRNA or (ii) is a brain-enriched miRNA if the first miRNA is an inflammation-associated miRNA;
c) calculating the ratio of the levels of the miRNA measured in steps (a) and (b) for each bodily fluid sample;
d) comparing the ratios of the levels of the miRNA calculated in step (c) between the earlier collected and later collected bodily fluid sample(s), and
e) (i) determining that the neurodegenerative disease in the subject has progressed if the ratio of the levels of the miRNA calculated in step (c) is increased in the later collected bodily fluid sample(s) as compared to the earlier collected sample(s), or (ii) determining that the neurodegenerative disease in the subject has not progressed if the ratio of the levels of the miRNA calculated in step (c) is not changed in the later collected bodily fluid sample(s) as compared to the earlier collected sample(s).

In a related aspect, the invention provides a method for monitoring changes in development of Parkinson's disease (PD) in a subject (e.g., a subject who had been previously diagnosed with PD), which method comprises:
a) measuring the level of a first brain-enriched miRNA in two or more bodily fluid samples collected from the subject, wherein the samples have been collected at spaced apart time points, and wherein said first brain-enriched miRNA is enriched in midbrain and/or frontal cortex;
b) measuring the level of a second brain-enriched miRNA in the same bodily fluid samples as in step (a), wherein said second brain-enriched miRNA is (i) enriched in brain areas which are not affected by PD, or (ii) is enriched in a brain cell type which is not affected by PD, or (iii) is enriched in the same brain area as the first brain-enriched miRNA, but its expression and/or secretion change differently than expression and/or secretion of the first brain-enriched miRNA during PD development;
c) calculating the ratio of the levels of the miRNA measured in steps (a) and (b) for each bodily fluid sample;
d) comparing the ratios of the levels of the miRNA calculated in step (c) between the earlier collected and later collected bodily fluid sample(s), and
e) (i) determining that PD in the subject has progressed if the ratio of the levels of the miRNA calculated in step (c) is increased in the later collected bodily fluid sample(s) as compared to the earlier collected sample(s), or (ii) determining that PD in the subject has not progressed if the ratio of the levels of the miRNA calculated in step (c) is not changed in the later collected bodily fluid sample(s) as compared to the earlier collected sample(s).

In another related aspect, the invention provides a method for monitoring changes in development of Parkinson's disease (PD) in a subject (e.g., a subject who had been previously diagnosed with PD), which method comprises:
a) measuring the level of a first miRNA in two or more bodily fluid samples collected from the subject, wherein the samples have been collected at spaced apart time points, and wherein said first miRNA is (i) a brain-enriched neuronal miRNA enriched in midbrain and/or frontal cortex or is (ii) an inflammation-associated miRNA;
b) measuring the level of a second miRNA in the same bodily fluid samples as in step (a), wherein said second miRNA is (i) an inflammation-associated miRNA if the first miRNA is a brain-enriched miRNA or is (ii) a brain-enriched miRNA if the first miRNA is an inflammation-associated miRNA;
c) calculating the ratio of the levels of the miRNA measured in steps (a) and (b) for each bodily fluid sample;
d) comparing the ratios of the levels of the miRNA calculated in step (c) between the earlier collected and later collected bodily fluid sample(s), and
e) (i) determining that PD in the subject has progressed if the ratio of the levels of the miRNA calculated in step (c) is increased in the later collected bodily fluid sample(s) as compared to the earlier collected sample(s), or (ii) determining that PD in the subject has not progressed if the ratio of the levels of the miRNA calculated in step (c) is not changed in the later collected bodily fluid sample(s) as compared to the earlier collected sample(s).

In a separate aspect, the invention provides a method for monitoring the effect of a treatment on development of a neurodegenerative disease in a subject who had been previously diagnosed with said neurodegenerative disease, which method comprises:

a) measuring the level of a first brain-enriched miRNA in a bodily fluid sample collected from the subject prior to initiation of the treatment, wherein said first brain-enriched miRNA is enriched in a brain area(s) affected by the neurodegenerative disease;

b) measuring the level of a second brain-enriched miRNA in the same bodily fluid sample collected from the subject, wherein said second brain-enriched miRNA (i) is enriched in a brain area(s) which is not affected by the neurodegenerative disease, or (ii) is enriched in a brain cell type which is not affected by the neurodegenerative disease, or (iii) is enriched in the same brain area as the first miRNA, but its expression and/or secretion change differently than expression and/or secretion of the first miRNA during development of the neurodegenerative disease;

c) calculating the ratio of the levels of the miRNA measured in steps (a) and (b);

d) measuring the level of the same first miRNA as in step (a) in one or more bodily fluid sample(s) collected from the subject in the course of or following the treatment;

e) measuring the level of the same second miRNA as in step (b) in the same bodily fluid sample(s) as in step (d);

f) calculating the ratio of the levels of the miRNA measured in steps (d) and (e) for each bodily fluid sample;

g) comparing the ratios of the levels of the miRNA calculated in steps (c) and (f), and optionally comparing the ratios of the levels of the miRNA calculated in step (f) between different samples in step (d), and h) (i) determining that the treatment is effective for said neurodegenerative disease if the ratio of the levels of the miRNA calculated in step (c) is higher than the corresponding ratio(s) calculated in step (f), or (ii) determining that the treatment is not effective for said neurodegenerative disease if the ratio of the levels of the miRNA calculated in step (c) is not higher than the corresponding ratio(s) calculated in step (f).

In a related aspect, the invention provides a method for monitoring the effect of a treatment on development of a neurodegenerative disease in a subject who had been previously diagnosed with said neurodegenerative disease, which method comprises:

a) measuring the level of a first miRNA in a bodily fluid sample collected from the subject prior to initiation of the treatment, wherein said first miRNA (i) is enriched in a brain area(s) affected by the first neurodegenerative disease or (ii) is an inflammation-associated miRNA;

b) measuring the level of a second miRNA in the same bodily fluid sample collected from the subject, wherein said second miRNA (i) is an inflammation-associated miRNA if the first miRNA is a brain-enriched miRNA or (ii) is a brain-enriched miRNA if the first miRNA is an inflammation-associated miRNA;

c) calculating the ratio of the levels of the miRNA measured in steps (a) and (b);

d) measuring the level of the same first miRNA as in step (a) in one or more bodily fluid sample(s) collected from the subject in the course of or following the treatment;

e) measuring the level of the same second miRNA as in step (b) in the same bodily fluid sample(s) as in step (d);

f) calculating the ratio of the levels of the miRNA measured in steps (d) and (e) for each bodily fluid sample;

g) comparing the ratios of the levels of the miRNA calculated in steps (c) and (f), and optionally comparing the ratios of the levels of the miRNA calculated in step (f) between different samples in step (d), and h) (i) determining that the treatment is effective for said neurodegenerative disease if the ratio of the levels of the miRNA calculated in step (c) is higher than the corresponding ratio(s) calculated in step (f), or (ii) determining that the treatment is not effective for said neurodegenerative disease if the ratio of the levels of the miRNA calculated in step (c) is not higher than the corresponding ratio(s) calculated in step (f).

In another related aspect, the invention provides a method for monitoring the effect of a treatment on development of Parkinson's disease (PD) in a subject who had been previously diagnosed with PD, which method comprises:

a) measuring the level of a first brain-enriched miRNA in a bodily fluid sample collected from the subject prior to initiation of the treatment, wherein said first miRNA is enriched in midbrain and/or frontal cortex;

b) measuring the level of a second brain-enriched miRNA in the same bodily fluid sample collected from the subject, wherein said second miRNA is (i) enriched in brain areas which are not affected by PD, or (ii) is enriched in a brain cell type which is not affected by PD, or (iii) is enriched in the same brain area as the first miRNA, but its expression and/or secretion change differently than expression and/or secretion of the first miRNA during PD development;

c) calculating the ratio of the levels of the miRNA measured in steps (a) and (b);

d) measuring the level of the same first miRNA as in step (a) in one or more bodily fluid sample(s) collected from the subject in the course of or following the treatment;

e) measuring the level of the same second miRNA as in step (b) in the same bodily fluid sample(s) as in step (d);

f) calculating the ratio of the levels of the miRNA measured in steps (d) and (e) for each bodily fluid sample;

g) comparing the ratios of the levels of the miRNA calculated in steps (c) and (f), and optionally comparing the ratios of the levels of the miRNA calculated in step (f) between different samples in step (d), and h) (i) determining that the PD treatment is effective if the ratio of the levels of the miRNA calculated in step (c) is higher than the corresponding ratio(s) calculated in step (f), or (ii) determining that the PD treatment is not effective if the ratio of the levels of the miRNA calculated in step (c) is not higher than the corresponding ratio(s) calculated in step (f).

In yet another related aspect, the invention provides a method for monitoring the effect of a treatment on development of Parkinson's disease (PD) in a subject who had been previously diagnosed with PD, which method comprises:

a) measuring the level of a first miRNA in a bodily fluid sample collected from the subject prior to initiation of the treatment, wherein said first miRNA is (i) a brain-enriched neuronal miRNA enriched in midbrain and/or frontal cortex or is (ii) an inflammation-associated miRNA;

b) measuring the level of a second miRNA in the same bodily fluid sample collected from the subject, wherein said second miRNA is (i) an inflammation-associated miRNA if the first miRNA is a brain-enriched miRNA or is (ii) a brain-enriched miRNA if the first miRNA is an inflammation-associated miRNA;

c) calculating the ratio of the levels of the miRNA measured in steps (a) and (b);

d) measuring the level of the same first miRNA as in step (a) in one or more bodily fluid sample(s) collected from the subject in the course of or following the treatment;

e) measuring the level of the same second miRNA as in step (b) in the same bodily fluid sample(s) as in step (d);
f) calculating the ratio of the levels of the miRNA measured in steps (d) and (e) for each bodily fluid sample;
g) comparing the ratios of the levels of the miRNA calculated in steps (c) and (f), and optionally comparing the ratios of the levels of the miRNA calculated in step (f) between different samples in step (d), and
h) (i) determining that the PD treatment is effective if the ratio of the levels of the miRNA calculated in step (c) is higher than the corresponding ratio(s) calculated in step (f), or (ii) determining that the PD treatment is not effective if the ratio of the levels of the miRNA calculated in step (c) is not higher than the corresponding ratio(s) calculated in step (f).

In a separate aspect, the invention provides a method for identifying a compound useful for slowing down the progression or treating a neurodegenerative disease in a subject who had been previously diagnosed with said neurodegenerative disease, which method comprises:
a) measuring the level of a first brain-enriched miRNA in a bodily fluid sample, wherein said bodily fluid sample(s) is collected from the subject prior to test compound administration, and wherein said first brain-enriched miRNA is enriched in a brain area(s) affected by the neurodegenerative disease;
b) measuring the level of a second brain-enriched miRNA in the same bodily fluid sample collected from the subject, wherein said second brain-enriched miRNA (i) is enriched in a brain area(s) which is not affected by the neurodegenerative disease, or (ii) is enriched in a brain cell type which is not affected by the neurodegenerative disease, or (iii) is enriched in the same brain area as the first miRNA, but its expression and/or secretion change differently than expression and/or secretion of the first miRNA during development of the neurodegenerative disease;
c) calculating the ratio of the levels of the miRNA measured in steps (a) and (b);
d) measuring the level of the same first miRNA as in step (a) in one or more bodily fluid samples collected from the subject following administration of a test compound;
e) measuring the level of the same second miRNA as in step (b) in the same bodily fluid sample(s) as in step (d);
f) calculating the ratio of the levels of the miRNAs measured in steps (d) and (e) for each of the bodily fluid samples collected from the subject following administration of the test compound;
g) comparing the ratio of the levels of the miRNA calculated in steps (c) and (f), and
h) (i) identifying that the test compound is useful for slowing down the progression or treating the neurodegenerative disease if the ratio of the levels of the miRNA calculated in step (f) is lower than the ratio of the levels of the miRNA calculated in step (c); (ii) identifying that the test compound is not useful for slowing down the progression or treating the neurodegenerative disease if the ratio of the levels of the miRNA calculated in step (f) is not lower than the ratio of the levels of the miRNAs calculated in step (c).

In a related aspect, the invention provides a method for identifying a compound useful for slowing down the progression or treating a neurodegenerative disease in a subject who had been previously diagnosed with said neurodegenerative disease, which method comprises:
a) measuring the level of a first miRNA in a bodily fluid sample, wherein said bodily fluid sample(s) is collected from the subject prior to test compound administration, and wherein said first miRNA (i) is enriched in a brain area(s) affected by the first neurodegenerative disease or (ii) is an inflammation-associated miRNA;
b) measuring the level of a second miRNA in the same bodily fluid sample collected from the subject, wherein said second miRNA (i) is an inflammation-associated miRNA if the first miRNA is a brain-enriched miRNA or (ii) is a brain-enriched miRNA if the first miRNA is an inflammation-associated miRNA;
c) calculating the ratio of the levels of the miRNA measured in steps (a) and (b);
d) measuring the level of the same first miRNA as in step (a) in one or more bodily fluid samples collected from the subject following administration of a test compound;
e) measuring the level of the same second miRNA as in step (b) in the same bodily fluid sample(s) as in step (d);
f) calculating the ratio of the levels of the miRNAs measured in steps (d) and (e) for each of the bodily fluid samples collected from the subject following administration of the test compound;
g) comparing the ratio of the levels of the miRNA calculated in steps (c) and (f), and
h) (i) identifying that the test compound is useful for slowing down the progression or treating the neurodegenerative disease if the ratio of the levels of the miRNA calculated in step (f) is lower than the ratio of the levels of the miRNA calculated in step (c); (ii) identifying that the test compound is not useful for slowing down the progression or treating the neurodegenerative disease if the ratio of the levels of the miRNA calculated in step (f) is not lower than the ratio of the levels of the miRNAs calculated in step (c).

In another related aspect, the invention provides a method for identifying a compound useful for slowing down the progression or treating Parkinson's disease (PD) in a subject who had been previously diagnosed with PD, which method comprises:
a) measuring the level of a first brain-enriched miRNA in a bodily fluid sample, wherein said bodily fluid sample(s) is collected from the subject prior to test compound administration, and wherein said first miRNA is enriched in midbrain and/or frontal cortex;
b) measuring the level of a second brain-enriched miRNA in the same bodily fluid sample collected from the subject, wherein said second miRNA is (i) enriched in brain areas which are not affected by PD, or (ii) is enriched in a brain cell type which is not affected by PD, or (iii) is enriched in the same brain area as the first miRNA, but its expression and/or secretion change differently than expression and/or secretion of the first miRNA during PD development;
c) calculating the ratio of the levels of the miRNA measured in steps (a) and (b);
d) measuring the level of the same first miRNA as in step (a) in one or more bodily fluid samples collected from the subject following administration of a test compound;
e) measuring the level of the same second miRNA as in step (b) in the same bodily fluid sample(s) as in step (d);
f) calculating the ratio of the levels of the miRNAs measured in steps (d) and (e) for each of the bodily fluid samples collected from the subject following administration of the test compound;
g) comparing the ratio of the levels of the miRNA calculated in steps (c) and (f), and
h) (i) identifying that the test compound is useful for slowing down the progression or treating PD if the ratio of the levels of the miRNA calculated in step (f) is lower than the ratio of the levels of the miRNA calculated in step (c); (ii) identifying that the test compound is not useful for slowing down the progression or treating PD if the ratio of the levels of the miRNA calculated in step (f) is not lower than the ratio of the levels of the miRNAs calculated in step (c).

In yet another related aspect, the invention provides a method for identifying a compound useful for slowing down the progression or treating Parkinson's disease (PD) in a subject who had been previously diagnosed with PD, which method comprises:

a) measuring the level of a first miRNA in a bodily fluid sample, wherein said bodily fluid sample(s) is collected from the subject prior to test compound administration, and wherein said first miRNA is (i) a brain-enriched neuronal miRNA enriched in midbrain and/or frontal cortex or is (ii) an inflammation-associated miRNA;
b) measuring the level of a second miRNA in the same bodily fluid sample collected from the subject, wherein said second miRNA is (i) an inflammation-associated miRNA if the first miRNA is a brain-enriched miRNA or is (ii) a brain-enriched miRNA if the first miRNA is an inflammation-associated miRNA;
c) calculating the ratio of the levels of the miRNA measured in steps (a) and (b);
d) measuring the level of the same first miRNA as in step (a) in one or more bodily fluid samples collected from the subject following administration of a test compound;
e) measuring the level of the same second miRNA as in step (b) in the same bodily fluid sample(s) as in step (d);
f) calculating the ratio of the levels of the miRNAs measured in steps (d) and (e) for each of the bodily fluid samples collected from the subject following administration of the test compound;
g) comparing the ratio of the levels of the miRNA calculated in steps (c) and (f), and
h) (i) identifying that the test compound is useful for slowing down the progression or treating PD if the ratio of the levels of the miRNA calculated in step (f) is lower than the ratio of the levels of the miRNA calculated in step (c); (ii) identifying that the test compound is not useful for slowing down the progression or treating PD if the ratio of the levels of the miRNA calculated in step (f) is not lower than the ratio of the levels of the miRNAs calculated in step (c).

In one embodiment of any of the above methods, the neurodegenerative disease is Parkinson's disease (PD).

In one embodiment of any of the above methods, the first brain-enriched miRNA is a neuronal miRNA. In one embodiment of any of the above methods, the first brain-enriched miRNA is synapse and/or neurite miRNA.

In one embodiment of any of the above methods, the second miRNA is a brain-enriched miRNA, which (1) is enriched in a brain area(s) which is not affected by the first neurodegenerative disease (e.g., PD) or (2) is enriched in a brain cell type which is not affected by the first neurodegenerative disease (e.g., PD). In one embodiment of any of the above methods, the second miRNA is a brain-enriched miRNA selected from the group consisting of miRNAs which are mainly expressed in brain areas not involved in PD, miRNAs which are mainly expressed in glial cells, and brain-enriched miRNAs downregulated in PD.

In one embodiment of any of the above methods involving the first and second miRNAs which are brain-enriched, the first brain-enriched miRNA is enriched in neurons and the second brain-enriched miRNA is enriched in glial cells.

In one embodiment of any of the above methods involving the first and second miRNAs which are brain-enriched, the pair of the first miRNA and the second miRNA is selected from the group consisting of: let-7e/miR-335, miR-107/miR-335, miR-491-5p/miR-335, miR-744/miR-335, miR-99b/miR-335, let-7e/miR-9*, miR-491-5p/miR-9*, let-7e/miR-132, miR-107/miR-132, miR-491-5p/miR-132, let-7e/miR-134, miR-107/miR-134, miR-99b/miR-134, miR-491-5p/miR-134, let-7e/miR-323-3p, miR-107/miR-323-3p, miR-127/miR-323-3p, miR-181b/miR-323-3p, miR-99b/miR-323-3p, miR-491-5p/miR-323-3p, let-7e/miR-411, miR-107/miR-411, and miR-491-5p/miR-411.

In one embodiment of any of the above methods involving the first and second miRNAs one of which is brain-enriched and another inflammation-associated, the pair of the first miRNA and the second miRNA is selected from the group consisting of: miR-155/miR-335, let-7e/miR-146b, miR-491-5p/miR-146a, let-7e/miR-146a, miR-744/miR-146a, miR-155/miR-16, miR-155/miR-132, miR-155/miR-323-3p, miR-155/miR-411, miR-491-5p/miR-146b, miR-155/miR-146a, and miR-155/miR-146b.

In one embodiment of any of the above disease differentiation methods involving the first and second miRNAs which are brain-enriched, the pair of the first miRNA and the second miRNA is selected from the group consisting of: let-7e/miR-335, let-7e/miR-9*, miR-107/miR-335, miR-127/miR-323-3p, miR-491-5p/miR-335, miR-491-5p/miR-9*, miR-107/miR-9*, miR-744/miR-335, let-7e/miR-132, miR-107/miR-134, miR-181b/miR-132, let-7e/miR-210, miR-181b/miR-9*, miR-181a/miR-335, miR-491-5p/miR-134, let-7e/miR-874, miR-181b/miR-874, miR-107/miR-132, miR-491-5p/miR-132, miR-107/miR-323-3p, miR-127/miR-134, miR-491-5p/miR-874, miR-491-5p/miR-323-3p, miR-127/miR-432, let-7e/miR-134, let-7e/miR-411, miR-107/miR-411, miR-491-5p/miR-411, miR-107/miR-874, miR-181a/miR-9*, miR-491-5p/miR-210, miR-181b/miR-335, miR-99b/miR-335, miR-107/miR-210, miR-127/487b, miR-181a/miR-874, miR-9/miR-9*, miR-107/miR-487b, miR-107/miR-432, miR-9/miR-335, miR-181a/miR-132, miR-181b/miR-210, and miR-99b/miR-132.

In another embodiment of any of the above disease differentiation methods involving the first and second miRNAs which are brain-enriched, the pair of the first miRNA and the second miRNA is selected from the group consisting of: let-7e/miR-335, miR-107/miR-335, miR-127/miR-323-3p, let-7e/miR-411, miR-99b/miR-335, miR-491-5p/miR-335, miR-127/miR-134, miR-744/miR-335, miR-9/miR-335, miR-181b/miR-335, miR-107/miR-411, miR-181a/miR-335, let-7e/miR-9*, miR-491-5p/miR-411, let-7e/miR-132, miR-181b/miR-132, miR-9/miR-9*, miR-9/miR-134, miR-107/miR-134, miR-181b/miR-874, let-7e/miR-134, miR-107/miR-132, miR-107/miR-9*, miR-127/miR-335, miR-9/miR-132, miR-181b/miR-9*, miR-491-5p/miR-132, let-7e/miR-210, miR-491-5p/miR-9*, miR-107/miR-323-3p, miR-491-5p/miR-323-3p, miR-491-5p/miR-134, let-7e/miR-874, miR-181b/miR-210, miR-9/miR-874, miR-9/miR-485-3p, miR-744/miR-134, and miR-181b/miR-323-3p.

In one embodiment of the above disease differentiation methods involving the first and second miRNAs one of which is brain-enriched and another inflammation-associated, the pair of the first miRNA and the second miRNA is selected from the group consisting of: let-7e/miR-146a, miR-107/miR-146a, miR-491-5p/miR-146a, miR-107/miR-146b, miR-491-5p/miR-146b, miR-155/miR-874, let-7e/miR-146b, miR-155/miR-9*, miR-155/miR-335, miR-155/miR-411 and miR-744/miR-146a. In another embodiment of the above disease differentiation methods involving the first and second miRNAs one of which is brain-enriched and another inflammation-associated, the pair of the first miRNA and the second miRNA is selected from the group consisting of: miR-107/miR-146a, miR-491-5p/miR-146a, miR-155/miR-132, miR-155/miR-335, miR-107/miR-146b, miR-491-5p/miR-146b, miR-9/miR-146a, let-7e/miR-146b, miR-9/miR-146b, let-7e/miR-146a, miR-155/miR-874, miR-155/miR-9*, miR-155/miR-411, miR-744/miR-146a, miR-155/miR-210, miR-155/miR-146b, miR-744/miR-146b, miR-155/miR-146a, miR-155/miR-134, and miR-181b/miR-146b.

In one embodiment of any of the above methods, the method comprises measuring the level and calculating the ratios of the levels for two or more different pairs of miRNA. In one specific embodiment, the method comprises measuring the level and calculating the ratios of the levels for one or more pair combinations selected from the group consisting of:

(a) miR-181b/miR-323-3p and miR-99b/miR-9*,
(b) miR-491-5p/miR-487b plus miR-9/miR-146a, and
(c) miR-491-5p/miR-210 plus miR-181a/miR-146b.

In one embodiment of any of the above disease detection or differentiation methods, the method comprises measuring the levels of the miRNAs in two or more bodily fluid samples collected from the subject, wherein the samples have been collected at spaced apart time points.

In one embodiment of any of the above methods involving bodily fluid samples which have been collected at spaced apart time points, the bodily fluid samples are obtained several months apart (e.g., 3-6 months apart).

In one embodiment of any of the above methods, the method further comprises normalizing the levels of the first and second miRNAs to the level of a normalizer miRNA. In one specific embodiment, the normalizer miRNA is miRNA which is expressed in numerous tissues but is not significantly expressed in brain.

In one embodiment of any of the above methods, the subject is human. In another embodiment of any of the above methods, the subject is an experimental animal (e.g., an animal model of a neurodegenerative disease such as, e.g., PD).

In one embodiment of any of the above methods, the bodily fluid is selected from the group consisting of blood plasma, serum, urine, cerebrospinal fluid (CSF), and saliva.

In one embodiment of any of the above methods, the method comprises the step of collecting the bodily fluid sample(s) from the subject (e.g., prior to step (a)).

In one embodiment of any of the above methods, the level of the miRNAs is determined using a method selected from the group consisting of hybridization, RT-PCR, and sequencing.

In one embodiment of any of the above methods, prior to measuring miRNA level, the miRNA is purified from the bodily fluid sample.

In one embodiment of any of the above methods, the method further comprises the step of reducing or eliminating degradation of the miRNAs.

In one embodiment of any of the above disease detection or disease monitoring methods, the method further comprises administering a therapeutic or preventive treatment to the subject that has been diagnosed as having the neurodegenerative disease (e.g., PD) or as being at risk of progression to a more severe form of the neurodegenerative disease (e.g., PD). In case of PD, non-limiting examples of useful drug treatments include, for example, administration of dopamine-replenishing or dopamine mimicking drugs such as, e.g., levodopa or levodopa combination treatments, which may include administration with dopa decarboxylase inhibitors (e.g., carbidopa, benserazide); dopamine enhancers, such as catechol o-methyltransferase (COMT) inhibitors (e.g., entacapone, tolcapone); dopamine receptor agonists (e.g., ropinirole, pramipexole, rotigotine, apomorphine, pergolide, bromocriptine); monoamine oxidase (MAOIs) inhibitors, which can be used alone or with levodopa (e.g., selegiline, rasagiline, zydis selegiline HCl salt); amantadine (used to combat tremor and side effects of levodopa administration); anti-cholinergenics (e.g., trihexyphenidyl, benztropine). Other potentially useful drugs currently under study for treatment of PD include antiglutamatergics (e.g., memantine, safinomide); neurturin therapies; anti-apoptotics (e.g., omigapil, CEP-1347); promitochondrials (e.g., Coenzyme $Q_{10}$, creatine); calcium channel blockers, including isradipine, and growth factors such as GDNF; as well as drugs or vaccines targeting alpha-synuclein. Non-limiting examples of useful surgical therapies include, for example, deep brain stimulation (DBS), involving implantation of a battery-powered electrode in the brain; operations directly on neural tissue (e.g., thalamotomy, pallidotomy, subthalmatomy); and dopamergic cell transplant. Diet and physical exercise regimen may also be used (separately or in combination with other treatments) to alleviate PD symptoms. Non-limiting examples of useful food supplements include, for example, antioxidants such as vitamins C and E, calcium, ginger root, green tea and green tea extracts, St. John's Wort, *Ginkgo biloba*, milk thistle, vitamin B12, and folic acid. Currently it is not clear if PD can be reversed. Effective treatment can mean PD improvement (decrease of a biomarker miRNA ratio) or prevention/inhibition of further development of PD (biomarker miRNA ratio stays the same or increases slower).

In one embodiment of any of the above disease detection or disease progression monitoring methods, the method further comprises recruiting the subject in a clinical trial.

In conjunction with the above methods of the invention, the invention also provides various kits. Non-limiting examples of the kits of the invention include:

1. A kit for detecting PD comprising primers and/or probes specific for one or more pairs of miRNAs selected from the group consisting of: let-7e/miR-335, miR-107/miR-335, miR-491-5p/miR-335, miR-744/miR-335, miR-99b/miR-335, let-7e/miR-9*, miR-491-5p/miR-9*, let-7e/miR-132, miR-107/miR-132, miR-491-5p/miR-132, let-7e/miR-134, miR-107/miR-134, miR-99b/miR-134, miR-491-5p/miR-134, let-7e/miR-323-3p, miR-107/miR-323-3p, miR-127/miR-323-3p, miR-181b/miR-323-3p, miR-99b/miR-323-3p, miR-491-5p/miR-323-3p, let-7e/miR-411, miR-107/miR-411, and miR-491-5p/miR-411; miR-155/miR-335, let-7e/miR-146b, miR-491-5p/miR-146a, let-7e/miR-146a, miR-744/miR-146a, miR-155/miR-16, miR-155/miR-132, miR-155/miR-323-3p, miR-155/miR-411, miR-491-5p/miR-146b, miR-155/miR-146a, and miR-155/miR-146b.

2. A kit for differentiating PD from MCI comprising primers and/or probes specific for one or more pairs of miRNAs selected from the group consisting of: let-7e/miR-335, let-7e/miR-9*, miR-107/miR-335, miR-127/miR-323-3p, miR-491-5p/miR-335, miR-491-5p/miR-9*, miR-107/miR-9*, miR-744/miR-335, let-7e/miR-132, miR-107/miR-134, miR-181b/miR-132, let-7e/miR-210, miR-181b/miR-9*, miR-181a/miR-335, miR-491-5p/miR-134, let-7e/miR-874, miR-181b/miR-874, miR-107/miR-132, miR-491-5p/miR-132, miR-107/miR-323-3p, miR-127/miR-134, miR-491-5p/miR-874, miR-491-5p/miR-323-3p, miR-127/miR-432, let-7e/miR-134, let-7e/miR-411, miR-107/miR-411, miR-491-5p/miR-411, miR-107/miR-874, miR-181a/miR-9*, miR-491-5p/miR-210, miR-181b/miR-335, miR-99b/miR-335, miR-107/miR-210, miR-127/487b, miR-181a/miR-874, miR-9/miR-9*, miR-107/miR-487b, miR-107/miR-432, miR-9/miR-335, miR-181a/miR-132, miR-181b/miR-210, and miR-99b/miR-132; let-7e/miR-146a, miR-107/miR-146a, miR-491-5p/miR-146a, miR-107/miR-146b, miR-491-5p/miR-146b, miR-155/miR-874, let-7e/miR-146b, miR-155/miR-9*, miR-155/miR-335, miR-155/miR-411, and miR-744/miR-146a.

3. A kit for differentiating PD from AD comprising primers and/or probes specific for one or more pairs of miRNAs selected from the group consisting of: let-7e/miR-335, miR-107/miR-335, miR-127/miR-323-3p, let-7e/miR-411, miR-99b/miR-335, miR-491-5p/miR-335, miR-127/miR-134, miR-744/miR-335, miR-9/miR-335, miR-181b/miR-335, miR-107/miR-411, miR-181a/miR-335, let-7e/miR-9*, miR-491-5p/miR-411, let-7e/miR-132, miR-181b/miR-132, miR-9/miR-9*, miR-9/miR-134, miR-107/miR-134, miR-181b/miR-874, let-7e/miR-134, miR-107/miR-132, miR-107/miR-9*, miR-127/miR-335, miR-9/miR-132, miR-181b/miR-9*, miR-491-5p/miR-132, let-7e/miR-210, miR-491-5p/miR-9*, miR-107/miR-323-3p, miR-491-5p/miR-323-3p, miR-491-5p/miR-134, let-7e/miR-874, miR-181b/miR-210, miR-9/miR-874, miR-9/miR-485-3p, miR-744/miR-134, and miR-181b/miR-323-3p; miR-107/miR-146a, miR-491-5p/miR-146a, miR-155/miR-132, miR-155/miR-335, miR-107/miR-146b, miR-491-5p/miR-146b, miR-9/miR-146a, let-7e/miR-146b, miR-9/miR-146b, let-7e/miR-146a, miR-155/miR-874, miR-155/miR-9*, miR-155/miR-411, miR-744/miR-146a, miR-155/miR-210, miR-155/miR-146b, miR-744/miR-146b, miR-155/miR-146a, miR-155/miR-134, and miR-181b/miR-146b.

4. A kit comprising primers and/or probes specific for one or more combinations of pairs of miRNAs selected from the group consisting of:
(a) miR-181b/miR-323-3p and miR-99b/miR-9*,
(b) miR-491-5p/miR-487b and miR-9/miR-146a, and
(c) miR-491-5p/miR-210 and miR-181a/miR-146b.

Any of the above kits can further comprise miRNA isolation and/or purification means and/or instructions for use.

In a separate aspect, the invention provides a method for selecting a biomarker miRNA pair for diagnosis and/or monitoring of a pathology, said method comprising the following steps:
(a) selecting at least four miRNAs known to be enriched in an organ affected by the pathology;
(b) measuring the level of each miRNA selected in step (a) in bodily fluid samples from two subject cohorts;
(c) calculating the mean level of each miRNA measured in step (b);
(d) calculating the difference between the mean miRNA levels calculated in step (c);
(e) comparing the differences between the mean miRNA levels calculated in step (d) between all studied miRNAs and selecting as potential biomarker pairs those miRNA pairs for which the difference calculated in step (d) for one miRNA is at least 1.5 times the difference calculated for the other miRNA;
(f) calculating Spearman's rank correlation coefficient (r) for each potential biomarker miRNA pair selected in step (e), and
(g) identifying the miRNA pair as a suitable biomarker pair for diagnosis and/or monitoring of said pathology if its (r) value calculated in step (f) is at least 0.8.

In a related aspect, the invention provides a method for selecting a biomarker miRNA pair for diagnosis and/or monitoring of a pathology, said method comprising the following steps:
(a) selecting at least four miRNAs known to be enriched in an organ affected by the pathology;
(b) measuring the level of each miRNA selected in step (a) in bodily fluid samples from two subject cohorts;
(c) calculating Spearman's rank correlation coefficient (r) for all possible pairs of individual miRNAs measured in step (b);
(d) selecting as potential biomarker pairs those miRNA pairs which have the (r) value calculated in step (c) of at least 0.8;
(e) calculating the mean level of each miRNA selected in step (d);
(f) calculating the difference between the mean miRNA levels calculated in step (e);
(g) identifying a miRNA pair as a suitable biomarker pair for diagnosis and/or monitoring of said pathology if the difference calculated in step (f) for one miRNA is at least 1.5 times the difference calculated for the other miRNA.

In another related aspect, the invention provides a method for selecting a biomarker miRNA pair for diagnosis and/or monitoring of a pathology, said method comprising the following steps:
(a) selecting at least four miRNAs known to be enriched in an organ affected by the pathology;
(b) measuring the level of each miRNA selected in step (a) in bodily fluid samples from two subject cohorts;
(c) calculating Spearman's rank correlation coefficient (r) for all possible pairs of individual miRNAs measured in step (b);
(d) selecting as potential biomarker pairs those miRNA pairs which have the (r) value calculated in step (c) of at least 0.8;
(e) calculating P-value of two subject cohorts separation for each miRNA pair selected in step (d), and
(f) identifying a miRNA pair as a suitable biomarker pair for diagnosis and/or monitoring of said pathology if this pair differentiates two subject cohorts with a statistically significant P-value.

In yet another related aspect, the invention provides a computer-implemented method for selecting a biomarker miRNA pair for diagnosis and/or monitoring of a pathology, said method comprising the following steps:
(a) selecting a group of miRNAs known to be enriched in an organ affected by the pathology;
(b) measuring the level of each miRNA selected in step (a) in bodily fluid samples from two subject cohorts;
(c) electronically calculating the mean level of each miRNA measured in step (b);
(d) electronically calculating a difference between the mean miRNA levels calculated in step (c);
(e) selecting from the group of measured miRNAs a set of potential miRNA pairs each comprising a first miRNA and a second miRNA, wherein the calculated difference in the mean level in step (d) of the first miRNA is at least 1.5 times the calculated difference in the mean level of the second miRNA;
(f) electronically calculating the Spearman's rank correlation coefficient (r) for each potential miRNA pair selected in (e);
(g) selecting from the set of potential miRNA pairs those miRNA pairs, which are suitable for the diagnosis and/or monitoring of the pathology, wherein the (r) value calculated in step (f) is at least 0.8, and
(h) displaying all or part of the miRNA pairs selected in step (g).

In a further related aspect, the invention provides a computer-implemented method for selecting a biomarker miRNA pair for diagnosis and/or monitoring of a pathology, said method comprising the following steps:
(a) selecting a group of miRNAs known to be enriched in an organ affected by the pathology;
(b) measuring the level of each miRNA selected in step (a) in bodily fluid samples from two subject cohorts;

(c) electronically calculating the Spearman's rank correlation coefficient (r) for all possible pairs of individual miRNAs measured in step (b);

(d) selecting from the group of measured miRNAs a set of potential biomarker miRNA pairs, wherein the (r) value calculated in step (c) is at least 0.8;

(e) electronically calculating the mean level of each miRNA selected in step (d);

(f) electronically calculating the difference between the mean miRNA levels calculated in step (e);

(g) selecting from the group of measured miRNAs a set of suitable miRNA biomarker pairs each comprising a first miRNA and a second miRNA, wherein for each suitable biomarker miRNA pair, the calculated difference in the mean level in step (f) of the first miRNA is at least 1.5 times the calculated difference in the mean level of the second miRNA, and (h) displaying all or part of the suitable biomarker miRNA pairs selected in step (g).

In an additional related aspect, the invention provides a computer-implemented method for selecting a biomarker miRNA pair for diagnosis and/or monitoring of a pathology, said method comprising the following steps:

(a) selecting a group of miRNAs known to be enriched in an organ affected by the pathology;

(b) measuring the level of each miRNA selected in step (a) in bodily fluid samples from two subject cohorts;

(c) electronically calculating the Spearman's rank correlation coefficient (r) of the levels measured in step (b) for all possible pairs of individual miRNAs;

(d) selecting from the group of measured miRNAs a set of potential biomarker miRNA pairs, wherein the (r) value calculated in step (c) is at least 0.8;

(e) electronically calculating P-value of two subject cohorts separation for each miRNA pair selected in step (d);

(f) selecting a miRNA pair as a suitable biomarker pair for diagnosis and/or monitoring of said pathology if this miRNA pair differentiates two subject cohorts with a statistically significant P-value, and (g) displaying all or part of the suitable biomarker miRNA pairs selected in step (f).

In one embodiment of any of the above methods for selecting a biomarker miRNA pair, the miRNA level is measured by a method selected from the group consisting of RT-PCR-based methods, miRNA array-based methods, new generation sequencing, and hybridization.

In one embodiment of any of the above methods for selecting a biomarker miRNA pair, the two subject cohorts are (1) subjects having the pathology and (2) age, gender and ethnicity-matched healthy subjects. In another embodiment of any of the above methods for selecting a biomarker miRNA pair, the two subject cohorts are subjects having two different pathologies of the organ. In yet another embodiment of any of the above methods for selecting a biomarker miRNA pair, the two subject cohorts are (1) younger subjects and (2) older subjects. In a further embodiment of any of the above methods for selecting a biomarker miRNA pair, the two subject cohorts are age and ethnicity-matched (1) males and (2) females.

In one embodiment of any of the above methods for selecting a biomarker miRNA pair, the bodily fluid is selected from the group consisting of plasma, serum, cerebrospinal fluid (CSF), urine, and saliva.

In one embodiment of any of the above methods for selecting a biomarker miRNA pair, the subject is human. In another embodiment of any of the above methods for selecting a biomarker miRNA pair, the subject is an experimental animal.

In one embodiment of any of the above methods for selecting a biomarker miRNA pair involving P-value, the P-value is calculated in step (e) using Mann-Whitney test. In one embodiment of any of the above methods for selecting a biomarker miRNA pair involving P-value, the statistically significant P-value is at least 0.05.

In one embodiment of any of the above methods for selecting a biomarker miRNA pair, the pathology is a neurodegenerative disease (e.g., Parkinson's disease (PD), Alzheimer's disease (AD) and Mild Cognitive Impairment (MCI)).

In one embodiment of any of the above methods for selecting a biomarker miRNA pair, the organ affected by the pathology is brain.

These and other aspects of the present invention will be apparent to those of ordinary skill in the art in the following description, claims and drawings.

DETAILED DESCRIPTION OF THE INVENTION

Figure 1A:
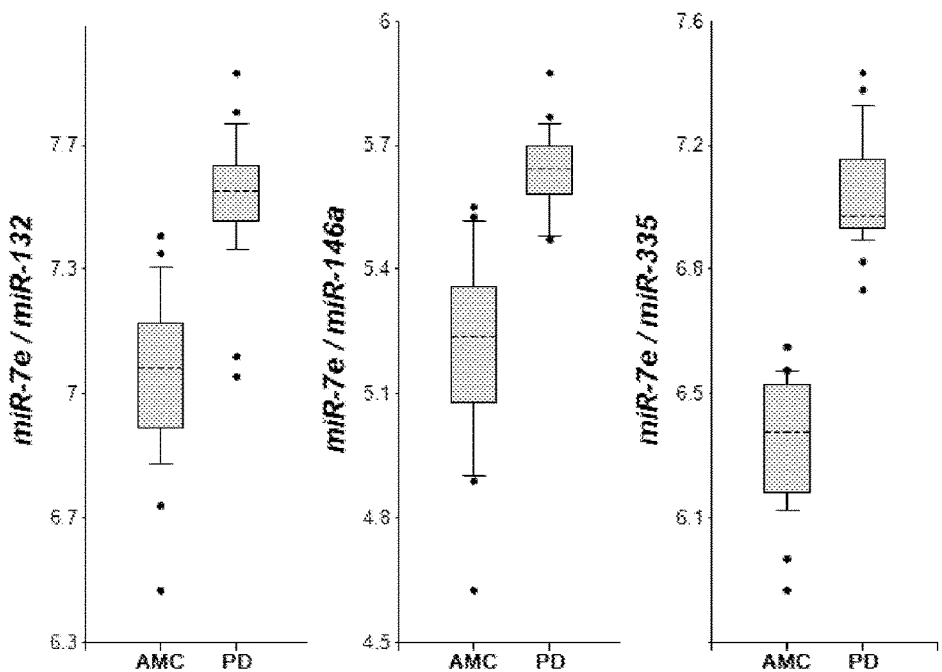
FIGS. 1A-F are graphs showing ratios of miRNA levels (biomarker pairs) in plasma of age-matched controls (AMC) and Parkinson's disease (PD) patients. A, C and E present box and whisker plots in the Log 10 scale. The upper and lower limits of the boxes and the lines inside the boxes indicate the 75th and 25th percentiles and the median, respectively. The upper and lower horizontal bars denote the 90th and 10th percentiles, respectively. The points indicate assay values located outside of 80% data. B, D and F present Receiver-Operating Characteristic (ROC) curve analysis of differentiation between PD patients and AMC. Sensitivity, specificity and accuracy for each biomarker/normalizer pair are calculated for the "cutoff" point (indicated as a dot on each plot)—the value of the ratio of paired miRNA where the accuracy of predictions is the highest.
Figure 1B:
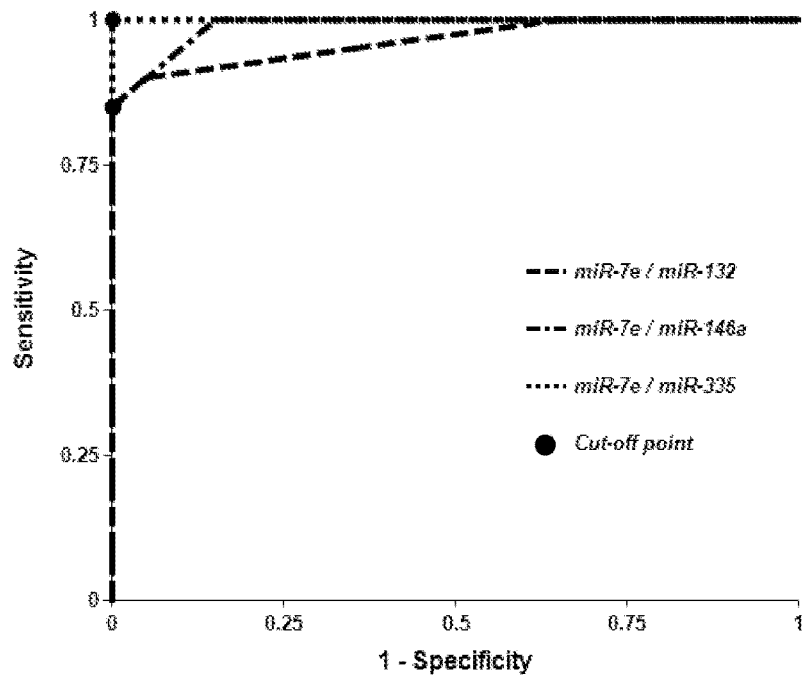
Figure 1C:
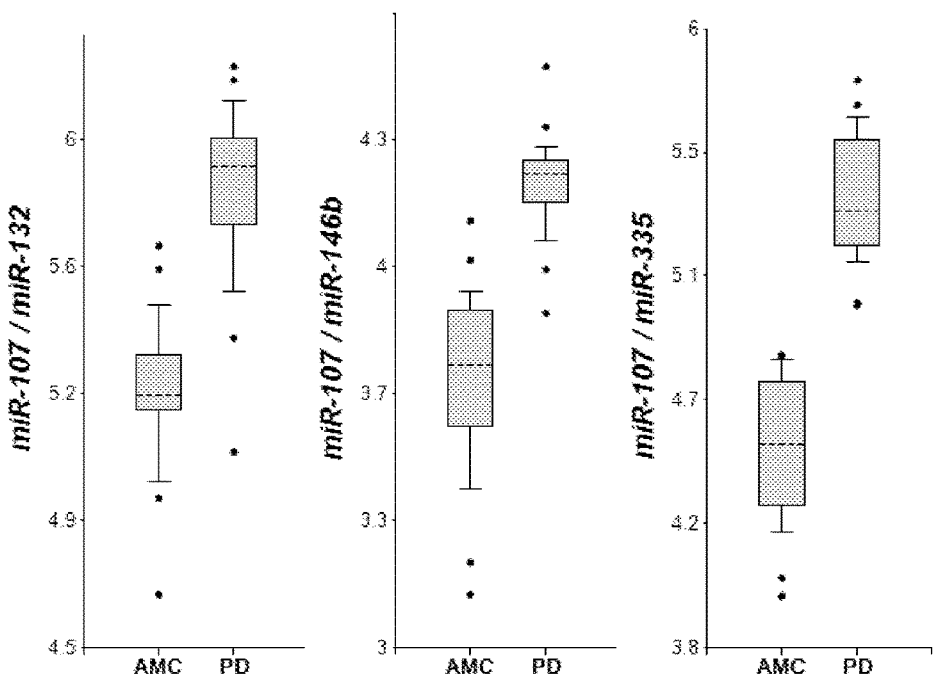
Figure 1D:
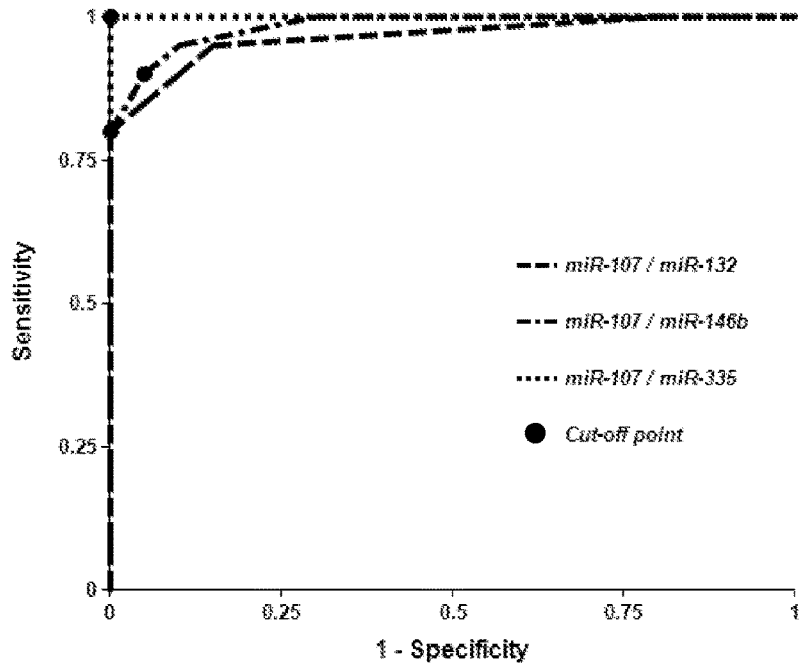
Figure 1E:
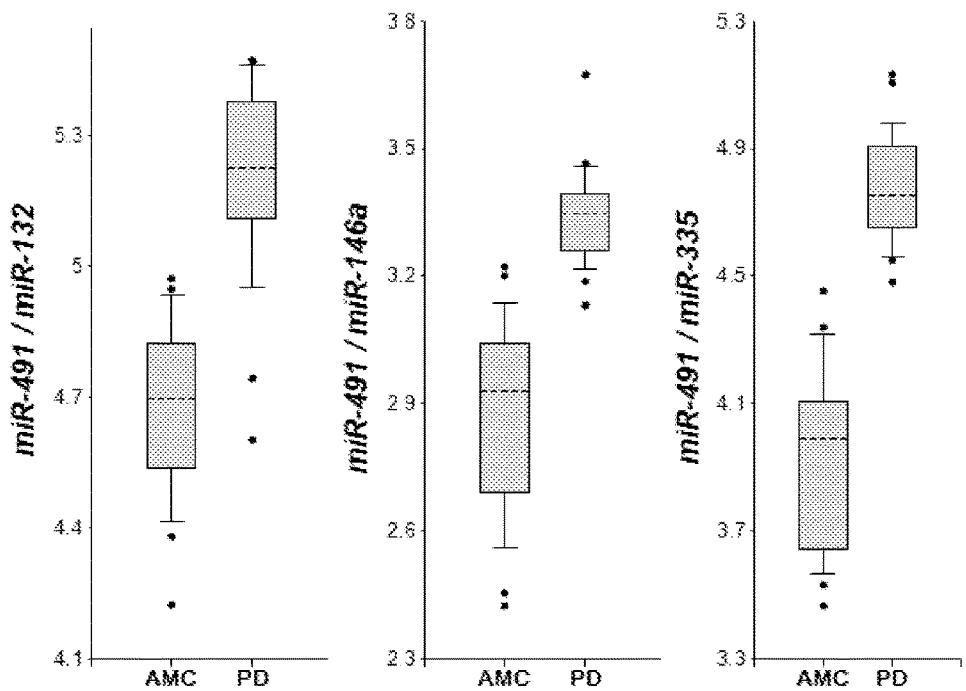
Figure 1F:
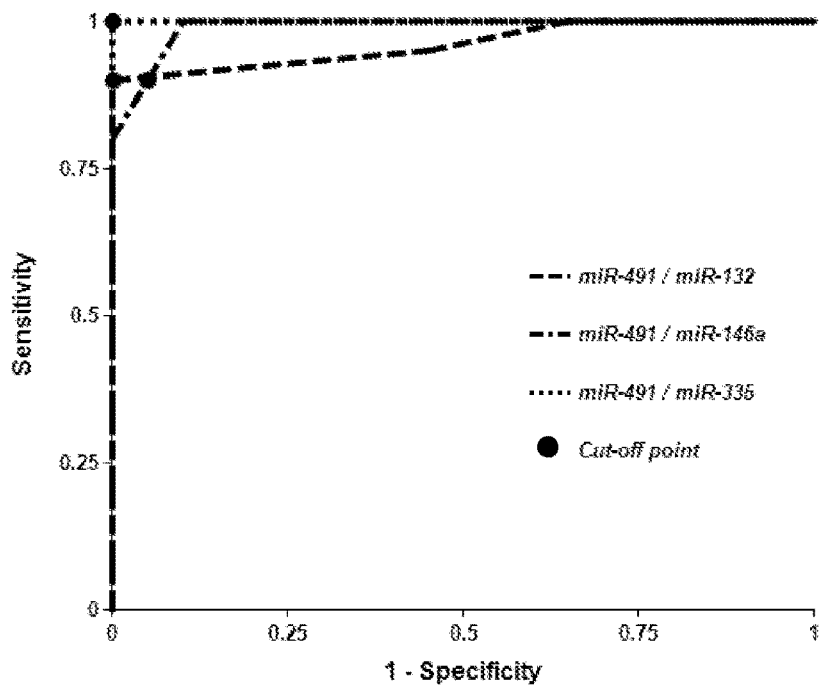
Figure 2A:
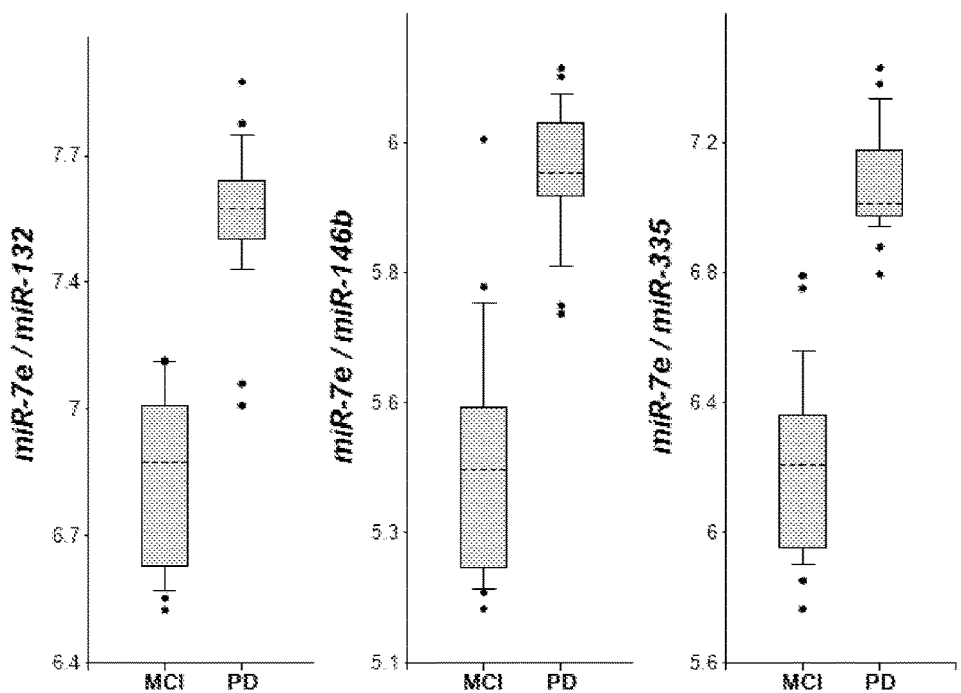
FIGS. 2A-F are graphs showing ratios of miRNA levels (biomarker pairs) in plasma of MCI and PD patients. A, C and E present box and whisker plots in the Log 10 scale. The upper and lower limits of the boxes and the lines inside the boxes indicate the 75th and 25th percentiles and the median, respectively. The upper and lower horizontal bars denote the 90th and 10th percentiles, respectively. The points indicate assay values located outside of 80% data. B, D and F present Receiver-Operating Characteristic (ROC) curve analysis of differentiation between PD patients and MCI. Sensitivity, specificity and accuracy for each biomarker/normalizer pair are calculated for the "cutoff" point (indicated as a dot on each plot)—the value of the ratio of paired miRNA where the accuracy of predictions is the highest.
Figure 2B:
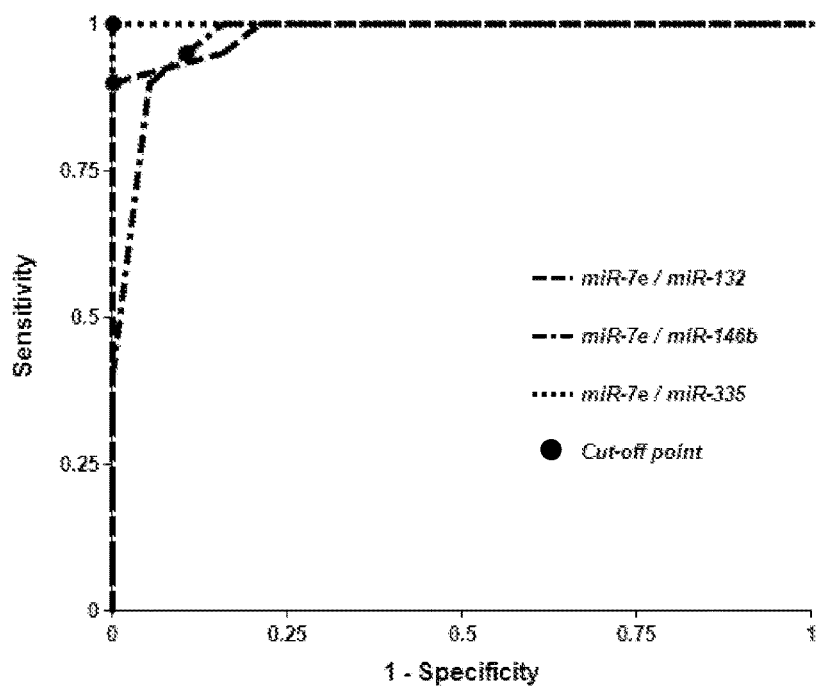
Figure 2C:
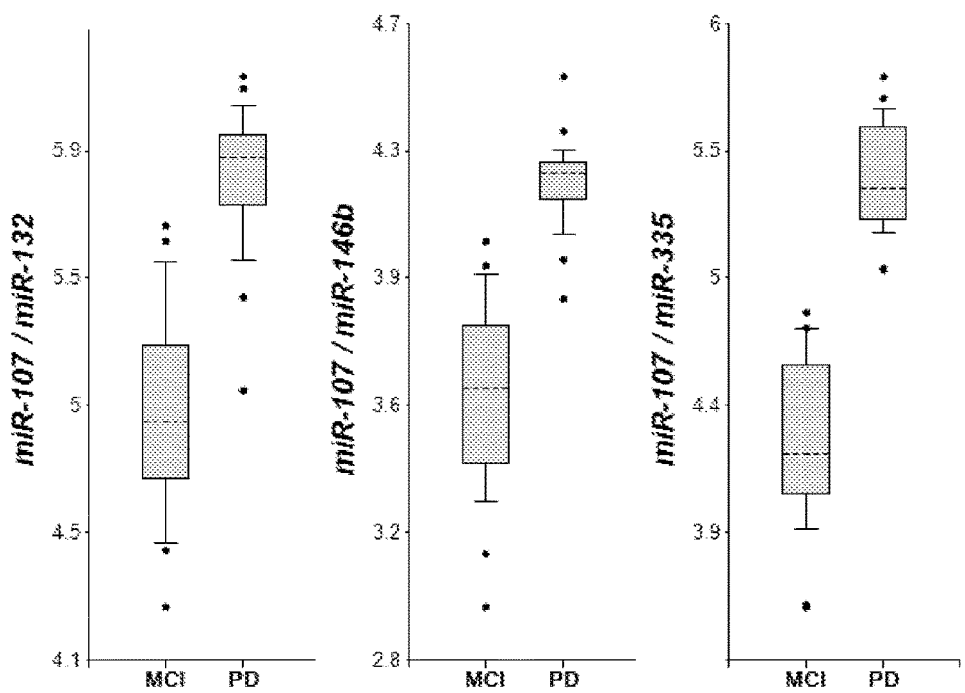
Figure 2D:
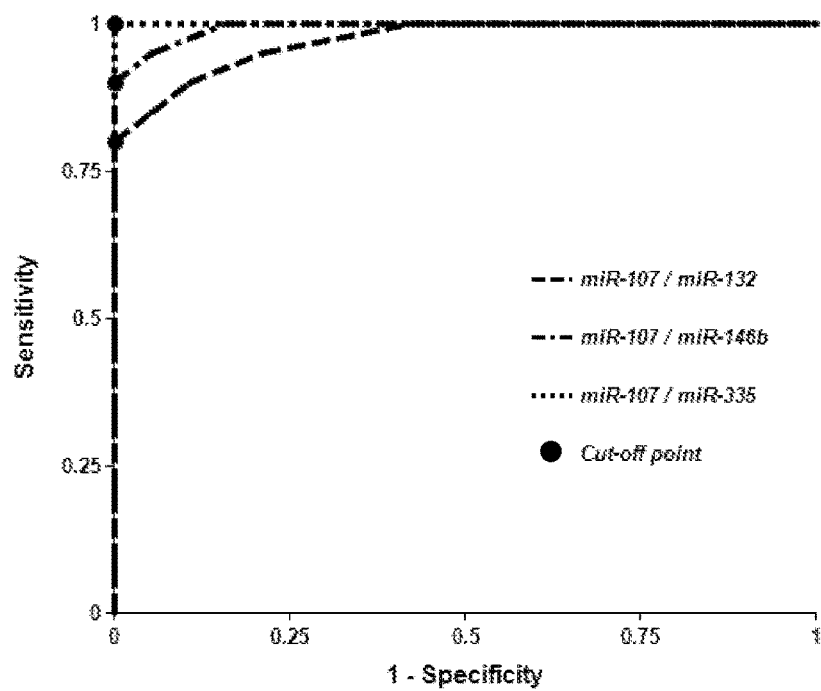
Figure 2E:
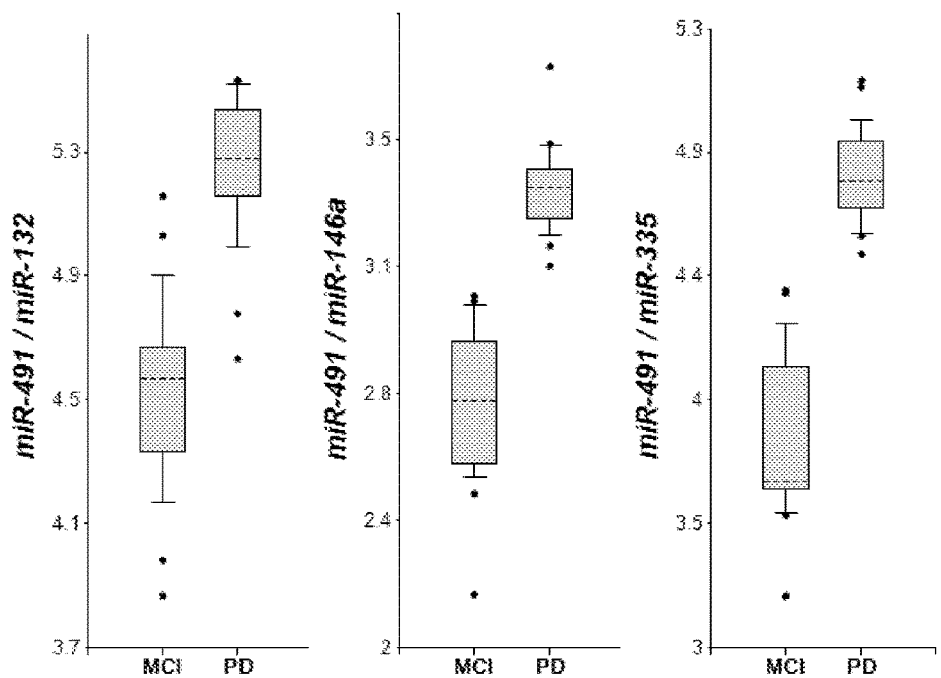
Figure 2F:
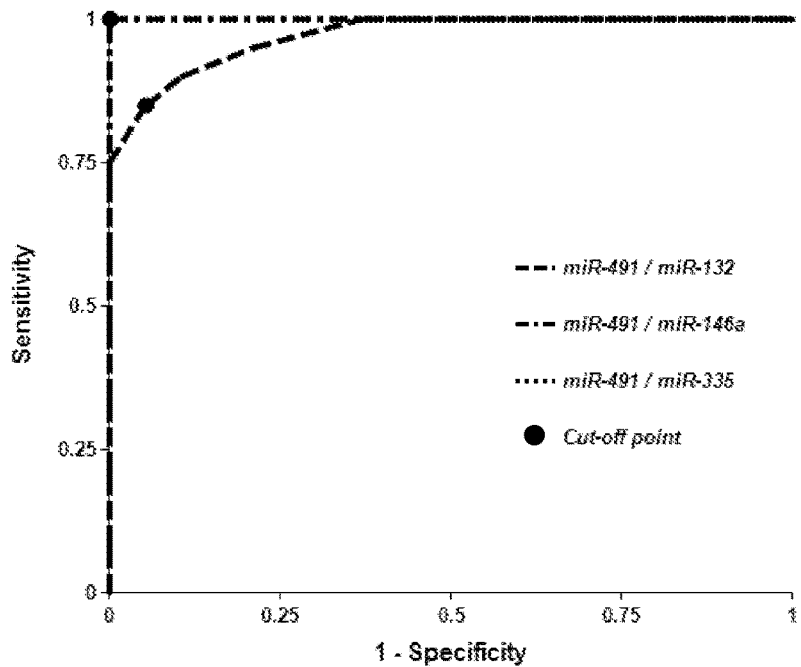
Figure 3A:
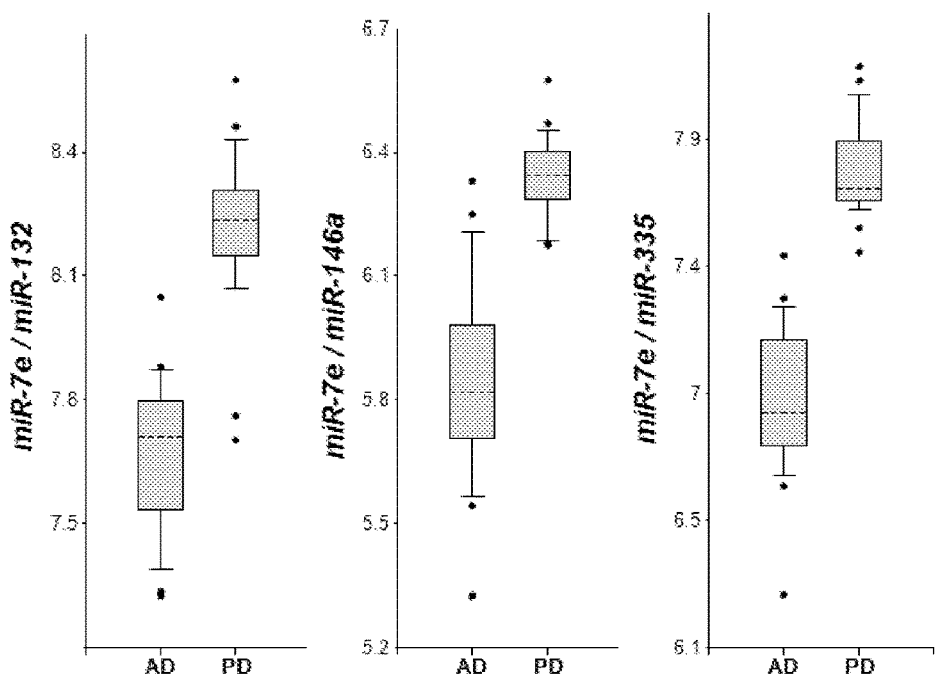
FIGS. 3A-F are graphs showing ratios of miRNA levels (biomarker pairs) in plasma of AD and PD patients. A, C and E present box and whisker plots in the Log 10 scale. The upper and lower limits of the boxes and the lines inside the boxes indicate the 75th and 25th percentiles and the median, respectively. The upper and lower horizontal bars denote the 90th and 10th percentiles, respectively. The points indicate assay values located outside of 80% data. B, D and F present Receiver-Operating Characteristic (ROC) curve analysis of differentiation between PD patients and AD. Sensitivity, specificity and accuracy for each biomarker/normalizer pair are calculated for the "cutoff" point (indicated as a dot on each plot)—the value of the ratio of paired miRNA where the accuracy of predictions is the highest.
Figure 3B:
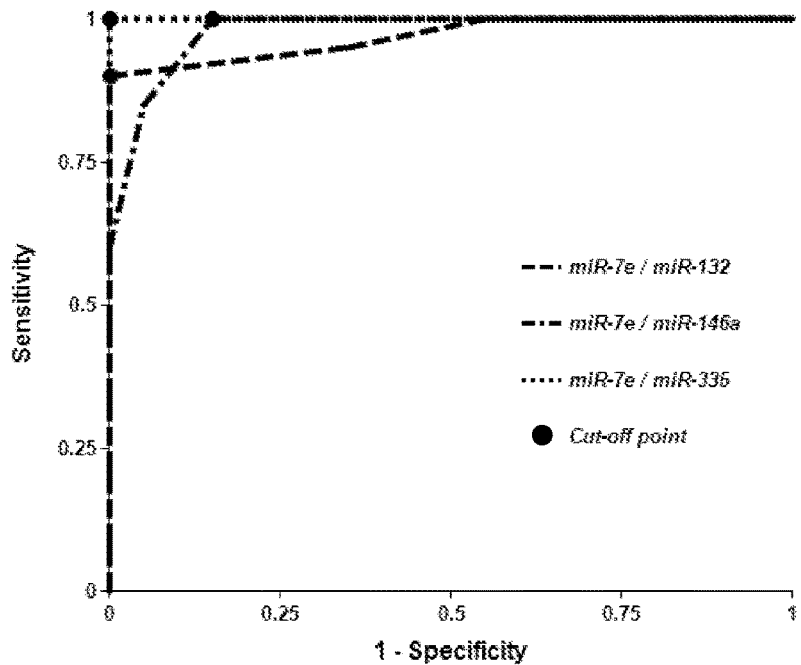
Figure 3C:
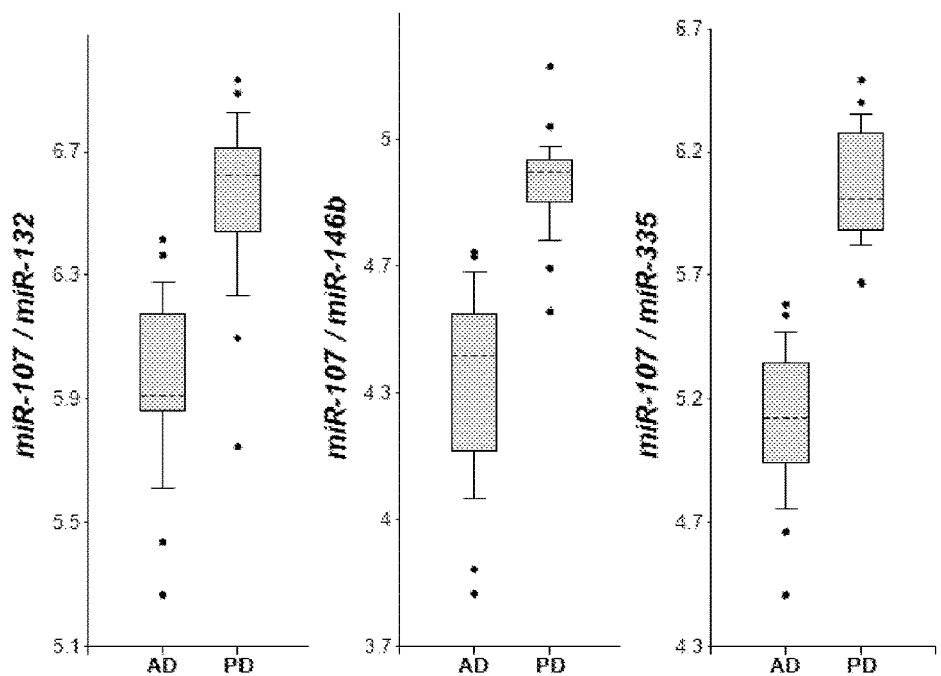
Figure 3D:
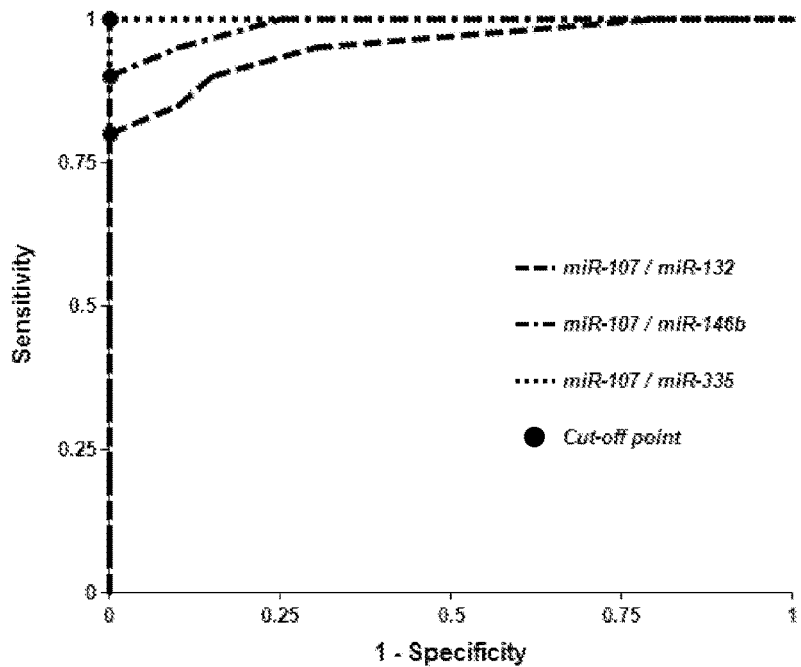
Figure 3E:
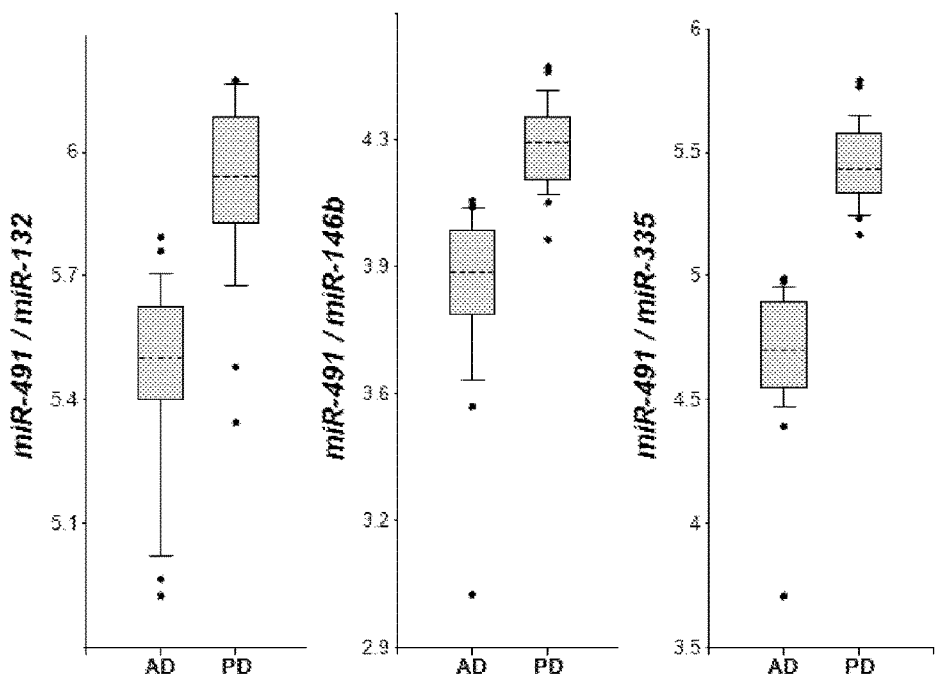
Figure 3F:
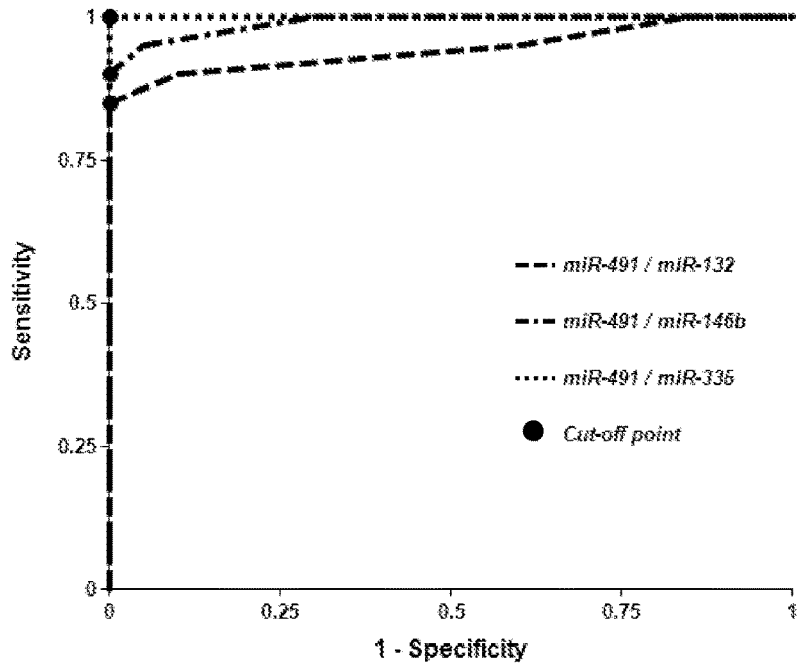

The present invention is based on the following ideas and findings made by the present inventors:
(1) changes in concentrations of circulating miRNAs enriched in the brain, and more specifically in brain areas involved in a particular pathology, are more likely to reflect associated pathologic processes in the brain than ubiquitous or other brain-enriched miRNAs;
(2) miRNAs present in neurites and synapses should be analyzed, because dysfunction and destruction of neurites and synapses is characteristic of early stages of neurodegeneration, and therefore, can affect expression and secretion of these miRNAs;
(3) to compensate for processes unrelated directly to a particular pathology, e.g., changes in blood-brain barrier permeability, the present inventors used the "biomarker pair" approach normalizing miRNAs enriched in neurons of damaged brain area(s) by other brain-enriched miRNAs, which could be expressed in brain areas or cell types not involved in early stages of a specific neurodegenerative disease which is being diagnosed, as well as miRNAs with plasma levels changing differently when compared with miRNAs enriched in the area of interest;
(4) high correlation of plasma concentrations of miRNAs used as numerator and denominator in a biomarker miRNA pair is very important for its sensitivity and specificity.

The present invention is based on analysis of the ratios of the levels for pairs of circulating cell-free miRNA in bodily fluids, wherein both miRNA in the pair are brain-enriched, and either (i) are enriched in certain brain areas, which are (for one miRNA in the pair) or are not (for the other miRNA in the pair) involved in PD development, or (ii) are enriched in different cell types (e.g., neurons and glial cells), or (iii) are enriched in the same brain area but whose expression and/or secretion change differently due to PD development. Brain-enriched miRNAs which are particularly useful as numerators in the miRNA pairs of the invention include neuronal miRNAs present in neurites and synapses (i.e., synapse and/or neurite miRNAs), whose normal functioning suffers on early stages of PD, AD and other neurodegenerative diseases. The present invention also encompasses the analysis of miRNAs involved in inflammatory processes (e.g., miR-155) and their use as potential biomarkers in combination with miRNAs enriched in brain area(s) involved in pathology. Since various neurodegenerative diseases are characterized by neuronal pathology in different brain areas such biomarker miRNA pairs can be used for differentiating those pathologies from each other independent of their clinical symptoms, if any. In addition, discovered biomarkers, reflecting important events in pathology development, could be used for disease and treatment monitoring as well as drug screening.

Use of brain-enriched miRNA significantly increases chances that changes of their levels in plasma are caused by brain pathology, and changes in bodily fluid concentration of miRNA enriched in a particular brain area should be indicative of pathology in that brain part. For example, changes in levels of hippocampus- or midbrain-enriched miRNA would be respectively associated with AD and PD, reflecting synapse and neuronal dysfunctions in these brain areas. In addition, concentrations of organ-enriched miRNA in blood cells are low, which decreases contamination of plasma and serum by miRNA leakage during purification of these bodily fluids.

The concentrations of miRNAs detected in bodily fluids depend on many biological and technical factors. Biological factors include miRNA levels in various tissues, intensity of secretion and excretion into extracellular space, forms of circulating miRNAs (exosomes and other vesicles, complexes with proteins and lipids) affecting their ability to cross various barriers, e.g. blood-brain, placental, and kidney barriers, and miRNA stability and half-life in the bloodstream. Technical factors include variability in methods of bodily fluid collection and storage, methods used for miRNA extraction, and presence in bodily fluids of various factors affecting miRNA purification and quantitation. As a consequence, the importance of miRNA normalization is broadly recognized (Meyer et al., Biotechnol. Lett. 2010; 32: 1777-1788). At the same time, no single normalization method is commonly accepted.

The present invention is based on the use of brain-enriched miRNA pairs instead of (or in addition to) normalization per ubiquitous RNA or an average of numerous miRNA. The use of brain-enriched miRNA pairs (one as a numerator and another one as a denominator in a ratio) has several advantages. First, any pathology is usually associated with up-regulation of some miRNAs and down-regulation of other miRNAs, thus considering miRNA pairs of up- and down-regulated miRNAs may increase test sensitivity and specificity. Second, the use of a pair of brain-enriched miRNAs, rather than one brain-enriched miRNA, decreases potential overlap with pathologies of other organs. Third, one can expect that changes unrelated to or non-specific for a pathology of interest, such as, e.g., changes in blood supply, blood-brain permeability and others, will be better compensated for by using the pair of miRNAs enriched in the same organ. For example, changes in relative concentrations of miRNAs enriched in different brain areas or different cell types (e.g., neurons and glial cells) may be an indicator of disease progression, and so on.

In the present invention, since various miRNA are involved in regulation of different processes, combination of several miRNA pairs were also tested to find out the groups of miRNA pairs providing the highest test accuracy. Non-limiting examples of such groups include miR-181b/miR-323-3p plus miR-99b/miR-9*; miR-491-5p/miR-487b plus miR-9/miR-146a; miR-491-5p/miR-210 plus miR-181a/miR-146b (see FIG. 4).

Definitions

As used herein in connection with enrichment in brain, the term "enriched" means that miRNA concentration in brain is at least 4-5 times higher than in other organs.

As used herein in connection with enrichment in a certain area of the brain, the term "enriched" means that miRNA concentration in said area of the brain is higher (preferably, at least 2-fold higher, more preferably at least 5-fold higher, most preferably at least 10-fold higher) than in brain in general. The term refers to the difference in concentrations within the brain areas (e.g., as measured using qRT-PCR).

Within the meaning of the present invention, the term "synapse and/or neurite miRNA" refers to miRNA which (i)

is "brain-enriched" and (ii) is present in a synapse and/or neurite (i.e., axon and/or dendrite and/or spine). To be useful in the methods of the present invention, synapse and/or neurite miRNAs should be detectable in bodily fluids as a result of their release from neurons (e.g., due to secretion, neurite/synapse destruction or neuronal death).

The term "Mild Cognitive Impairment" or "MCI" refers to an intermediate stage between the expected cognitive decline of normal aging and the more serious decline of dementia. It can involve problems with memory, language, thinking and judgment that are greater than normal age-related changes (see, e.g., Jack et al., Alzheimer's and Dementia. 2011, Epub April 19).

The term "neurite" as used herein refers to any projection from the cell body of a neuron. This projection can be an axon, a dendrite, or a spine.

The term "axon" refers to a long, slender projection of a neuron that conducts electrical impulses away from the neuron's cell body or soma. Axons are distinguished from dendrites by several features, including shape (dendrites often taper while axons usually maintain a constant radius), length (dendrites are restricted to a small region around the cell body while axons can be much longer), and function (dendrites usually receive signals while axons usually transmit them). Axons and dendrites make contact with other cells (usually other neurons but sometimes muscle or gland cells) at junctions called synapses.

The term "dendrite" refers to a branched projection of a neuron that acts to conduct the electrochemical stimulation received from other neural cells to the cell body of the neuron from which the dendrites project.

The term "synapse" refers to specialized junctions, through which neurons signal to each other and to non-neuronal cells such as those in muscles or glands. A typical neuron gives rise to several thousand synapses. Most synapses connect axons to dendrites, but there are also other types of connections, including axon-to-cell-body, axon-to-axon, and dendrite-to-dendrite. In the brain, each neuron forms synapses with many others, and, likewise, each receives synaptic inputs from many others. As a result, the output of a neuron may depend on the input of many others, each of which may have a different degree of influence, depending on the strength of its synapse with that neuron. There are two major types of synapses, chemical synapses and electrical synapses. In electrical synapses, cells approach within about 3.5 nm of each other, rather than the 20 to 40 nm distance that separates cells at chemical synapses. In chemical synapses, the postsynaptic potential is caused by the opening of ion channels by chemical transmitters, while in electrical synapses it is caused by direct electrical coupling between both neurons. Electrical synapses are therefore faster than chemical synapses.

The term "normalizer miRNA" as used herein refers to miRNA which is used for normalization of miRNA concentration to account for various factors that affect appearance and stability of miRNA in plasma.

The term "neurodegenerative disease" is used herein to refer to brain pathologies, such as, e.g., Parkinson's disease (PD), Alzheimer's disease (AD), Mild Cognitive Impairment (MCI), Huntington's disease (HD), prion-caused diseases, frontotemporal dementia (FTD), Lewy body dementia, vascular dementias, Amyotrophic Later Sclerosis (ALS), Chronic Traumatic Encephalopathy (CTE), progressive supranuclear palsy (PSP), multiple system atrophy (MSA), corticobasal degeneration (CBGD), Pick's disease, olivopontocerebellar atrophy (OPCA), and other pathologies characterized by metabolic changes, followed by synapse dysfunction, neurite and synapse destruction and ultimately by neuronal death.

As used herein, the term "development stage of a neurodegenerative disease" refers to a specific extent of severity of a neurodegenerative disease (e.g., asymptomatic stage, early disease with some symptoms, late stages of disease, etc.).

The term "development of a neurodegenerative disease" is used herein to refer to any negative change in the extent/severity of a metabolic and/or structural change in individual neurons and/or any increase in the number of neurons affected. The phrase "improvement of a neurodegenerative disease" and similar terms refer to any positive change in the extent/severity of a metabolic and/or structural change in individual neurons and/or any decrease in the number of neurons affected.

The term "associated with" is used to encompass any correlation, co-occurrence and any cause-and-effect relationship.

The terms "microRNA" or "miRNA" as used herein refer to a class of small approximately 22 nt long non-coding RNA molecules. They play important roles in the regulation of target genes by binding to complementary regions of messenger transcripts (mRNA) to repress their translation or regulate degradation (Griffiths-Jones Nucleic Acids Research, 2006, 34, Database issue: D140-D144), Frequently, one miRNA can target multiple mRNAs and one mRNA can be regulated by multiple miRNAs targeting different regions of the 3' UTR. Once bound to an mRNA, miRNA can modulate gene expression and protein production by affecting, e.g., mRNA translation and stability (Baek et al., Nature 455(7209):64 (2008); Selbach et al., Nature 455(7209):58 (2008); Ambros, 2004, Nature, 431, 350-355; Bartel, 2004, Cell, 116, 281-297; Cullen, 2004, Virus Research., 102, 3-9; He et al., 2004, Nat. Rev. Genet., 5, 522-531; and Ying et al., 2004, Gene, 342, 25-28). Unless otherwise noted, the name of a specific miRNA refers to a mature miRNA sequence. Under current nomenclature rules, human miRNAs are preceded with the prefix "hsa-" (i.e., an abbreviation for *Homo sapiens*). Throughout the specification and figures the hsa-prefix may be dropped for purposes of abbreviation, thus, for example, "hsa-miR-155" and "miR-155" would represent the same RNA sequence.

Examples of neurite and/or synapse miRNAs useful in the methods of the present invention include, without limitation, Let-7e, miR-7, miR-9, miR-98, miR-99, miR-124a, miR-125a, miR-125b, miR-128a, miR-132, miR-134, miR-135a, miR-137, miR-138, miR-154, miR-182, miR-183, miR-213, miR-218, miR-323-3p, miR-329, miR-337, miR-369-3, miR-369-5p, miR-370, miR-381, miR-382, miR-409-3p, miR-425, miR-433-5p, miR-483-3p, miR-485-5p, miR-487b, miR-491-5p, miR-494, miR-495, miR-496, miR-541, miR-543, miR-656, miR-668, miR-874, miR-889, miR-935, miR-939, miR-9* and miR181a-1*. Information on most currently known miRNAs can be found in the miRNA database miRBase (available at the world wide web at mirbase.org). See also Burside et al., BMC Genomics 9:185 (2008); Williams et al., BMC Genomics 8:172 (2007); Landgraf et al., Cell 129:1401 (2007).

The term "miRNA array" refers to a multiplex technology used in molecular biology and in medicine. It consists of an arrayed series of multiple (e.g., thousands) microscopic spots of oligonucleotides, each containing a specific sequence (probe) complementary to a particular target miRNA. After probe-target hybridization under high-stringency conditions the resulting hybrids are usually detected and quantified by quantifying fluorophore-, silver-, or chemiluminescence-labeled targets to determine relative abundance of miRNA. In the methods of the present invention, both custom-made and commercially available miRNA arrays can be used. Examples of useful commercially available miRNA arrays (based on various methods of target labeling, hybrid detection and analysis) include arrays produced by Agilent, Illumina, Invitrogen, Febit, and LC Sciences.

The term "next generation sequencing technologies" broadly refers to sequencing methods which generate multiple sequencing reactions in parallel. This allows vastly increased throughput and yield of data. Non-limiting examples of commonly used next generation sequencing platforms include Helicos small RNA sequencing, miRNA BeadArray (Illumina), Roche 454 (FLX-Titanium), and ABI SOLiD.

An "individual" or "subject" or "animal", as used herein, refers to humans, veterinary animals (e.g., cats, dogs, cows, horses, sheep, pigs, etc.) and experimental animal models of neurodegenerative diseases. In a preferred embodiment, the subject is a human.

The term "purified" as used herein refers to material that has been isolated under conditions that reduce or eliminate the presence of unrelated materials, i.e., contaminants, including native materials from which the material is obtained. For example, RNA purification includes elimination of proteins, lipids, salts and other unrelated compounds present in bodily fluids. Besides, for some methods of analysis a purified miRNA is preferably substantially free of other RNA oligonucleotides contained in bodily fluid samples (e.g., rRNA and mRNA fragments, ubiquitous miR-NAs, which are expressed at high levels in almost all tissues [e.g., miR-16], etc.). As used herein, the term "substantially free" is used operationally, in the context of analytical testing of the material. Preferably, purified material substantially free of contaminants is at least 50% pure; more preferably, at least 90% pure, and still more preferably at least 99% pure. Purity can be evaluated by chromatography, gel electrophoresis, composition analysis, biological assay, and other methods known in the art.

As used herein, the term "similarly processed" refers to samples (e.g., bodily fluid samples or purified RNAs) which have been obtained using the same protocol.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 4 28-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999), U.S. Pat. Nos. 5,789,166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nucl. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218.

Methods for Identification of Diagnostic miRNA Pairs

To identify the most promising biomarker pairs, the present inventors used the following approach: selection of a numerator and a denominator for each pair from those circulating miRNAs, which significantly correlate (Spearman's rank correlation coefficient $r>0.8$) in a respective bodily fluid of different individuals. Concentrations of miR-NAs in plasma depend on numerous factors, including (i) levels of miRNA expression in various organs and tissues; (ii) levels of miRNA secretion from different cell types; (iii) stability of miRNAs in extracellular space and their appearance in plasma in different forms, such as exosomes and other microvesicles, complexes with proteins, lipids and, possibly, other molecules; and (iv) blood-brain barrier permeability for brain-enriched miRNAs. A pathological process may affect some or all of these factors. The present inventors suggest that a nominator and a denominator of an effective biomarker miRNA pair should share some of these basic common factors (e.g., both are brain-enriched and secreted in exosomes) and would change differently in response to a pathology. This does not mean that any correlated miRNA will form a good biomarker pair, since if they are similarly changed by pathology their ratio will mask those changes.

The present invention provides a method of "promising" miRNA pair selection, which method comprises the following steps:

1. Concentrations of miRNAs pre-selected on the basis of their enrichment in an organ of interest (e.g., brain) are measured in a bodily fluid (e.g., plasma, serum, cerebrospinal fluid (CSF), saliva, urine) of at least two comparative cohorts (e.g., a disease and control for a diagnostic test, two diseases for a test capable of differentiating two pathologies, a disease at different stages of pathologic process development, or a disease before and after treatment for monitoring tests).

2. Means of each miRNA concentrations are calculated for comparative cohorts.

3. The difference between the means for each miRNA from two comparative cohorts is calculated and miRNAs are divided in two groups: (i) with high difference values; and (ii) with low or with opposite sign difference values.

4. miRNAs from different groups are combined as potential biomarker pairs if parameters determined in step 3 differ at least 1.5 times. One miRNA is used as a numerator and another miRNA is used as a denominator in a potential "promising" miRNA pair.

5. To further reduce an impact of individual variations of each particular miRNA concentration in plasma or other bodily fluid, miRNA with high positive correlation (Spearman's rank correlation coefficient r calculated for all samples in compared groups is ≥0.8) are selected as a numerator and a denominator for the biomarker pair. This step significantly decreases the number of potential biomarker miRNA pairs, reduces variance of selected biomarkers caused by factors unrelated to processes differentiating two comparative cohorts and significantly increases test sensitivity and specificity.

The order of steps 3-4 and step 5 can be switched as follows:

After step 1, calculate Spearman's rank correlation coefficient (r) for all possible pairs of individual miRNA measured in step 1 in all bodily fluid samples. Then select as potential biomarker pairs of miRNA with a high positive correlation (r≥0.8), compare a ratio of miRNA concentrations in two subject cohorts for each selected miRNA pair and determine a miRNA pair as a suitable biomarker if this pair differentiates two subject cohorts with a statistically significant P-value.

Selection of miRNAs for biomarker pairs is an important step in developing screening, diagnostic and monitoring tests based on analysis of cell-free circulating miRNAs in bodily fluids. The present invention addresses this issue by providing the following methods for selection of effective biomarker pairs.

In one embodiment, the invention provides a method for selecting a biomarker miRNA pair for diagnosis and/or monitoring of a pathology, said method comprising the following steps:

(a) selecting at least four miRNAs known to be enriched in an organ affected by the pathology;
(b) measuring the level of each miRNA selected in step (a) in bodily fluid samples from two subject cohorts;
(c) calculating the mean level of each miRNA measured in step (b);
(d) calculating the difference between the mean miRNA levels calculated in step (c);
(e) comparing the differences between the mean miRNA levels calculated in step (d) between all studied miRNAs and selecting as potential biomarker pairs those miRNA pairs for which the difference calculated in step (d) for one miRNA is at least 1.5 times the difference calculated for the other miRNA;
(f) calculating Spearman's rank correlation coefficient (r) for each potential biomarker miRNA pair selected in step (e), and
(g) identifying the miRNA pair as a suitable biomarker pair for diagnosis and/or monitoring of said pathology if its (r) value calculated in step (f) is at least 0.8.

In another embodiment, the invention provides a method for selecting a biomarker miRNA pair for diagnosis and/or monitoring of a pathology, said method comprising the following steps:

(a) selecting at least four miRNAs known to be enriched in an organ affected by the pathology;
(b) measuring the level of each miRNA selected in step (a) in bodily fluid samples from two subject cohorts;
(c) calculating Spearman's rank correlation coefficient (r) for all possible pairs of individual miRNAs measured in step (b);
(d) selecting as potential biomarker pairs those miRNA pairs which have the (r) value calculated in step (c) of at least 0.8;
(e) calculating the mean level of each miRNA selected in step (d);
(f) calculating the difference between the mean miRNA levels calculated in step (e);
(g) identifying a miRNA pair as a suitable biomarker pair for diagnosis and/or monitoring of said pathology if the difference calculated in step (f) for one miRNA is at least 1.5 times the difference calculated for the other miRNA.

In a further embodiment, the invention provides a method for selecting a biomarker miRNA pair for diagnosis and/or monitoring of a pathology, said method comprising the following steps:

(a) selecting at least four miRNAs known to be enriched in an organ affected by the pathology;
(b) measuring the level of each miRNA selected in step (a) in bodily fluid samples from two subject cohorts;
(c) calculating Spearman's rank correlation coefficient (r) for all possible pairs of individual miRNAs measured in step (b);
(d) selecting as potential biomarker pairs those miRNA pairs which have the (r) value calculated in step (c) of at least 0.8;
(e) calculating P-value of two subject cohorts separation for each miRNA pair selected in step (d), and
(f) identifying a miRNA pair as a suitable biomarker pair for diagnosis and/or monitoring of said pathology if this pair differentiates two subject cohorts with a statistically significant P-value.

In another embodiment, the invention provides a computer-implemented method for selecting a biomarker miRNA pair for diagnosis and/or monitoring of a pathology, said method comprising the following steps:

(a) selecting a group of miRNAs known to be enriched in an organ affected by the pathology;
(b) measuring the level of each miRNA selected in step (a) in bodily fluid samples from two subject cohorts;
(c) electronically calculating the mean level of each miRNA measured in step (b);
(d) electronically calculating a difference between the mean miRNA levels calculated in step (c);
(e) selecting from the group of measured miRNAs a set of potential miRNA pairs each comprising a first miRNA and a second miRNA, wherein the calculated difference in the mean level in step (d) of the first miRNA is at least 1.5 times the calculated difference in the mean level of the second miRNA;
(f) electronically calculating the Spearman's rank correlation coefficient (r) for each potential miRNA pair selected in (e);
(g) selecting from the set of potential miRNA pairs those miRNA pairs, which are suitable for the diagnosis and/or monitoring of the pathology, wherein the (r) value calculated in step (f) is at least 0.8, and
(h) displaying all or part of the miRNA pairs selected in step (g).

In yet another embodiment, the invention provides a computer-implemented method for selecting a biomarker miRNA pair for diagnosis and/or monitoring of a pathology, said method comprising the following steps:

(a) selecting a group of miRNAs known to be enriched in an organ affected by the pathology;
(b) measuring the level of each miRNA selected in step (a) in bodily fluid samples from two subject cohorts;

(c) electronically calculating the Spearman's rank correlation coefficient (r) for all possible pairs of individual miRNAs measured in step (b);
(d) selecting from the group of measured miRNAs a set of potential biomarker miRNA pairs, wherein the (r) value calculated in step (c) is at least 0.8;
(e) electronically calculating the mean level of each miRNA selected in step (d);
(f) electronically calculating the difference between the mean miRNA levels calculated in step (e);
(g) selecting from the group of measured miRNAs a set of suitable miRNA biomarker pairs each comprising a first miRNA and a second miRNA, wherein for each suitable biomarker miRNA pair, the calculated difference in the mean level in step (f) of the first miRNA is at least 1.5 times the calculated difference in the mean level of the second miRNA, and
(h) displaying all or part of the suitable biomarker miRNA pairs selected in step (g).

In a further embodiment, the invention provides a computer-implemented method for selecting a biomarker miRNA pair for diagnosis and/or monitoring of a pathology, said method comprising the following steps:
(a) selecting a group of miRNAs known to be enriched in an organ affected by the pathology;
(b) measuring the level of each miRNA selected in step (a) in bodily fluid samples from two subject cohorts;
(c) electronically calculating the Spearman's rank correlation coefficient (r) of the levels measured in step (b) for all possible pairs of individual miRNAs;
(d) selecting from the group of measured miRNAs a set of potential biomarker miRNA pairs, wherein the (r) value calculated in step (c) is at least 0.8;
(e) electronically calculating P-value of two subject cohorts separation for each miRNA pair selected in step (d);
(f) selecting a miRNA pair as a suitable biomarker pair for diagnosis and/or monitoring of said pathology if this miRNA pair differentiates two subject cohorts with a statistically significant P-value, and
(g) displaying all or part of the suitable biomarker miRNA pairs selected in step (f).

Non-limiting examples of the methods which can be used to measure miRNA level in any of the above methods of the invention include, e.g., RT-PCR-based methods, miRNA array-based methods, new generation sequencing, and hybridization.

Non-limiting examples of the bodily fluid samples which can be used in any of the above methods of the invention include, e.g., plasma, serum, cerebrospinal fluid (CSF), urine, and saliva.

In any of the above methods of the invention, the subjects can be, e.g., humans or experimental animals.

In any of the above methods of the invention, any two cohorts can be compared. Non-limiting examples of such cohorts include, e.g., pathology versus control [e.g., age, gender and ethnicity-matched healthy subjects], one pathology of the organ versus another pathology of the same organ, two age groups, [e.g., 20-50 years old versus 60-80 years old], males versus females [e.g., age and ethnicity-matched], two different ethnic or racial groups [e.g., age and gender-matched], etc.).

Spearman's correlation algorithm used in the methods of the invention:

$$r = \frac{\Sigma_i (x_i - \bar{x})(y_i - \bar{y})}{\sqrt{\Sigma_i (x_i - \bar{x})^2 \Sigma_i (y_i - \bar{y})^2}},$$

wherein
$x_i$ is values of numerator miRNA;
$y_i$ is values of denominator miRNA;
$\bar{x}$ is mean of numerator values, and
$\bar{y}$ is mean of denominator values.

A minimal number of samples sufficient for obtaining a statistically significant difference between two cohorts in the above methods of the invention can be calculated by a standard formula for case-control study (see, e.g. Eng J. Radiology 2003, 227:309-313).

In the methods of the invention, a statistically significant P-value can be calculated using any method known in the art. Non-limiting examples of such methods are Student's t-test (for samples with normal distribution) and Mann-Whitney test (for samples with non-random distribution) (Mann and Whitney, Annals Math Stat. 1947, 18: 50-60). P-value≥0.05 is usually accepted as statistically significant. If numerous potential biomarkers are tested Bonferroni correction can be applied.

Diagnostic, Monitoring and Screening Methods of the Invention

The present invention provides novel highly sensitive and noninvasive or minimally invasive methods for diagnosing and monitoring Parkinson's Disease (PD) in a subject, said methods comprising determining the ratio of the levels in a bodily fluid sample from the subject (e.g., blood plasma, serum, urine, cerebrospinal fluid (CSF), saliva) of two or more specific miRNAs.

The use of specific miRNA pairs in the diagnostic methods of the invention allows for very high sensitivity and reliability and make possible early diagnosis of PD and distinguishing it from other neurodegenerative diseases and conditions (e.g., Mild Cognitive Impairment (MCI) and Alzheimer's disease (AD)). This approach also provides detailed and comprehensive information for monitoring PD development and treatment effectiveness, since various specific events in neurons (e.g., changes in miRNA profile, their secretion, neurite degradation, synapse loss, and finally neuronal death) can be detected and quantitated.

Non-limiting examples of miRNA pairs useful in the methods of the present invention include, e.g.:
miRNA Pairs for Detecting PD
Brain-Enriched:
let-7e/miR-335, miR-107/miR-335, miR-491-5p/miR-335, miR-744/miR-335, miR-99b/miR-335, let-7e/miR-9*, miR-491-5p/miR-9*, let-7e/miR-132, miR-107/miR-132, miR-491-5p/miR-132, let-7e/miR-134, miR-107/miR-134, miR-99b/miR-134, miR-491-5p/miR-134, let-7e/miR-323-3p, miR-107/miR-323-3p, miR-127/miR-323-3p, miR-181b/miR-323-3p, miR-99b/miR-323-3p, miR-491-5p/miR-323-3p, let-7e/miR-411, miR-107/miR-411, miR-491-5p/miR-411.
Inflammatory:
miR-155/miR-335, let-7e/miR-146b, miR-491-5p/miR-146a, let-7e/miR-146a, miR-744/miR-146a, miR-155/miR-16, miR-155/miR-132, miR-155/miR-323-3p, miR-155/miR-411, miR-491-5p/miR-146b, miR-155/miR-146a, miR-155/miR-146b.
miRNA Pairs for Differentiating PD and MCI
Brain-Enriched:
let-7e/miR-335, let-7e/miR-9*, miR-107/miR-335, miR-127/miR-323-3p, miR-491-5p/miR-335, miR-491-5p/miR-9*, miR-107/miR-9*, miR-744/miR-335, let-7e/miR-132, miR-107/miR-134, miR-181b/miR-132, let-7e/miR-210, miR-181b/miR-9*, miR-181a/miR-335, miR-491-5p/miR- 134, let-7e/miR-874, miR-181b/miR-874, miR-107/miR-132, miR-491-5p/miR-132, miR-107/miR-323-3p, miR-127/miR-134, miR-491-5p/miR-874, miR-491-5p/miR-323-3p, miR-127/miR-432, let-7e/miR-134, let-7e/miR-411, miR-107/miR-411, miR-491-5p/miR-411, miR-107/miR-874, miR-181a/miR-9*, miR-491-5p/miR-210, miR-181b/miR-335, miR-99b/miR-335, miR-107/miR-210, miR-127/487b, miR-181a/miR-874, miR-9/miR-9*, miR-107/miR-487b, miR-107/miR-432, miR-9/miR-335, miR-181a/miR-132, miR-181b/miR-210, miR-99b/miR-132.

Inflammatory:
let-7e/miR-146a, miR-107/miR-146a, miR-491-5p/miR-146a, miR-107/miR-146b, miR-491-5p/miR-146b, miR-155/miR-874, let-7e/miR-146b, miR-155/miR-9*, miR-155/miR-335, miR-155/miR-411, miR-744/miR-146a.

miRNA Pairs for Differentiating PD and AD
Brain-Enriched:
let-7e/miR-335, miR-107/miR-335, miR-127/miR-323-3p, let-7e/miR-411, miR-99b/miR-335, miR-491-5p/miR-335, miR-127/miR-134, miR-744/miR-335, miR-9/miR-335, miR-181b/miR-335, miR-107/miR-411, miR-181a/miR-335, let-7e/miR-9*, miR-491-5p/miR-411, let-7e/miR-132, miR-181b/miR-132, miR-9/miR-9*, miR-9/miR-134, miR-107/miR-134, miR-181b/miR-874, let-7e/miR-134, miR-107/miR-132, miR-107/miR-9*, miR-127/miR-335, miR-9/miR-132, miR-181b/miR-9*, miR-491-5p/miR-132, let-7e/miR-210, miR-491-5p/miR-9*, miR-107/miR-323-3p, miR-491-5p/miR-323-3p, miR-491-5p/miR-134, let-7e/miR-874, miR-181b/miR-210, miR-9/miR-874, miR-9/miR-485-3p, miR-744/miR-134, miR-181b/miR-323-3p.

Inflammatory:
miR-107/miR-146a, miR-491-5p/miR-146a, miR-155/miR-132, miR-155/miR-335, miR-107/miR-146b, miR-491-5p/miR-146b, miR-9/miR-146a, let-7e/miR-146b, miR-9/miR-146b, let-7e/miR-146a, miR-155/miR-874, miR-155/miR-9*, miR-744/miR-146a, miR-155/miR-210, miR-155/miR-146b, miR-744/miR-146b, miR-155/miR-146a, miR-155/miR-134, miR-155/miR-411, miR-181b/miR-146b.

In one aspect, the invention provides a method for detecting a first neurodegenerative disease in a subject, which method comprises:
a) measuring the level of a first brain-enriched miRNA in a bodily fluid sample collected from the subject, wherein said first brain-enriched miRNA is enriched in a brain area(s) affected by the first neurodegenerative disease;
b) measuring the level of a second brain-enriched miRNA in the same bodily fluid sample collected from the subject, wherein said second brain-enriched miRNA (i) is enriched in a brain area(s) which is not affected by the first neurodegenerative disease, or (ii) is enriched in a brain cell type which is not affected by the first neurodegenerative disease, or (iii) is enriched in the same brain area as the first miRNA, but its expression and/or secretion change differently than expression and/or secretion of the first miRNA during development of the first neurodegenerative disease;
c) calculating the ratio of the levels of the miRNAs measured in steps (a) and (b);
d) comparing the ratio of the levels of the miRNAs calculated in step (c) with a corresponding control ratio, and
e) (i) identifying the subject as being afflicted with the first neurodegenerative disease when the ratio of the levels of the miRNAs calculated in step (c) is higher than the corresponding control ratio or (ii) identifying the subject as not being afflicted with the first neurodegenerative disease when the ratio of the levels of the miRNA calculated in step (c) is not higher than the corresponding control ratio.

In a related aspect, the invention provides a method for detecting a first neurodegenerative disease in a subject, which method comprises:
a) measuring the level of a first miRNA in a bodily fluid sample collected from the subject, wherein said first miRNA (i) is enriched in a brain area(s) affected by the first neurodegenerative disease or (ii) is an inflammation-associated miRNA;
b) measuring the level of a second miRNA in the same bodily fluid sample collected from the subject, wherein said second miRNA (i) is an inflammation-associated miRNA if the first miRNA is a brain-enriched miRNA or (ii) is a brain-enriched miRNA if the first miRNA is an inflammation-associated miRNA;
c) calculating the ratio of the levels of the miRNAs measured in steps (a) and (b);
d) comparing the ratio of the levels of the miRNAs calculated in step (c) with a corresponding control ratio, and
e) (i) identifying the subject as being afflicted with the first neurodegenerative disease when the ratio of the levels of the miRNAs calculated in step (c) is higher than the corresponding control ratio or (ii) identifying the subject as not being afflicted with the first neurodegenerative disease when the ratio of the levels of the miRNA calculated in step (c) is not higher than the corresponding control ratio.

In one embodiment of the above two methods, the method further comprises refining the diagnosis by the following steps, which steps can be performed simultaneously or sequentially with each other and/or with the steps (d)-(e) of the above two methods:
f) comparing the ratio of the levels of the miRNAs calculated in step (c) with the standard range of ratios of said miRNAs characteristic of a second neurodegenerative disease, and
g) (i) excluding the diagnosis of the second neurodegenerative disease in the subject if the ratio of the levels of the miRNAs calculated in step (c) does not fall within the standard range of ratios of said miRNAs characteristic of the second neurodegenerative disease, or (ii) not excluding the diagnosis of the second neurodegenerative disease in the subject if the ratio of the levels of the miRNAs calculated in step (c) falls within the standard range of ratios of said miRNAs characteristic of the second neurodegenerative disease.

In one embodiment of the above two methods, the method further comprises refining the diagnosis by the following steps, which steps can be performed simultaneously or sequentially with each other and/or with the steps (a)-(e) of the above two methods:
f) measuring the level of a third brain-enriched miRNA in the same bodily fluid sample collected from the subject, wherein said third brain-enriched miRNA is enriched in a brain area(s) affected by a second neurodegenerative disease;
g) measuring the level of a fourth brain-enriched miRNA in the same bodily fluid sample collected from the subject, wherein said fourth brain-enriched miRNA is (i) enriched in a brain area(s) which is not affected by the second neurodegenerative disease, or (ii) is enriched in a brain cell type which is not affected by the second neurodegenerative disease, or (iii) is enriched in the same brain area as the third miRNA, but its expression and/or secretion change differently than expression and/or secretion of the third miRNA during development of the second neurodegenerative disease;
h) calculating the ratio of the levels of the miRNAs measured in steps (f) and (g);

i) comparing the ratio of the levels of the miRNAs calculated in step (h) with the standard range of ratios of said miRNAs characteristic of the second neurodegenerative disease;
j) (i) identifying the subject as being afflicted with the second neurodegenerative disease in addition to the first neurodegenerative disease if the ratio of the levels of the miRNAs calculated in step (h) falls within the standard range of ratios of said miRNAs characteristic of the second neurodegenerative disease, or (ii) excluding the diagnosis of the second neurodegenerative disease in the subject if the ratio of the levels of the miRNAs calculated in step (h) does not fall within the standard range of ratios of said miRNAs characteristic of the second neurodegenerative disease.

In one embodiment of any of the above methods, said first neurodegenerative disease is Parkinson's disease (PD).

In one embodiment of the above disease differentiation methods, said first neurodegenerative disease is Parkinson's disease (PD) and said second neurodegenerative disease is selected from the group consisting of Alzheimer's disease (AD), Mild Cognitive Impairment (MCI), Huntington's disease (HD), prion-caused diseases, frontotemporal dementia (FTD), Lewy body dementia, vascular dementias, Amyotrophic Later Sclerosis (ALS), chronic traumatic encephalopathy (CTE), progressive supranuclear palsy (PSP), multiple system atrophy (MSA), corticobasal degeneration (CBGD), Pick's disease, and olivopontocerebellar atrophy (OPCA).

In one aspect, the invention provides a method for detecting Parkinson's disease (PD) in a subject, which method comprises:
a) measuring the level of a first brain-enriched miRNA in a bodily fluid sample collected from the subject, wherein said first brain-enriched miRNA is neuronal miRNA enriched in midbrain and/or frontal cortex;
b) measuring the level of a second brain-enriched miRNA in the same bodily fluid sample collected from the subject, wherein said second brain-enriched miRNA is (i) enriched in a brain area(s) which is not affected by PD, or (ii) is enriched in a brain cell type which is not affected by PD, or (iii) is enriched in the same brain area as the first miRNA, but its expression and/or secretion change differently than expression and/or secretion of the first miRNA during PD development;
c) calculating the ratio of the levels of the miRNA measured in steps (a) and (b);
d) comparing the ratio of the levels of the miRNA calculated in step (c) with a corresponding control ratio, and
e) (i) identifying the subject as being afflicted with PD when the ratio of the levels of the miRNA calculated in step (c) is higher than the corresponding control ratio or (ii) identifying the subject as not being afflicted with PD when the ratio of the levels of the miRNA calculated in step (c) is not higher than the corresponding control ratio.

In a related aspect, the invention provides a method for detecting Parkinson's disease (PD) in a subject, which method comprises:
a) measuring the level of a first miRNA in a bodily fluid sample collected from the subject, wherein said first miRNA is (i) a brain-enriched neuronal miRNA enriched in midbrain and/or frontal cortex or is (ii) an inflammation-associated miRNA;
b) measuring the level of a second miRNA in the same bodily fluid sample collected from the subject, wherein said second miRNA is (i) an inflammation-associated miRNA if the first miRNA is a brain-enriched miRNA or is (ii) a brain-enriched miRNA if the first miRNA is an inflammation-associated miRNA;
c) calculating the ratio of the levels of the miRNA measured in steps (a) and (b);
d) comparing the ratio of the levels of the miRNA calculated in step (c) with a corresponding control ratio, and
e) (i) identifying the subject as being afflicted with PD when the ratio of the levels of the miRNA calculated in step (c) is higher than the corresponding control ratio or (ii) identifying the subject as not being afflicted with PD when the ratio of the levels of the miRNA calculated in step (c) is not higher than the corresponding control ratio.

In one embodiment of the above two methods for detecting PD, the method further comprises refining the diagnosis by the following steps, which steps can be performed simultaneously or sequentially with each other and with the steps (d)-(e) of the above two methods for detecting PD:
f) comparing the ratio of the levels of the miRNAs calculated in step (c) with the standard range of ratios of said miRNAs characteristic of a second neurodegenerative disease different from PD;
g) (i) excluding the diagnosis of the second neurodegenerative disease in the subject if the ratio of the levels of the miRNAs calculated in step (c) does not fall within the standard range of ratios of said miRNAs characteristic of the second neurodegenerative disease, or (ii) not excluding the diagnosis of the second neurodegenerative disease if the ratio of the levels of the miRNAs calculated in step (c) falls within the standard range of ratios of said miRNAs characteristic of the second neurodegenerative disease.

In one embodiment of the above two methods for detecting PD, the method further comprises refining the diagnosis by the following steps, which steps can be performed simultaneously or sequentially with each other and with the steps (a)-(e) of the above two methods for detecting PD:
f) measuring the level of a third brain-enriched miRNA in the same bodily fluid sample collected from the subject, wherein said third brain-enriched miRNA is enriched in a brain area(s) affected by a second neurodegenerative disease and is a pre-identified numerator in biomarker miRNA pair for said second neurodegenerative disease;
g) measuring the level of a fourth brain-enriched miRNA in the same bodily fluid sample collected from the subject, wherein said fourth brain-enriched miRNA is and is a pre-identified denominator in biomarker miRNA pair for said second neurodegenerative disease and is (i) enriched in a brain area(s) which is not affected by the second neurodegenerative disease, or (ii) is enriched in a brain cell type which is not affected by the second neurodegenerative disease and is different from the cell type where the third miRNA is enriched, or (iii) is enriched in the same brain area as the third miRNA, but its expression and/or secretion change differently than expression and/or secretion of the third miRNA during development of the second neurodegenerative disease;
h) calculating the ratio of the levels of the miRNAs measured in steps (f) and (g);
i) comparing the ratio of the levels of the miRNAs calculated in step (h) with the standard range of ratios of said miRNAs characteristic of the second neurodegenerative disease;
j) (i) identifying the subject as being afflicted with the second neurodegenerative disease in addition to PD if the ratio of the levels of the miRNAs calculated in step (h) falls within the standard range of ratios of said miRNAs characteristic of the second neurodegenerative disease, or (ii) excluding the diagnosis of the second neurodegenerative disease in the subject if the ratio of the levels of the miRNAs calculated in step (h) does not fall within the standard range of ratios of said miRNAs characteristic of the second neurodegenerative disease.

In one embodiment of any of the above methods of disease detection, the control ratio is a predetermined value which represents a statistically validated threshold ratio of the levels of said first and second miRNAs (a single "cut-off" value) equal to the highest possible value within the range of corresponding values in age-matched (e.g., ±2.5 years) healthy subjects. Such statistically validated threshold ("cut-off" value) may be established by assaying a large cohort of healthy individuals in the select age-matched population and using a suitable statistical model (see, e.g., Knapp, R. G., and Miller, M. E. (1992) Clinical Epidemiology and Biostatistics, William and Wilkins, Harual Publishing Co. Malvern, Pa.). In another embodiment of any of the above methods of disease detection, the control ratio is the ratio of the levels of said first and second miRNAs in a similarly processed bodily fluid sample from the same subject collected in the past.

Since pathological processes characteristic of various neurodegenerative diseases are often observed in the brain of the same patient (Hu W T et al. Acta Neuropathol. 2010; 120: 385-399; Farlow M R et al. Dement. Geriatr. Cogn. Disord. Extra 2013; 3: 281-290; Stern R A et al. 2011; 3: S460-S467; Costanza A. et al. Neuropathol. 2011; 37: 570-584), the present invention also provides methods for differential diagnosis, which can involve the use of two or more different biomarker pairs and exclude the presence of an additional pathology or demonstrates simultaneous presence of such additional pathology (i.e., mixed pathology).

In the diagnostic methods of the invention, in order to further refine the diagnosis and differentiate between PD and other neurodegenerative diseases (such as, e.g., Alzheimer's disease (AD), Mild Cognitive Impairment (MCI), Huntington's disease (HD), prion-caused diseases, frontotemporal dementia (FTD), Lewy body dementia, vascular dementias, Amyotrophic Later Sclerosis (ALS), Chronic Traumatic Encephalopathy (CTE), progressive supranuclear palsy (PSP), multiple system atrophy (MSA), corticobasal degeneration (CBGD), Pick's disease, and olivopontocerebellar atrophy (OPCA)) the ratio of the levels of the miRNAs within the biomarker pair in the subject's sample is being compared to the standard range of ratios of the levels of the same miRNAs found in subjects (preferably age-matched, e.g., ±2.5 years) having PD or a different neurodegenerative disease. Such "refining" comparison can be performed either after the initial diagnosis (i.e., comparison with a healthy control threshold) or simultaneously with such initial diagnosis. Such "refining" comparison can be performed simultaneously for several different diseases or sequentially. The disease-specific standard range of ratios used in the "refining" comparison is usually a statistically validated predetermined range of values which may be established by assaying a large cohort of individuals diagnosed with a specific neurodegenerative disease in the select population (preferably age-matched, e.g., ±2.5 years) and using a statistical model. A further "refining" to determine not only the specific disease but the extent of progression of such disease can be performed by using standard disease stage-specific ratio ranges for comparison (said standard ranges being established by assaying a large cohort of individuals diagnosed with a specific stage of a specific neurodegenerative disease).

In another aspect, the invention provides a method for monitoring changes in development of a neurodegenerative disease in a subject (e.g., a subject who had been previously diagnosed with said neurodegenerative disease), which method comprises:

a) measuring the level of a first brain-enriched miRNA in two or more bodily fluid samples collected from the subject, wherein said first brain-enriched miRNA is enriched in a brain area(s) affected by the neurodegenerative disease;

b) measuring the level of a second brain-enriched miRNA in the same bodily fluids samples as in step (a), wherein said second brain-enriched miRNA (i) is enriched in a brain area(s) which is not affected by the neurodegenerative disease, or (ii) is enriched in a brain cell type which is not affected by the neurodegenerative disease, or (iii) is enriched in the same brain area as the first miRNA, but its expression and/or secretion change differently than expression and/or secretion of the first miRNA during development of the neurodegenerative disease;

c) calculating the ratio of the levels of the miRNA measured in steps (a) and (b) for each bodily fluid sample;

d) comparing the ratios of the levels of the miRNA calculated in step (c) between the earlier collected and later collected bodily fluid sample(s), and e) (i) determining that the neurodegenerative disease in the subject has progressed if the ratio of the levels of the miRNA calculated in step (c) is increased in the later collected bodily fluid sample(s) as compared to the earlier collected sample(s), or (ii) determining that the neurodegenerative disease in the subject has not progressed if the ratio of the levels of the miRNA calculated in step (c) is not changed in the later collected bodily fluid sample(s) as compared to the earlier collected sample(s).

In a related aspect, the invention provides a method for monitoring changes in development of a neurodegenerative disease in a subject (e.g., a subject who had been previously diagnosed with said neurodegenerative disease), which method comprises:

a) measuring the level of a first miRNA in two or more bodily fluid samples collected from the subject, wherein said first miRNA (i) is enriched in a brain area(s) affected by the first neurodegenerative disease or (ii) is an inflammation-associated miRNA;

b) measuring the level of a second miRNA in the same bodily fluids samples as in step (a), wherein said second miRNA (i) is an inflammation-associated miRNA if the first miRNA is a brain-enriched miRNA or (ii) is a brain-enriched miRNA if the first miRNA is an inflammation-associated miRNA;

c) calculating the ratio of the levels of the miRNA measured in steps (a) and (b) for each bodily fluid sample;

d) comparing the ratios of the levels of the miRNA calculated in step (c) between the earlier collected and later collected bodily fluid sample(s), and e) (i) determining that the neurodegenerative disease in the subject has progressed if the ratio of the levels of the miRNA calculated in step (c) is increased in the later collected bodily fluid sample(s) as compared to the earlier collected sample(s), or (ii) determining that the neurodegenerative disease in the subject has not progressed if the ratio of the levels of the miRNA calculated in step (c) is not changed in the later collected bodily fluid sample(s) as compared to the earlier collected sample(s).

In a related aspect, the invention provides a method for monitoring changes in development of Parkinson's disease (PD) in a subject (e.g., a subject who had been previously diagnosed with PD), which method comprises:

a) measuring the level of a first brain-enriched miRNA in two or more bodily fluid samples collected from the subject, wherein the samples have been collected at spaced apart time points, and wherein said first brain-enriched miRNA is enriched in midbrain and/or frontal cortex;
b) measuring the level of a second brain-enriched miRNA in the same bodily fluid samples as in step (a), wherein said second brain-enriched miRNA is (i) enriched in brain areas which are not affected by PD, or (ii) is enriched in a brain cell type which is not affected by PD, or (iii) is enriched in the same brain area as the first brain-enriched miRNA, but its expression and/or secretion change differently than expression and/or secretion of the first brain-enriched miRNA during PD development;
c) calculating the ratio of the levels of the miRNA measured in steps (a) and (b) for each bodily fluid sample;
d) comparing the ratios of the levels of the miRNA calculated in step (c) between the earlier collected and later collected bodily fluid sample(s), and
e) (i) determining that PD in the subject has progressed if the ratio of the levels of the miRNA calculated in step (c) is increased in the later collected bodily fluid sample(s) as compared to the earlier collected sample(s), or (ii) determining that PD in the subject has not progressed if the ratio of the levels of the miRNA calculated in step (c) is not changed in the later collected bodily fluid sample(s) as compared to the earlier collected sample(s).

In another related aspect, the invention provides a method for monitoring changes in development of Parkinson's disease (PD) in a subject (e.g., a subject who had been previously diagnosed with PD), which method comprises:
a) measuring the level of a first miRNA in two or more bodily fluid samples collected from the subject, wherein the samples have been collected at spaced apart time points, and wherein said first miRNA is (i) a brain-enriched neuronal miRNA enriched in midbrain and/or frontal cortex or is (ii) an inflammation-associated miRNA;
b) measuring the level of a second miRNA in the same bodily fluid samples as in step (a), wherein said second miRNA is (i) an inflammation-associated miRNA if the first miRNA is a brain-enriched miRNA or is (ii) a brain-enriched miRNA if the first miRNA is an inflammation-associated miRNA;
c) calculating the ratio of the levels of the miRNA measured in steps (a) and (b) for each bodily fluid sample;
d) comparing the ratios of the levels of the miRNA calculated in step (c) between the earlier collected and later collected bodily fluid sample(s), and
e) (i) determining that PD in the subject has progressed if the ratio of the levels of the miRNA calculated in step (c) is increased in the later collected bodily fluid sample(s) as compared to the earlier collected sample(s), or (ii) determining that PD in the subject has not progressed if the ratio of the levels of the miRNA calculated in step (c) is not changed in the later collected bodily fluid sample(s) as compared to the earlier collected sample(s).

In a separate aspect, the invention provides a method for monitoring the effect of a treatment on development of a neurodegenerative disease in a subject who had been previously diagnosed with said neurodegenerative disease, which method comprises:
a) measuring the level of a first brain-enriched miRNA in a bodily fluid sample collected from the subject prior to initiation of the treatment, wherein said first brain-enriched miRNA is enriched in a brain area(s) affected by the neurodegenerative disease;
b) measuring the level of a second brain-enriched miRNA in the same bodily fluid sample collected from the subject, wherein said second brain-enriched miRNA (i) is enriched in a brain area(s) which is not affected by the neurodegenerative disease, or (ii) is enriched in a brain cell type which is not affected by the neurodegenerative disease, or (iii) is enriched in the same brain area as the first miRNA, but its expression and/or secretion change differently than expression and/or secretion of the first miRNA during development of the neurodegenerative disease;
c) calculating the ratio of the levels of the miRNA measured in steps (a) and (b);
d) measuring the level of the same first miRNA as in step (a) in one or more bodily fluid sample(s) collected from the subject in the course of or following the treatment;
e) measuring the level of the same second miRNA as in step (b) in the same bodily fluid sample(s) as in step (d);
f) calculating the ratio of the levels of the miRNA measured in steps (d) and (e) for each bodily fluid sample;
g) comparing the ratios of the levels of the miRNA calculated in steps (c) and (f), and optionally comparing the ratios of the levels of the miRNA calculated in step (f) between different samples in step (d), and
h) (i) determining that the treatment is effective for said neurodegenerative disease if the ratio of the levels of the miRNA calculated in step (c) is higher than the corresponding ratio(s) calculated in step (f), or (ii) determining that the treatment is not effective for said neurodegenerative disease if the ratio of the levels of the miRNA calculated in step (c) is not higher than the corresponding ratio(s) calculated in step (f).

In a related aspect, the invention provides a method for monitoring the effect of a treatment on development of a neurodegenerative disease in a subject who had been previously diagnosed with said neurodegenerative disease, which method comprises:
a) measuring the level of a first miRNA in a bodily fluid sample collected from the subject prior to initiation of the treatment, wherein said first miRNA (i) is enriched in a brain area(s) affected by the first neurodegenerative disease or (ii) is an inflammation-associated miRNA;
b) measuring the level of a second miRNA in the same bodily fluid sample collected from the subject, wherein said second miRNA (i) is an inflammation-associated miRNA if the first miRNA is a brain-enriched miRNA or (ii) is a brain-enriched miRNA if the first miRNA is an inflammation-associated miRNA;
c) calculating the ratio of the levels of the miRNA measured in steps (a) and (b);
d) measuring the level of the same first miRNA as in step (a) in one or more bodily fluid sample(s) collected from the subject in the course of or following the treatment;
e) measuring the level of the same second miRNA as in step (b) in the same bodily fluid sample(s) as in step (d);
f) calculating the ratio of the levels of the miRNA measured in steps (d) and (e) for each bodily fluid sample;
g) comparing the ratios of the levels of the miRNA calculated in steps (c) and (f), and optionally comparing the ratios of the levels of the miRNA calculated in step (f) between different samples in step (d), and
h) (i) determining that the treatment is effective for said neurodegenerative disease if the ratio of the levels of the miRNA calculated in step (c) is higher than the corresponding ratio(s) calculated in step (f), or (ii) determining that the treatment is not effective for said neurodegenerative disease if the ratio of the levels of the miRNA calculated in step (c) is not higher than the corresponding ratio(s) calculated in step (f).

In another related aspect, the invention provides a method for monitoring the effect of a treatment on development of Parkinson's disease (PD) in a subject who had been previously diagnosed with PD, which method comprises:

a) measuring the level of a first brain-enriched miRNA in a bodily fluid sample collected from the subject prior to initiation of the treatment, wherein said first miRNA is enriched in midbrain and/or frontal cortex;

b) measuring the level of a second brain-enriched miRNA in the same bodily fluid sample collected from the subject, wherein said second miRNA is (i) enriched in brain areas which are not affected by PD, or (ii) is enriched in a brain cell type which is not affected by PD, or (iii) is enriched in the same brain area as the first miRNA, but its expression and/or secretion change differently than expression and/or secretion of the first miRNA during PD development;

c) calculating the ratio of the levels of the miRNA measured in steps (a) and (b);

d) measuring the level of the same first miRNA as in step (a) in one or more bodily fluid sample(s) collected from the subject in the course of or following the treatment;

e) measuring the level of the same second miRNA as in step (b) in the same bodily fluid sample(s) as in step (d);

f) calculating the ratio of the levels of the miRNA measured in steps (d) and (e) for each bodily fluid sample;

g) comparing the ratios of the levels of the miRNA calculated in steps (c) and (f), and optionally comparing the ratios of the levels of the miRNA calculated in step (f) between different samples in step (d), and h) (i) determining that the PD treatment is effective if the ratio of the levels of the miRNA calculated in step (c) is higher than the corresponding ratio(s) calculated in step (f), or (ii) determining that the PD treatment is not effective if the ratio of the levels of the miRNA calculated in step (c) is not higher than the corresponding ratio(s) calculated in step (f).

In yet another related aspect, the invention provides a method for monitoring the effect of a treatment on development of Parkinson's disease (PD) in a subject who had been previously diagnosed with PD, which method comprises:

a) measuring the level of a first miRNA in a bodily fluid sample collected from the subject prior to initiation of the treatment, wherein said first miRNA is (i) a brain-enriched neuronal miRNA enriched in midbrain and/or frontal cortex or is (ii) an inflammation-associated miRNA;

b) measuring the level of a second miRNA in the same bodily fluid sample collected from the subject, wherein said second miRNA is (i) an inflammation-associated miRNA if the first miRNA is a brain-enriched miRNA or is (ii) a brain-enriched miRNA if the first miRNA is an inflammation-associated miRNA;

c) calculating the ratio of the levels of the miRNA measured in steps (a) and (b);

d) measuring the level of the same first miRNA as in step (a) in one or more bodily fluid sample(s) collected from the subject in the course of or following the treatment;

e) measuring the level of the same second miRNA as in step (b) in the same bodily fluid sample(s) as in step (d);

f) calculating the ratio of the levels of the miRNA measured in steps (d) and (e) for each bodily fluid sample;

g) comparing the ratios of the levels of the miRNA calculated in steps (c) and (f), and optionally comparing the ratios of the levels of the miRNA calculated in step (f) between different samples in step (d), and h) (i) determining that the PD treatment is effective if the ratio of the levels of the miRNA calculated in step (c) is higher than the corresponding ratio(s) calculated in step (f), or (ii) determining that the PD treatment is not effective if the ratio of the levels of the miRNA calculated in step (c) is not higher than the corresponding ratio(s) calculated in step (f).

In a separate aspect, the invention provides a method for identifying a compound useful for slowing down the progression or treating a neurodegenerative disease in a subject who had been previously diagnosed with said neurodegenerative disease, which method comprises:

a) measuring the level of a first brain-enriched miRNA in a bodily fluid sample, wherein said bodily fluid sample(s) is collected from the subject prior to test compound administration, and wherein said first brain-enriched miRNA is enriched in a brain area(s) affected by the neurodegenerative disease;

b) measuring the level of a second brain-enriched miRNA in the same bodily fluid sample collected from the subject, wherein said second brain-enriched miRNA (i) is enriched in a brain area(s) which is not affected by the neurodegenerative disease, or (ii) is enriched in a brain cell type which is not affected by the neurodegenerative disease, or (iii) is enriched in the same brain area as the first miRNA, but its expression and/or secretion change differently than expression and/or secretion of the first miRNA during development of the neurodegenerative disease;

c) calculating the ratio of the levels of the miRNA measured in steps (a) and (b);

d) measuring the level of the same first miRNA as in step (a) in one or more bodily fluid samples collected from the subject following administration of a test compound;

e) measuring the level of the same second miRNA as in step (b) in the same bodily fluid sample(s) as in step (d);

f) calculating the ratio of the levels of the miRNAs measured in steps (d) and (e) for each of the bodily fluid samples collected from the subject following administration of the test compound;

g) comparing the ratio of the levels of the miRNA calculated in steps (c) and (f), and h) (i) identifying that the test compound is useful for slowing down the progression or treating the neurodegenerative disease if the ratio of the levels of the miRNA calculated in step (f) is lower than the ratio of the levels of the miRNA calculated in step (c); (ii) identifying that the test compound is not useful for slowing down the progression or treating the neurodegenerative disease if the ratio of the levels of the miRNA calculated in step (f) is not lower than the ratio of the levels of the miRNAs calculated in step (c).

In a related aspect, the invention provides a method for identifying a compound useful for slowing down the progression or treating a neurodegenerative disease in a subject who had been previously diagnosed with said neurodegenerative disease, which method comprises:

a) measuring the level of a first miRNA in a bodily fluid sample, wherein said bodily fluid sample(s) is collected from the subject prior to test compound administration, and wherein said first miRNA (i) is enriched in a brain area(s) affected by the first neurodegenerative disease or (ii) is an inflammation-associated miRNA;

b) measuring the level of a second miRNA in the same bodily fluid sample collected from the subject, wherein said second miRNA (i) is an inflammation-associated miRNA if the first miRNA is a brain-enriched miRNA or (ii) is a brain-enriched miRNA if the first miRNA is an inflammation-associated miRNA;

c) calculating the ratio of the levels of the miRNA measured in steps (a) and (b);

d) measuring the level of the same first miRNA as in step (a) in one or more bodily fluid samples collected from the subject following administration of a test compound;
e) measuring the level of the same second miRNA as in step (b) in the same bodily fluid sample(s) as in step (d);
f) calculating the ratio of the levels of the miRNAs measured in steps (d) and (e) for each of the bodily fluid samples collected from the subject following administration of the test compound;
g) comparing the ratio of the levels of the miRNA calculated in steps (c) and (f), and
h) (i) identifying that the test compound is useful for slowing down the progression or treating the neurodegenerative disease if the ratio of the levels of the miRNA calculated in step (f) is lower than the ratio of the levels of the miRNA calculated in step (c); (ii) identifying that the test compound is not useful for slowing down the progression or treating the neurodegenerative disease if the ratio of the levels of the miRNA calculated in step (f) is not lower than the ratio of the levels of the miRNAs calculated in step (c).

In another related aspect, the invention provides a method for identifying a compound useful for slowing down the progression or treating Parkinson's disease (PD) in a subject who had been previously diagnosed with PD, which method comprises:
a) measuring the level of a first brain-enriched miRNA in a bodily fluid sample, wherein said bodily fluid sample(s) is collected from the subject prior to test compound administration, and wherein said first miRNA is enriched in midbrain and/or frontal cortex;
b) measuring the level of a second brain-enriched miRNA in the same bodily fluid sample collected from the subject, wherein said second miRNA is (i) enriched in brain areas which are not affected by PD, or (ii) is enriched in a brain cell type which is not affected by PD, or (iii) is enriched in the same brain area as the first miRNA, but its expression and/or secretion change differently than expression and/or secretion of the first miRNA during PD development;
c) calculating the ratio of the levels of the miRNA measured in steps (a) and (b);
d) measuring the level of the same first miRNA as in step (a) in one or more bodily fluid samples collected from the subject following administration of a test compound;
e) measuring the level of the same second miRNA as in step (b) in the same bodily fluid sample(s) as in step (d);
f) calculating the ratio of the levels of the miRNAs measured in steps (d) and (e) for each of the bodily fluid samples collected from the subject following administration of the test compound;
g) comparing the ratio of the levels of the miRNA calculated in steps (c) and (f), and
h) (i) identifying that the test compound is useful for slowing down the progression or treating PD if the ratio of the levels of the miRNA calculated in step (f) is lower than the ratio of the levels of the miRNA calculated in step (c); (ii) identifying that the test compound is not useful for slowing down the progression or treating PD if the ratio of the levels of the miRNA calculated in step (f) is not lower than the ratio of the levels of the miRNAs calculated in step (c).

In yet another related aspect, the invention provides a method for identifying a compound useful for slowing down the progression or treating Parkinson's disease (PD) in a subject who had been previously diagnosed with PD, which method comprises:
a) measuring the level of a first miRNA in a bodily fluid sample, wherein said bodily fluid sample(s) is collected from the subject prior to test compound administration, and wherein said first miRNA is (i) a brain-enriched neuronal miRNA enriched in midbrain and/or frontal cortex or is (ii) an inflammation-associated miRNA;
b) measuring the level of a second miRNA in the same bodily fluid sample collected from the subject, wherein said second miRNA is (i) an inflammation-associated miRNA if the first miRNA is a brain-enriched miRNA or is (ii) a brain-enriched miRNA if the first miRNA is an inflammation-associated miRNA;
c) calculating the ratio of the levels of the miRNA measured in steps (a) and (b);
d) measuring the level of the same first miRNA as in step (a) in one or more bodily fluid samples collected from the subject following administration of a test compound;
e) measuring the level of the same second miRNA as in step (b) in the same bodily fluid sample(s) as in step (d);
f) calculating the ratio of the levels of the miRNAs measured in steps (d) and (e) for each of the bodily fluid samples collected from the subject following administration of the test compound;
g) comparing the ratio of the levels of the miRNA calculated in steps (c) and (f), and
h) (i) identifying that the test compound is useful for slowing down the progression or treating PD if the ratio of the levels of the miRNA calculated in step (f) is lower than the ratio of the levels of the miRNA calculated in step (c); (ii) identifying that the test compound is not useful for slowing down the progression or treating PD if the ratio of the levels of the miRNA calculated in step (f) is not lower than the ratio of the levels of the miRNAs calculated in step (c).

The methods of the instant invention are based on measurement of levels of certain miRNAs in bodily fluids. The use of bodily fluids that can be collected by non-invasive or minimally invasive techniques (e.g., as opposed to detection in the brain) allows for a cost effective and minimally invasive or noninvasive diagnostic procedure. Preferred bodily fluids for use in the methods of the invention are blood plasma, serum, urine, cerebrospinal fluid (CSF), and saliva. However, any other bodily fluid can also be used.

Examples of useful methods for measuring miRNA level in bodily fluids include hybridization with selective probes (e.g., using Northern blotting, bead-based flow-cytometry, oligonucleotide microchip [microarray], or solution hybridization assays such as Ambion mirVana miRNA Detection Kit), polymerase chain reaction (PCR)-based detection (e.g., stem-loop reverse transcription-polymerase chain reaction [RT-PCR], quantitative RT-PCR based array method [qPCR-array]), direct sequencing by one of the next generation sequencing technologies (e.g., Helicos small RNA sequencing, miRNA BeadArray (Illumina), Roche 454 (FLX-Titanium), and ABI SOLiD), or various microfluidic technologies. For review of additional applicable techniques see, e.g., Chen et al., BMC Genomics, 2009, 10:407; Kong et al., J Cell Physiol. 2009; 218:22-25. One of the preferred types of techniques are RT-PCR-based techniques as such techniques allow to achieve good sensitivity and specificity.

In some embodiments, miRNAs are purified prior to quantification. miRNAs can be isolated and purified from bodily fluids by various methods, including the use of commercial kits (e.g., miRNeasy kit [Qiagen], MirVana RNA isolation kit [Ambion/ABI], miRACLE [Agilent], High Pure miRNA isolation kit [Roche], and miRNA Purification kit [Norgen Biotek Corp.]), Trizol extraction (see Example 1, below), concentration and purification on anionexchangers, magnetic beads covered by RNA-binding substances, or adsorption of certain miRNA on complementary oligonucleotides.

In some embodiments, miRNA degradation in bodily fluid samples and/or during miRNA purification is reduced or eliminated. Useful methods for reducing or eliminating miRNA degradation include, without limitation, adding RNase inhibitors (e.g., RNasin Plus [Promega], SUPERase-In [ABI], etc.), use of guanidine chloride, guanidine isothiocyanate, N-lauroylsarcosine, sodium dodecylsulphate (SDS), or a combination thereof. Reducing miRNA degradation in bodily fluid samples is particularly important when sample storage and transportation is required prior to miRNA quantification.

To account for possible losses of a given miRNA during purification, potential RT-PCR inhibition, miRNA contaminants derived from dying or damaged blood or urine cells during sample isolation and treatment, variations in kidney filtration, etc., various additional methods of experimental data normalization can be employed. For example, the following quality control (QC) and normalization methods can be used in the present invention:

a) Ubiquitous miRNAs can be used for QC by comparing their concentrations in subject's plasma with pre-established normal values.

b) Synthetic small RNA (e.g., non-human miRNA) oligonucleotides can be synthesized and used as controls for losses during purification and RT-PCR inhibition (by adding them to bodily fluid samples before RNA purification).

c) To account for variations in kidney filtration (when working with urine samples), miRNA concentration in urine can be normalized on creatinine and/or albumin level.

Kits of the Invention

In conjunction with the above diagnostic, monitoring and screening methods, the present invention provides various kits comprising one or more primer and/or probe sets specific for the detection of the diagnostic miRNA pairs.

Non-limiting examples of the kits of the invention include:

1. A kit for detecting PD comprising primers and/or probes specific for one or more pairs of miRNAs selected from the group consisting of: let-7e/miR-335, miR-107/miR-335, miR-491-5p/miR-335, miR-744/miR-335, miR-99b/miR-335, let-7e/miR-9*, miR-491-5p/miR-9*, let-7e/miR-132, miR-107/miR-132, miR-491-5p/miR-132, let-7e/miR-134, miR-107/miR-134, miR-99b/miR-134, miR-491-5p/miR-134, let-7e/miR-323-3p, miR-107/miR-323-3p, miR-127/miR-323-3p, miR-181b/miR-323-3p, miR-99b/miR-323-3p, miR-491-5p/miR-323-3p, let-7e/miR-411, miR-107/miR411, miR-491-5p/miR-411; miR-155/miR-335, let-7e/miR-146b, miR-491-5p/miR-146a, let-7e/miR-146a, miR-744/miR-146a, miR-155/miR-16, miR-155/miR-132, miR-155/miR-323-3p, miR-155/miR-411, miR-491-5p/miR-146b, miR-155/miR-146a, and miR-155/miR-146b.

2. A kit for differentiating PD from MCI comprising primers and/or probes specific for one or more pairs of miRNAs selected from the group consisting of: let-7e/miR-335, let-7e/miR-9*, miR-107/miR-335, miR-127/miR-323-3p, miR-491-5p/miR-335, miR-491-5p/miR-9*, miR-107/miR-9*, miR-744/miR-335, let-7e/miR-132, miR-107/miR-134, miR-181b/miR-132, let-7e/miR-210, miR-181b/miR-9*, miR-181a/miR-335, miR-491-5p/miR-134, let-7e/miR-874, miR-181b/miR-874, miR-107/miR-132, miR-491-5p/miR-132, miR-107/miR-323-3p, miR-127/miR-134, miR-491-5p/miR-874, miR-491-5p/miR-323-3p, miR-127/miR-432, let-7e/miR-134, let-7e/miR-411, miR-107/miR-411, miR-491-5p/miR-411, miR-107/miR-874, miR-181a/miR-9*, miR-491-5p/miR-210, miR-181b/miR-335, miR-99b/miR-335, miR-107/miR-210, miR-127/487b, miR-181a/miR-874, miR-9/miR-9*, miR-107/miR-487b, miR-107/miR-432, miR-9/miR-335, miR-181a/miR-132, miR-181b/miR-210, and miR-99b/miR-132; let-7e/miR-146a, miR-107/miR-146a, miR-491-5p/miR-146a, miR-107/miR-146b, miR-491-5p/miR-146b, miR-155/miR-874, let-7e/miR-146b, miR-155/miR-9*, miR-155/miR-335, miR-155/miR-411, and miR-744/miR-146a.

3. A kit for differentiating PD from AD comprising primers and/or probes specific for one or more pairs of miRNAs selected from the group consisting of: let-7e/miR-335, miR-107/miR-335, miR-127/miR-323-3p, let-7e/miR-411, miR-99b/miR-335, miR-491-5p/miR-335, miR-127/miR-134, miR-744/miR-335, miR-9/miR-335, miR-181b/miR-335, miR-107/miR-411, miR-181a/miR-335, let-7e/miR-9*, miR-491-5p/miR-411, let-7e/miR-132, miR-181b/miR-132, miR-9/miR-9*, miR-9/miR-134, miR-107/miR-134, miR-181b/miR-874, let-7e/miR-134, miR-107/miR-132, miR-107/miR-9*, miR-127/miR-335, miR-9/miR-132, miR-181b/miR-9*, miR-491-5p/miR-132, let-7e/miR-210, miR-491-5p/miR-9*, miR-107/miR-323-3p, miR-491-5p/miR-323-3p, miR-491-5p/miR-134, let-7e/miR-874, miR-181b/miR-210, miR-9/miR-874, miR-9/miR-485-3p, miR-744/miR-134, miR-181b/miR-323-3p; miR-107/miR-146a, miR-491-5p/miR-146a, miR-155/miR-132, miR-155/miR-335, miR-107/miR-146b, miR-491-5p/miR-146b, miR-9/miR-146a, let-7e/miR-146b, miR-9/miR-146b, let-7e/miR-146a, miR-155/miR-874, miR-155/miR-9*, miR-155/miR-411, miR-744/miR-146a, miR-155/miR-210, miR-155/miR-146b, miR-744/miR-146b, miR-155/miR-146a, miR-155/miR-134, and miR-181b/miR-146b.

4. A kit comprising primers and/or probes specific for one or more combinations of pairs of miRNAs selected from the group consisting of:
(a) miR-181b/miR-323-3p and miR-99b/miR-9*,
(b) miR-491-5p/miR-487b and miR-9/miR-146a, and
(c) miR-491-5p/miR-210 and miR-181a/miR-146b.

Such kits can further include primer and/or probe sets specific for the detection of QC and additional normalizer miRNAs.

Such kits can be useful for direct miRNA detection in bodily fluid samples isolated from patients or can be used on purified RNA samples.

A kit of the invention can also provide reagents for primer extension and amplification reactions. For example, in some embodiments, the kit may further include one or more of the following components: a reverse transcriptase enzyme, a DNA polymerase enzyme (such as, e.g., a thermostable DNA polymerase), a polymerase chain reaction buffer, a reverse transcription buffer, and deoxynucleoside triphosphates (dNTPs). Alternatively (or in addition), a kit can include reagents for performing a hybridization assay. The detecting agents can include nucleotide analogs and/or a labeling moiety, e.g., directly detectable moiety such as a fluorophore (fluorochrome) or a radioactive isotope, or indirectly detectable moiety, such as a member of a binding pair, such as biotin, or an enzyme capable of catalyzing a non-soluble colorimetric or luminometric reaction. In addition, the kit may further include at least one container containing reagents for detection of electrophoresed nucleic acids. Such reagents include those which directly detect nucleic acids, such as fluorescent intercalating agent or silver staining reagents, or those reagents directed at detecting labeled nucleic acids, such as, but not limited to, ECL reagents. A kit can further include miRNA isolation or purification means as well as positive and negative controls. A kit can also include a notice associated therewith in a form prescribed by a governmental agency regulating the manufacture, use or sale of diagnostic kits. Detailed instructions for use, storage and troubleshooting may also be provided with the kit. A kit can also be optionally provided in a suitable housing that is preferably useful for robotic handling in a high throughput setting.

The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container means, into which the solvent is placed, optionally aliquoted. The kits may also comprise a second container means for containing a sterile, pharmaceutically acceptable buffer and/or other solvent.

Where there is more than one component in the kit, the kit also will generally contain a second, third, or other additional container into which the additional components may be separately placed. However, various combinations of components may be comprised in a container.

Such kits may also include components that preserve or maintain DNA or RNA, such as reagents that protect against nucleic acid degradation. Such components may be nuclease or RNase-free or protect against RNases, for example. Any of the compositions or reagents described herein may be components in a kit.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

Selection of miRNAs for Testing

The methods of the instant invention are based on the use of miRNAs enriched in different brain areas as numerators and denominators, which significantly improves test sensitivity and specificity. Table 1 below presents lists of brain-enriched miRNAs, miRNAs enriched in synapses, axons, dendrites and spines ("synapse and/or neurite miRNAs") and miRNAs enriched in different brain areas.

TABLE 1

| miRNAs enriched in brain, different brain areas and neuronal compartments | |
|---|---|
| Brain areas and compartments | Enriched miRNAs |
| Whole brain | Let-7a,c,e, 7, 9, 96, 98, 99a,b, 103, 105, 106a, 107, 124a, 125a, 125b, 127, 128a, 129, 132, 134, 135a, 137, 138, 139, 149, 151, 153, 154, 181a, 181b, 181c, 182, 183, 184, 190, 204, 211, 212, 213, 218, 219-3p, 219-5p, 221, 222, 299-3p, 299-5p, 323-3p, 324-5p, 326, 328, 329, 330, 331, 335, 337, 338-5p, 340, 342, 346, 369-3p, 369-5p, 370, 379, 381, 382, 383, 409-3p, 410, 411, 423-5p, 425, 432, 433-5p, 485-3p, 485-3p,-5p, 487a,b, 488, 491-5p, 494, 495, 496, 497, 504, 522, 539, 541, 543, 551b, 577, 584, 592, 598, 625, 628, 654, 655, 656, 671, 668, 672, 708, 744, 758, 769-3p,-5p, 770, 873, 874, 876-3p, 885-3p,-5p, 889, 935, 939, 941, 1193, 1197, 1224-3p,-5p, 1225-3p, 1237,let-7d*, 7*, 9*, 125b-2*, 129*, 138-2*, 340*, 380*, 411*, 425*, 488*, 744* |
| Synapses, axons, dendrites, spines | Let-7e, 7, 98, 99, 124a, 125a, 125b, 127-3p, 128a, 132, 134, 135a, 137, 138, 154, 182, 183, 213, 218, 323-3p, 329, 337, 369-3p, 369-5p, 370, 381, 382, 409-3p, 425, 433-5p, 483-3p, 485-5p, 487b, 491-5p, 494, 495, 496, 541, 543, 656, 668, 874, 889, 935, 939, 9*, 181a-1* |
| Cortex | 9, 107, 124a, 125a, 125b, 128a, 132, 134, 154, 181c, 212, 213, 222, 323, 330-3p, 338-5p, 342, 381, 382, 425, 433, 491-5p, 885 |
| Hippocampus | 9, 96, 99a, 103, 124a, 125b, 128a, 132, 134, 137, 138, 153, 181a,b,c, 184, 212, 218, 219, 221, 222, 324-5p, 328, 330, 331, 335-5p, 338, 369-3p, 379, 381, 382, 383, 411, 425, 433-5p, 485-5p, 488, 874 |
| Hypothalamus | 7, 124a, 125a, 128a, 132, 136, 138, 212, 338, 451 |
| Cerebellum | 9, 103, 124a, 125b, 128, 132, 134, 137, 138, 181a, 181b, 181c, 204, 212, 213, 218, 338, 381, 382, 425, 432, 489, 592, 874, 885 |
| Amygdala | 103, 134, 138, 182, 183, 222, 323-3p, 369, 381, 382 |
| Spinal cord | 218, 219, 338, 451, 486 |
| Pituitary gland | 7, 96 132, 99a,b, 154, 182, 212, 213, 328, 329, 335, 369, 381, 411, 432 433, 487b |
| Midbrain, | Let-7a,b,c,d,e, 9, 99a,b, 125a,b, 127-3p, 129-3p, 134, 149, 181a, 204, 329, |

TABLE 1-continued miRNAs enriched in brain, different brain areas and neuronal compartments

| Brain areas and compartments | Enriched miRNAs |
|---|---|
| Substantia nigra | 338, 340, 379, 383, 410, 425, 432, 433, 487a,b, 744, 9*, 99b*, 129*, 340* |

Since neuroinflammatory process are involved in PD pathogenesis, several miRNAs associated with inflammatory process were also tested (miR-146a,b, miR-155 and miR-31). miR-210 associated with hypoxia in combination with brain-enriched miRNAs was also analyzed, and muscle-enriched miR-206 was tested to check if movement disorders characteristic of PD affect its concentration in plasma. Finally, ubiquitous miR-16 and miR-196a, which is not practically expressed in the brain, was tested as potential denominator.

Tested miRNAs were initially selected based on literature data on their enrichment in brain compartments and presence in neurites (i.e., axons and/or dendrites and/or spines) and/or synapses (Hua et al. BMC Genomics. 2009; 10: 214; Liang et al. BMC Genomics. 2007; 8:166; Landgraf et al. Cell. 2007; 129: 1401-1414; Lee et al. RNA. 2008; 14: 35-42; Schratt et al. Nature. 2006; 439: 283-289; Lugli et al. J. Neurochem. 2008; 106: 650-661; Bicker and Schratt. J. Cell Mol. Med. 2008; 12: 1466-1476; Smalheiser and Lugli. Neuromolecular Med. 2009; 11: 133-140; Rajasethupathy. Neuron. 2009; 63: 714-716; Kye. RNA. 2007; 13: 1224-1234; Yu et al. Exp. Cell Res. 2008; 314: 2618-2633; Cougot et al. J. Neurosci. 2008; 28: 13793-13804; Kawahara. Brain Nerve. 2008; 60: 1437-1444; Schratt. Rev. Neurosci. 2009; 10: 842-849; Pichardo-Casas et al. Brain Research. 2012; 1436: 20-33) as well as on their suggested involvement in neurite- and synapse-associated processes (The miR-Ontology Data Base: http://ferrolab.dmi.unict.it/miro/). Since there are data indicating involvement of inflammatory processes in development of PD and other neurodegenerative diseases, several inflammation-associated miRNAs as well as miR-210 associated with hypoxia were also pre-selected. Finally, the present inventors tested miR-206 enriched in muscle cells because movement disorders are characteristic of PD and several ubiquitous miRNAs as potential normalizers. Then the present inventors analyzed literature to find out which miRNAs are detectable in plasma. 32 miRNAs were analyzed in the study (Table 2).

TABLE 2 miRNAs used in the study

| miRNA | Brain enrichment | Enriched in | Present in synapses | Comments |
|---|---|---|---|---|
| Let-7e | + | MB, PG, Cer | + | |
| miR-7 | + | PG | + | |
| miR-9 | + | FC, MB, Hip, Cer | | |
| miR-9* | + | MB | | |
| miR-16 | | | | Ubiquitous |
| miR-31 | | | | Inflammatory |
| miR-99b | + | MB | | |
| miR-107 | + | FC | + | |
| miR-127-3p | + | PG, MB, FC | + | |
| miR-132 | + | PG, Hip | + | |
| miR-134 | + | MB, Hip, PG | + | |
| miR-138 | + | Hip, FC | + | |
| miR-146a | | | | Inflammatory |
| miR-146b | | | | Inflammatory |
| miR-155 | | | | Inflammatory |
| miR-181a | + | MB, FC, Hip | + | |
| miR-181b | + | FC, Hip, | | |
| miR-196 | | | | Low in brain |
| miR-206 | | | | Muscle-enriched |
| miR-210 | | | | Hypoxia-activated |
| miR-323-3p | + | FC, MB | + | |
| miR-335-5p | + | PG, Hip | | |
| miR-370 | + | PG, FC | + | |
| miR-411 | + | PG, FC, Hip | + | |
| miR-432 | + | MB, PG | | |
| miR-451 | | | | |
| miR-485-3p | + | Hip | + | |
| miR-487b | + | PG, MB, FC | + | |
| miR-491-5p | + | MB, FC | | |
| miR-744 | + | MB | + | |
| miR-874 | + | Cer, Hip | + | |

Cer-Cerebellum;
FC-Frontal Cortex;
Hip-Hippocampus;
MB-Midbrain;
PG-Pituitary Gland

Example 2

Quantitative Analysis

Mann-Whitney U-test was used to evaluate significance of differentiation of any two patient groups by various biomarker miRNA pairs. Bonferroni correction was applied for estimating significant P-values. In all experiments (differentiation of PD from age-matched control [AMC], MCI and AD) 32 miRNAs were tested, thus P-value<0.0001 (calculated as 0.05/496; 496 here indicates the total number of miRNA pairs examined) was considered significant. A standard formula for a case-control study (Eng J. Radiology. 2003; 227:309-313) was applied for estimating the sample size required to produce statistical power 0.90.

Example 3

Differentiation of PD Patients from Age-Matched Controls (AMC)

Plasma samples were obtained from 20 PD patients and 20 AMC (±2.5 years). Concentrations of brain-enriched miRNAs, inflammation-associated miRNAs, muscle-enriched miR-206 and several ubiquitous miRNAs in plasma were analyzed using RT-qPCR with primers and probes for each individual miRNA (Life Technologies). The amount of RNA equivalent to 25 µL of plasma were taken in each RT reaction, and the amount of miRNA (cDNA) equivalent to 2 µL plasma was taken into final PCR. The results obtained for each miRNA were normalized per potential normalizer miRNA, converted into Relative Concentration (RC) of miRNA according to the ABI protocol ($2^{-\Delta Ct}$), and compared with miRNA profiles from age-matched controls (AMC). The biomarker pairs were selected as described above. Both approaches gave similar results. Correlation of plasma concentrations, P-values for differentiation of PD patients from AMC and AUC (Area under ROC curve) for best miRNA pairs are presented in Table 3 and in FIG. 1.

TABLE 3

Biomarker miRNA pairs for differentiating PD patients from AMC

| Marker | R | Marker | R |
|---|---|---|---|
| let-7e/miR-335 | 0.95 | let-7e/miR-9* | 0.97 |
| miR-107/miR-335 | 0.91 | miR-491-5p/miR-9* | 0.95 |
| miR-491-5p/miR-335 | 0.93 | Let-7e/miR-323-3p | 0.85 |
| miR-744/miR-335 | 0.98 | miR-107/miR-323-3p | 0.84 |
| miR-99b/miR-335 | 0.91 | miR-127/miR-323-3p | 0.84 |
| miR-155/miR-335 | 0.93 | miR-181b/miR-323-3p | 0.89 |
| let-7e/miR-411 | 0.89 | miR-99b/miR-323-3p | 0.90 |
| miR-107/miR-411 | 0.90 | miR-155/miR-323-3p | 0.83 |
| miR-491-5p/miR-411 | 0.89 | miR-491-5p/miR-323-3p | 0.84 |
| miR-155/miR-411 | 0.93 | let-7e/miR-146a | 0.97 |
| let-7e/miR-132 | 0.94 | let-7e/miR-146b | 0.96 |
| miR-107/miR-132 | 0.95 | miR-491-5p/miR-146a | 0.97 |
| miR-491-5p/miR-132 | 0.94 | miR-491-5p/miR-146b | 0.97 |
| miR-155/miR-132 | 0.92 | miR-744/miR-146a | 0.98 |
| Let-7e/miR-134 | 0.92 | miR-155/miR-146a | 0.96 |
| miR-107/miR-134 | 0.94 | miR-155/miR-146b | 0.97 |
| miR-491-5p/miR-134 | 0.91 | miR-155/miR-16 | 0.95 |

R-Correlation coefficient for numerator and denominator miRNAs; Table shows miRNA pairs with P < 0.0001.

Conclusions:
1. miRNAs enriched in midbrain (e.g., let-7e) and frontal cortex (e.g., miR-107), the brain areas suffering in PD, and present in neurites and synapses are the best numerators in miRNA pairs, demonstrating the increase in miRNA ratio from PD patients compared to AMC. Although the inventors could not identify in the literature data on enrichment of miR-491-5p in particular brain areas but it behaves as a very good numerator in miRNA pairs, distinguishing PD and MCI subjects.
2. Brain-enriched miRNAs from brain areas not involved in PD or significantly less damaged are among the best denominators in miRNA pairs capable of differentiating PD and AMC (e.g., miR-132 and miR-335-5p, enriched in hippocampus).
3. Inflammation-associated miRNAs are divided into two groups. miR-155 and to a lesser degree miR-31 are good numerators and miR-146a and miR-146b are good denominators, which indicates that they play a different role in PD development or are located in different cell types.
4. Muscle-enriched miR-206 is not a good marker for PD detection.

Example 4

Differentiation Between PD and MCI Patients

The scheme of experiments was the same as described in the Example 2 above but PD patients were compared with MCI patients to find out biomarker miRNA pairs capable of differentiating PD MCI, which is a heterogeneous syndrome, characteristic of early stages of AD, frontotemporal dementia, vascular dementia, some cases of PD and other neurodegenerative diseases. Data on ability of various miRNA pairs to differentiate PD and MCI patients are presented in FIG. 2 and Table 4. Presented results demonstrate that principally the same miRNA pairs that distinguish PD from AMC differentiate PD from MCI.

TABLE 4

Biomarker miRNA pairs for differentiating PD patients and MCI patients

| Marker | R | Marker | R |
|---|---|---|---|
| let-7e/miR-146a | 0.97 | miR-491-5p/miR-132 | 0.94 |
| let-7e/miR-335 | 0.95 | miR-107/miR-323-3p | 0.84 |
| let-7e/miR-9* | 0.97 | miR-127/miR-134 | 0.96 |
| miR-107/miR-146a | 0.99 | miR-155/miR-335 | 0.93 |
| miR-107/miR-335 | 0.91 | miR-491-5p/miR-874 | 0.85 |
| miR-127/miR-323-3p | 0.95 | miR-491-5p/miR-323-3p | 0.84 |
| miR-491-5p/miR-146a | 0.97 | miR-127/miR-432 | 0.99 |
| miR-491-5p/miR-335 | 0.93 | let-7e/miR-134 | 0.92 |
| miR-491-5p/miR-9* | 0.95 | miR-107/miR-874 | 0.81 |
| miR-107/miR-146b | 0.97 | miR-181a/miR-9* | 0.89 |
| miR-107/miR-9* | 0.97 | miR-491-5p/miR-210 | 0.95 |
| miR-744/miR-335 | 0.93 | miR-181b/miR-335 | 0.89 |
| miR-491-5p/miR-146b | 0.97 | miR-99b/miR-335 | 0.91 |
| miR-155/miR-874 | 0.88 | miR-107/miR-210 | 0.93 |
| let-7e/miR-132 | 0.94 | miR-127/miR-487b | 0.94 |
| miR-107/miR-134 | 0.94 | miR-181a/miR-874 | 0.87 |
| miR-181b/miR-132 | 0.93 | miR-744/miR-146a | 0.98 |
| let-7e/miR-210 | 0.94 | miR-9/miR-9* | 0.98 |
| Let-7e/miR-411 | 0.89 | miR-155/miR-210 | 0.94 |
| miR-107/miR-411 | 0.90 | miR-99b/miR-9* | 0.97 |
| miR-491-5p/miR-411 | 0.89 | miR-107/miR-487b | 0.92 |
| let-7e/miR-874 | 0.85 | miR-107/miR-432 | 0.91 |
| miR-181b/miR-874 | 0.87 | miR-9/miR-335 | 0.94 |
| let-7e/miR-146b | 0.97 | miR-181a/miR-132 | 0.89 |
| miR-107/miR-132 | 0.95 | miR-181b/miR-210 | 0.91 |
| miR-155/miR-411 | 0.93 | miR-99b/miR-132 | 0.95 |

R-Correlation coefficient for numerator and denominator miRNAs; Table shows miRNA pairs with P < 0.0001.

Example 5

Differentiation Between PD and AD Patients

Again the scheme of experiments was the same as described in the Example 2 above but PD patients were compared with AD patients to find out biomarker miRNA pairs capable of differentiating these two neurodegenerative diseases. Data on ability of different miRNA pairs to differentiate PD and AD patients are presented in FIG. 3 and Table 5. Presented results again demonstrate that principally the same miRNA pairs that distinguish PD from AMC and MCI differentiate PD from AD. Interestingly, in the two latter cases (differentiation of PD from AD and MCI) miR-210 associated with hypoxia behaves as a good denominator.

TABLE 5

Biomarker miRNA pairs for differentiating PD patients and AD patients

| Marker | R | Marker | R |
|---|---|---|---|
| let-7e/miR-335 | 0.95 | miR-9/miR-9* | 0.98 |
| miR-107/miR-146a | 0.99 | miR-9/miR-134 | 0.9 |
| miR-107/miR-335 | 0.91 | miR-107/miR-134 | 0.94 |
| miR-127/miR-323-3p | 0.95 | miR-181b/miR-874 | 0.87 |
| miR-107/miR-411 | 0.90 | let-7e/miR-134 | 0.92 |
| miR-99b/miR-335 | 0.91 | miR-107/miR-132 | 0.95 |
| miR-491-5p/miR-146a | 0.97 | miR-107/miR-9* | 0.97 |
| miR-491-5p/miR-335 | 0.93 | miR-155/miR-146b | 0.97 |
| miR-127/miR-134 | 0.96 | miR-127/miR-335 | 0.84 |
| miR-155/miR-132 | 0.92 | miR-9/miR-132 | 0.93 |
| miR-155/miR-335 | 0.93 | miR-744/miR-146b | 0.94 |
| miR-744/miR-335 | 0.93 | miR-181b/miR-9* | 0.94 |
| miR-9/miR-335 | 0.94 | miR-491-5p/miR-132 | 0.94 |
| miR-107/miR-146b | 0.97 | let-7e/miR-210 | 0.94 |
| miR-181b/miR-335 | 0.89 | miR-491-5p/miR-9* | 0.95 |
| miR-491-5p/miR-146b | 0.97 | miR-107/miR-323-3p | 0.84 |
| Let-7e/miR-411 | 0.89 | miR-491-5p/miR-323-3p | 0.84 |
| miR-9/miR-146a | 0.97 | miR-155/miR-146a | 0.95 |
| miR-181a/miR-335 | 0.89 | miR-491-5p/miR-134 | 0.91 |
| let-7e/miR-146b | 0.97 | miR-155/miR-411 | 0.87 |
| miR-9/miR-146b | 0.97 | let-7e/miR-874 | 0.85 |
| let-7e/miR-146a | 0.97 | miR-181b/miR-210 | 0.91 |
| miR-155/miR-874 | 0.88 | miR-9/miR-874 | 0.85 |
| miR-155/miR-9* | 0.97 | miR-155/miR-16 | 0.92 |
| miR-744/miR-146a | 0.94 | miR-155/miR-134 | 0.88 |
| let-7e/miR-9* | 0.97 | miR-9/miR-485-3p | 0.89 |
| miR491-5p/miR-411 | 0.89 | miR-744/miR-134 | 0.92 |
| miR-155/miR-210 | 0.94 | miR-181b/miR-323-3p | 0.82 |
| let-7e/miR-132 | 0.86 | miR-181b/miR-146b | 0.94 |
| miR-181b/miR-132 | 0.93 | | |

R-Correlation coefficient for numerator and denominator miRNAs; Table shows miRNA pairs with AUC > 0.9 and P < 0.0001.

SUMMARY

Sensitivity and specificity of PD detection and differentiation from MCI and AD is very high, reaching for some pairs 100% accuracy:
PD Versus AMC
let-7e/miR-335; let-7e/miR-411; miR-107/miR-146a; miR-107/miR-335; miR-107/miR-411; miR-155/miR-335; miR-181b/miR-335; miR-491-5p/miR-335; miR-491-5p/miR-411; miR-155/miR-146a
PD Versus MCI
let-7e/miR-146a; let-7e/miR-335; let-7e/miR-miR-411; miR-107/miR-146a; miR-107/miR-335; miR-127/miR-323-3p; miR-491-5p/miR-146a; miR-491-5p/miR-335; miR-491-5p/miR-9*; miR-744/miR-335; miR-491-5p/miR-146b
PD Versus AD
miR-107/miR-146a; miR-107/miR-335; miR-127/miR-323-3p; let-7e/miR-411; miR-99b/miR-335; miR-491-5p/miR-146a; miR-491-5p/miR-335; miR-155/miR-132; miR-155/miR-335; miR-744/miR-335.

Figure 4A:
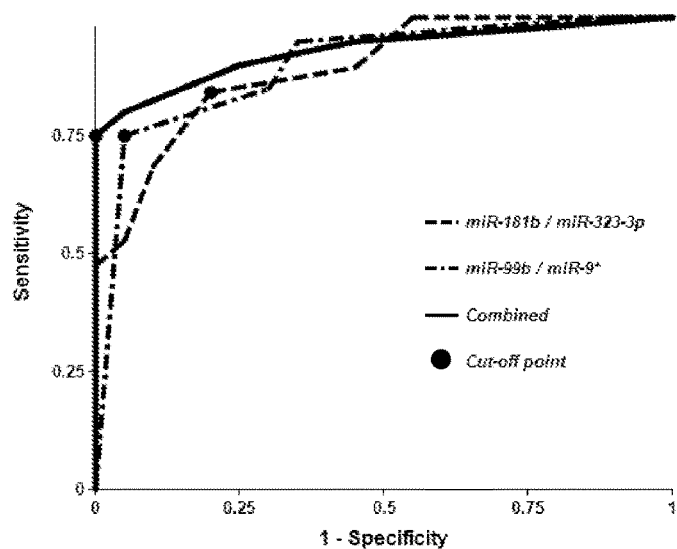
FIGS. 4A-C present Receiver-Operating Characteristic (ROC) curve analysis of differentiation between PD patients and AMC (A), PD and MCI patients (B) and PD and AD patients (C). Sensitivity, specificity and accuracy for each biomarker/normalizer pair and their combination are calculated for the "cutoff" point (indicated as a dot on each plot)—the value of the ratio of paired miRNA where the accuracy of predictions is the highest.
Figure 4B:
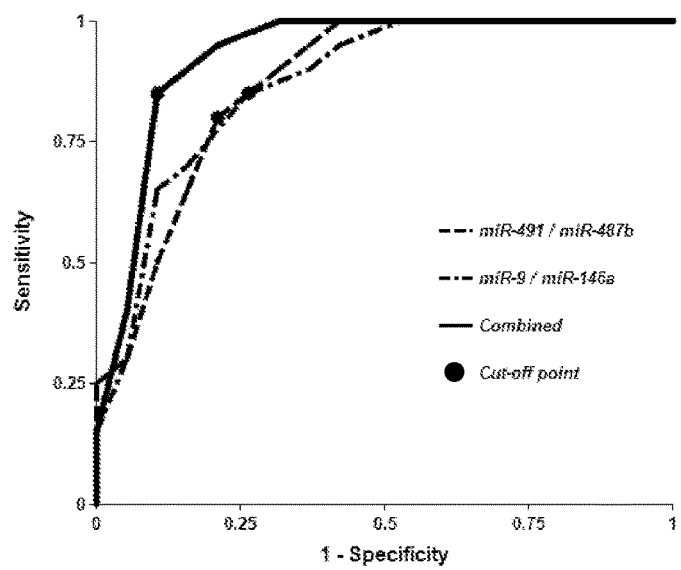
Figure 4C:
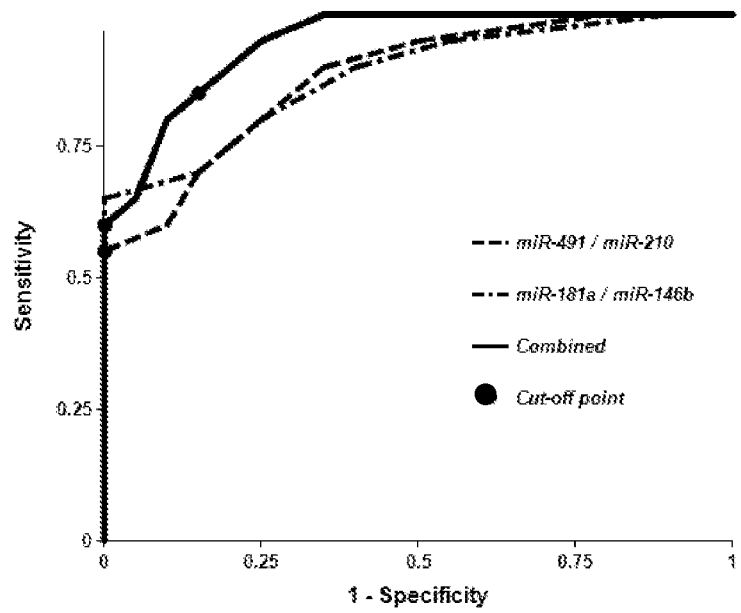

It is also important that some biomarker miRNA pairs detecting PD or differentiating it from other neurodegenerative pathologies with lower accuracy being combined also demonstrate high sensitivity and specificity (FIG. 4). Table 6 presents typical data demonstrating significance of correlation between numerator and denominator in biomarker miRNA pairs—as higher is correlation as lower is P-value for differentiating two subject cohorts.

TABLE 6

The importance of correlation between numerator and denominator miRNAs in biomarker miRNA pairs.

| Compared | Marker | R | P |
|---|---|---|---|
| PD-AMC | let-7e/miR-335 | 0.95 | 0.00E+00 |
| | let-7e/miR-370 | 0.74 | 1.08E−03 |
| | let-7e/miR-451 | 0.4 | 2.59E−01 |
| PD-MCI | miR-155/miR-335 | 0.93 | 9.60E−06 |
| | miR-155/miR-370 | 0.72 | 1.31E−01 |
| | miR-155/miR-451 | 0.52 | 3.08E−01 |
| PD-AD | miR-107/miR-335 | 0.91 | 0.00E+00 |
| | miR-107/miR-16 | 0.75 | 1.90E−04 |
| | miR-107/miR-370 | 0.71 | 1.30E−02 |

Compared-compared subject cohorts.
R-Correlation coefficient for numerator and denominator miRNAs.
P-P-value.

Table 7 presents lists of miRNAs used as numerators and denominators in the best biomarker miRNA pairs (capable of differentiating PD from AMC, MCI and AD with P-value<2E-04).

TABLE 7

The list of most common numerator and denominator miRNAs in biomarker miRNA pairs capable of differentiating various subject cohorts

| Compared cohorts | Numerators Name | Denominators Name |
|---|---|---|
| PD-AMC | miR-107 | miR-335 |
| | let-7e | miR-411 |
| | miR-491-5p | miR-132 |
| | miR-155 | miR-134 |
| | miR-99b | miR-146a |
| | miR-127 | miR-146b |
| | miR-744 | miR-323-3p |
| PD-MCI | let-7e | miR-9* |
| | miR-107 | miR-132 |
| | miR-127 | miR-146a |
| | miR-155 | miR-146b |
| | miR-181a | miR-335 |
| | miR-181b | miR-411 |
| | miR-370 | miR-432 |
| | miR-744 | miR-487 |
| | miR-9 | miR-874 |
| | miR-99b | miR-134 |
| | miR-491-5p | miR-323-3p |
| | | miR-485-3p |
| PD-AD | let-7e | miR-9* |
| | miR-107 | miR-132 |
| | miR-127 | miR-146a |
| | miR-155 | miR-146b |
| | miR-181a | miR-335 |
| | miR-181b | miR-210 |
| | miR-744 | miR-411 |
| | miR-9 | miR-874 |
| | miR-99b | miR-134 |
| | miR-491-5p | miR-323-3p |
| | miR-411 | miR-485-3p |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method for monitoring the effect of a treatment on development of Parkinson's disease (PD) in a subject who had been previously diagnosed with PD, which method comprises:
   a) collecting one or more bodily fluid sample(s) from the subject prior to initiation of the treatment,
   b) administering the treatment to the subject,
   c) collecting one or more bodily fluid sample(s) from the subject in the course of or following the treatment,
   d) measuring the level of a first miRNA and the level of a second miRNA in the one or more bodily fluid sample(s) collected from the subject prior to initiation of the treatment,
   e) determining the ratio of the level of the first miRNA (numerator) to the level of the second miRNA (denominator) measured in step (d), wherein said numerator/denominator miRNA ratio is selected from let-7e/miR-335, miR-107/miR-335, miR-744/miR-335, miR-99b/miR-335, miR-155/miR-335, miR-181b/miR-335, let-7e/miR-9*, let-7e/miR-132, miR-107/miR-132, miR-155/miR-132, let-7e/miR-134, miR-107/miR-134, miR-99b/miR-134, miR-155/miR-134, let-7e/miR-323-3p, miR-107/miR-323-3p, miR-99b/miR-323-3p, miR-155/miR-323-3p, miR-127/miR-323-3p, miR-181b/miR-323-3p, miR-744/miR-323-3p, let-7e/miR-411, miR-107/miR-411, miR-155/miR-411, let-7e/miR-146a, miR-744/miR-146a, miR-155/miR-146a, miR-99b/miR-146a, miR-107/miR-146a, let-7e/miR-146b, miR-155/miR-146b, miR-127/miR-146b, and miR-155/miR-16,
   f) determining the ratio of the levels of the same first (numerator) and second (denominator) miRNAs as in step (e) in the one or more bodily fluid sample(s) collected from the subject in the course of or following the treatment;
   g) comparing the ratios of the levels of the numerator and denominator miRNAs determined in steps (e) and (f), and optionally comparing the ratios of the levels of the numerator and denominator miRNAs determined in step (f) between different samples in step (c), and
   h) (i) determining that the PD treatment is effective if the ratio of the levels of the miRNAs determined in step (e) is higher than the corresponding ratio(s) determined in step (f), and continuing to administer said PD treatment to the subject, or (ii) determining that the PD treatment is not effective if the ratio of the levels of the miRNAs determined in step (e) is not higher than the corresponding ratio(s) determined in step (f) and discontinuing the administration of said PD treatment to the subject.

2. The method of claim 1, further comprising recruiting the subject in a clinical trial.

3. The method of claim 1, wherein the bodily fluid is selected from blood plasma, serum, urine, cerebrospinal fluid (CSF), and saliva.

4. The method of claim 1, wherein the level of the miRNAs is determined using hybridization, RT-PCR, or sequencing.

5. The method of claim 1, wherein, prior to determining miRNA levels, the miRNA is purified from the bodily fluid sample.

6. The method of claim 1, further comprising the step of reducing or eliminating degradation of the miRNAs.

7. The method of claim 1, wherein said numerator/denominator miRNA ratio is selected from let-7e/miR-335, miR-107/miR-335, miR-155/miR-335, miR-181b/miR-335, let-7e/miR-411, miR-107/miR-411, miR-155/miR-146a, and miR-107/miR-146a.

8. The method of claim 1, comprising determining two or more different numerator/denominator miRNA ratios recited in step (e).

9. A method for identifying a compound useful for slowing down the progression or treating Parkinson's disease (PD) in a subject who had been previously diagnosed with PD, which method comprises:
   a) collecting one or more bodily fluid sample(s) from the subject prior to a test compound administration,
   b) administering the test compound to the subject,
   c) collecting one or more bodily fluid sample(s) from the subject following administration of the test compound,
   d) measuring the level of a first miRNA (numerator) and the level of a second miRNA (denominator) in the one or more bodily fluid sample(s) collected from the subject prior to the test compound administration,
   e) determining the ratio of the level of the first miRNA (numerator) to the level of the second miRNA (denominator) measured in step (d), wherein said numerator/denominator miRNA ratio is selected from let-7e/miR-335, miR-107/miR-335, miR-491-5p/miR-335, miR-744/miR-335, miR-99b/miR-335, miR-155/miR-335, miR-181b/miR-335, let-7e/miR-9*, let-7e/miR-132, miR-107/miR-132, miR-155/miR-132, let-7e/miR-134, miR-107/miR-134, miR-99b/miR-134, miR-155/miR-134, let-7e/miR-323-3p, miR-107/miR-323-3p, miR-99b/miR-323-3p, miR-155/miR-323-3p, miR-127/miR-323-3p, miR-181b/miR-323-3p, miR-744/miR-323-3p, let-7e/miR-411, miR-107/miR-411, miR-491-5p/miR-411, miR-155/miR-411, let-7e/miR-146a, miR-744/miR-146a, miR-155/miR-146a, miR-99b/miR-146a, miR-107/miR-146a, let-7e/miR-146b, miR-155/miR-146b, miR-127/miR-146b, and miR-155/miR-16,
   f) determining the ratio of the levels of the same first (numerator) and second (denominator) miRNAs as in step (e) in the one or more bodily fluid samples collected from the subject following administration of the test compound;
   g) comparing the ratio of the levels of the numerator and denominator miRNAs determined in steps (e) and (f), and
   h) (i) identifying that the test compound is useful for slowing down the progression or treating PD if the ratio of the levels of the miRNAs determined in step (f) is lower than the ratio of the levels of the miRNAs determined in step (e); (ii) identifying that the test compound is not useful for slowing down the progression or treating PD if the ratio of the levels of the miRNAs determined in step (f) is not lower than the ratio of the levels of the miRNAs determined in step (e).

10. The method of claim 9, wherein the bodily fluid is selected from blood plasma, serum, urine, cerebrospinal fluid (CSF), and saliva.

11. The method of claim 9, wherein the level of the miRNAs is determined using hybridization, RT-PCR, or sequencing.

12. The method of claim 9, wherein, prior to determining miRNA levels, the miRNA is purified from the bodily fluid sample.

13. The method of claim 9, further comprising the step of reducing or eliminating degradation of the miRNAs.

14. The method of claim 9, wherein said numerator/denominator miRNA ratio is selected from let-7e/miR-335, miR-107/miR-335, miR-491-5p/miR-335, miR-155/miR-335, miR-181b/miR-335, let-7e/miR-411, miR-107/miR-411, miR-491-5p/miR-411, miR-155/miR-146a, and miR-107/miR-146a.

15. The method of claim 9, comprising determining two or more different numerator/denominator miRNA ratios recited in step (e).

* * * * *